US006545013B2

(12) United States Patent
Langham et al.

(10) Patent No.: US 6,545,013 B2
(45) Date of Patent: Apr. 8, 2003

(54) 2,7-NAPHTHYRIDINE DERIVATIVES

(75) Inventors: Barry John Langham, Reading (GB); Rikki Peter Alexander, High Wycombe (GB); John Clifford Head, Maidenhead (GB); Janeen Marsha Linsley, High Wycombe (GB); John Robert Porter, Chinnor (GB); Sarah Catherine Archibald, Maidenhead (GB); Graham John Warrellow, Northwood (GB)

(73) Assignee: Celltech R&D Limited, Slough (GB)

( * ) Notice: Subject to any disclaimer, the term of this patent is extended or adjusted under 35 U.S.C. 154(b) by 0 days.

(21) Appl. No.: 09/867,016

(22) Filed: May 29, 2001

(65) Prior Publication Data

US 2002/0115684 A1 Aug. 22, 2002

(30) Foreign Application Priority Data

May 30, 2000 (GB) .............................. 0013101
Nov. 27, 2000 (GB) .............................. 0028841

(51) Int. Cl.[7] ..................... A61K 31/435; C07D 47/104
(52) U.S. Cl. ........................ 514/300; 514/212; 514/218; 540/481; 540/575; 540/597; 546/122
(58) Field of Search .................... 546/122; 540/481, 540/575, 597; 514/212, 218, 300

(56) References Cited

U.S. PATENT DOCUMENTS

| 4,470,973 A | 9/1984 | Natarajan et al. ............ 424/177 |
| 4,554,273 A | 11/1985 | Bayssat et al. .............. 514/221 |
| 4,987,132 A | 1/1991 | Mase et al. ................. 514/252 |
| 5,164,372 A | 11/1992 | Matsuo et al. ................ 514/19 |
| 5,227,490 A | 7/1993 | Hartman et al. ............. 514/317 |
| 5,260,277 A | 11/1993 | McKenzie ................... 544/18 |
| 5,296,486 A | 3/1994 | Lazer et al ................. 514/333 |
| 5,399,585 A | 3/1995 | Alig et al. ................... 514/438 |
| 5,510,346 A | 4/1996 | Martin et al. ............... 514/221 |
| 5,698,691 A | 12/1997 | Yukimasa et al. .......... 540/481 |
| 5,773,646 A | 6/1998 | Kumar ....................... 562/439 |
| 6,093,696 A | 7/2000 | Head et al. .................... 514/19 |
| 6,166,050 A | 12/2000 | Lombardo et al. ..... 514/352.18 |

FOREIGN PATENT DOCUMENTS

| DE | 23 16 881 A | 10/1973 |
| DE | 28 37 264 A1 | 3/1979 |

(List continued on next page.)

OTHER PUBLICATIONS

Abraham, W.M. et al., "$\alpha_4$–Integrins Mediate Antigen–Induced Late Bronchial Responses and Prolonged Airway Hyperresponsiveness in Sheep," *J. Clin. Invest.*, 1994, 93, 776–787.

Alhaique, F., et al., "Cyclisation of dinitriles by sodium alkoxides a new synthesis of naphthyridines," *Tetrahedron Letters*, 1975, 3, 173–174.

Ames, D.E., et al., "Condensation of β–dicarbonyl compounds with halogenopyridinecarb–oxylic acids. A convenient synthesis of some naphthyridine derivatives," *J.C.S. Perkin I*, 1972, 705–710.

(List continued on next page.)

*Primary Examiner*—Bernard Dentz
(74) *Attorney, Agent, or Firm*—Woodcock Washburn LLP

(57) ABSTRACT

2,7-Naphthyridine containing squaric acids of formula (1) are described:

$$Ar^1L^2Ar^2Alk-N(R^1)-\text{[squarate]}-L^1(Alk^1)_nR^2 \quad (1)$$

wherein $Ar^1$ is an optionally substituted 2,7-naphthridin-1-yl group;

$L^2$ is a covalent bond or a linker atom or group;

$Ar^2$ is an optionally substituted aromatic or heteroaromatic chain;

Alk is a chain $$-CH_2CH(R)-, \; -CH=C(R)-,$$

$$-\underset{CH_2R}{\overset{|}{CH}}- \quad \text{or} \quad -\underset{CHR}{\overset{\|}{C}}-$$

in which R is a carboxylic acid ($-CO_2H$) or a derivative or biostere thereof;

$R^1$ is a hydrogen atom or a $C_{1-6}$alkyl group;

$L^1$ is a covalent bond or a linker atom or group;

$Alk^1$ is an optionally substituted aliphatic chain;

n is zero or the integer 1;

$R^2$ is a hydrogen atom or an optionally substituted heteroaliphatic, cycloaliphatic, heterocycloaliphatic, polycycloalphatic, heteropoly-cycloaliphatic, aromatic or heteroaromatic group;

and the salts, solvates, hydrates and N-oxides thereof.

The compounds are able to inhibit the binding of integrins to their ligands and are of use in the prophylaxis and treatment of immuno or inflammatory disorders or disorders involving the inappropriate growth or migration of cells.

20 Claims, No Drawings

FOREIGN PATENT DOCUMENTS

| | | |
|---|---|---|
| WO | WO 97/44333 | 11/1997 |
| WO | WO 97/47618 | 12/1997 |
| WO | WO 98/00395 | 1/1998 |
| WO | WO 98/04247 | 2/1998 |
| WO | WO 98/04913 | 2/1998 |
| WO | WO 98/18460 | 5/1998 |
| WO | WO 98/25892 | 6/1998 |
| WO | WO 98/31359 | 7/1998 |
| WO | WO 98/42662 | 10/1998 |
| WO | WO 98/53814 | 12/1998 |
| WO | WO 98/53817 | 12/1998 |
| WO | WO 98/53818 | 12/1998 |
| WO | WO 98/54207 | 12/1998 |
| WO | WO 98/58902 | 12/1998 |
| WO | WO 99/06390 | 2/1999 |
| WO | WO 99/06431 | 2/1999 |
| WO | WO 99/06432 | 2/1999 |
| WO | WO 99/06433 | 2/1999 |
| WO | WO 99/06434 | 2/1999 |
| WO | WO 99/06435 | 2/1999 |
| WO | WO 99/06436 | 2/1999 |
| WO | WO 99/06437 | 2/1999 |
| WO | WO 99/10312 | 3/1999 |
| WO | WO 99/10313 | 3/1999 |
| WO | WO 99/20272 | 4/1999 |
| WO | WO 99/26921 | 6/1999 |
| WO | WO 99/26922 | 6/1999 |
| WO | WO 99/26945 | 6/1999 |
| WO | WO 99/30709 | 6/1999 |
| WO | WO 99/31061 | 6/1999 |
| WO | WO 99/31099 | 6/1999 |
| WO | WO 99/32457 | 7/1999 |
| WO | WO 99/35163 | 7/1999 |
| WO | WO 99/36393 | 7/1999 |
| WO | WO 99/37618 | 7/1999 |
| WO | WO 99/43642 | 9/1999 |
| WO | WO 99/44994 | 9/1999 |
| WO | WO 99/48879 | 9/1999 |
| WO | WO 99/52879 | 10/1999 |
| WO | WO 99/52896 | 10/1999 |
| WO | WO 99/52898 | 10/1999 |
| WO | WO 99/60015 | 11/1999 |
| WO | WO 99/61465 | 12/1999 |
| WO | WO 99/64395 | 12/1999 |
| WO | WO 99/67230 | 12/1999 |
| WO | WO 00/00486 | 1/2000 |
| WO | WO 00/01383 | 1/2000 |
| WO | WO 00/06169 | 2/2000 |
| WO | WO 00/07544 | 2/2000 |
| WO | WO 00/17197 | 3/2000 |
| WO | WO 00/20396 | 4/2000 |
| WO | WO 00/23419 | 4/2000 |
| WO | WO 00/31067 | 6/2000 |
| WO | WO 00/35855 | 6/2000 |
| WO | WO 00/73260 | 12/2000 |
| DE | 196 54 483 A | 1/1998 |
| EP | 0 031 104 A1 | 7/1981 |
| EP | 0 048 763 A1 | 4/1982 |
| EP | 0 144 230 A2 | 6/1985 |
| EP | 0 288 176 A1 | 10/1988 |
| EP | 0 322 068 A1 | 6/1989 |
| EP | 0 394 989 A2 | 10/1990 |
| EP | 0 498 268 A2 | 8/1992 |
| EP | 0 596 406 A1 | 5/1994 |
| EP | 0 710 657 A1 | 5/1996 |
| EP | 0 710 659 A1 | 5/1996 |
| EP | 0 842 943 A2 | 5/1998 |
| EP | 0 842 945 A2 | 5/1998 |
| JP | 56 090045 | 7/1981 |
| JP | 03 135962 | 6/1991 |
| WO | WO 86/02353 | 4/1986 |
| WO | WO 93/00095 | 1/1993 |
| WO | WO 93/08174 | 4/1993 |
| WO | WO 93/09795 | 5/1993 |
| WO | WO 94/15954 | 7/1994 |
| WO | WO 94/15955 | 7/1994 |
| WO | WO 94/29285 | 12/1994 |
| WO | WO 95/13811 | 5/1995 |
| WO | WO 95/15973 | 6/1995 |
| WO | WO 95/19356 | 7/1995 |
| WO | WO 95/35314 | 12/1995 |
| WO | WO 96/01644 | 1/1996 |
| WO | WO 96/22966 | 8/1996 |
| WO | WO 96/26190 | 8/1996 |
| WO | WO 97/03094 | 1/1997 |
| WO | WO 97/04247 | 2/1997 |
| WO | WO 97/08145 | 3/1997 |
| WO | WO 97/12866 | 4/1997 |
| WO | WO 97/23480 | 7/1997 |
| WO | WO 97/24124 | 7/1997 |
| WO | WO 97/31907 | 9/1997 |
| WO | WO 97/36858 | 10/1997 |
| WO | WO 97/36859 | 10/1997 |
| WO | WO 97/36861 | 10/1997 |
| WO | WO 97/36862 | 10/1997 |

OTHER PUBLICATIONS

Azzouny, A.E., et al., "Zur Synthese Acyclischer und Cyclischer Anthranilsäure–Phenylalanin–Peptide," *Pharmazie*, 1977, 32(6), 318–323 (German language only).

Bach et al., "Anomalous optical rotation and circular dichroism of N–thioacylated alpha amino acids and deriva," *Acta Chem. Scand.*, 1966, 20(10), 2781–2794.

Badshah, A., et al., "Catalytic reduction of azlactones in alkaline media. Synthesis of amino acids," *J. of Organic Chemistry*, 1972, 37(18), 2916–2918.

Barrett, G.C., "Circular dichroism of N–thiobenzoyl–1–α–amino acids. III. Their circular dichroism through the near–ultraviolet wavelength range," *J. Chem. Soc.*, 1967, Section C, 1–5.

Berlin, C. et al., "α4β7 Integrin Mediates Lymphocyte Binding to the Mucosal Vascular Addressin MAdCAM–1," *Cell*, 1993, 74, 185–195.

Binns, R.M. et al., "The Role of E–Selectin in Lymphocyte and Polymorphonuclear Cell Recruitment into Cutaneous Delayed Hypersensitivity Reactions in Sensitized Pigs," *J. Immunol.*, 1996, 157, 4094–409.

Bodor, N., "Novel approaches in prodrug design," *Alfred Benzon Symposium*, 1982, 17, 156–177.

Briskin, M.J. et al., "Structural Requirements for Mucosal Vascular Addressin Binding to Its Lymphocyte Receptor $\alpha_4\beta_7$," *J. Immunol.*, 1996, 156, 719–726.

Brooks, Peter C., et al., "Antiintegrin αvβ3 blocks human breast cancer growth and angiogenesis in human skin," *J. Clin. Invest.*, 1995, 96, 1815–1822.

Buckle, D.R., et al., "Non Thiazolidinedione Antihyperglycaemic Agents. 1: α–Heteroatom Substituted β–Phenylpropanoic Acids," *Bioorg. Med. Chem. Lett.*, 1996, 6(17), 2121–2126.

Bundgaard, H., *Design of Prodrugs*, 1985, Elsevier, Amsterdam.

Cardarelli, P.M. et al., "Cyclic RGD Peptide Inhibits α4β7 Interaction with Connecting Segment 1 and Vascular Cell Adhesion Molecule," *J. Biol. Chem.*, 1994, 269(28), 18668–18673.

"Cephalosporins," *Jpn. Kokai Tokkyo Koho*, 40 pages, doc. No. 99:5433 (abstract only, 2 pages); JP 57118588.

Koho, *Chemical Abstracts*, "N–[4–Thiazolidinyl)carbonyl] amino acid derivatives," 1981, 95(19), Abstract No. 169173f, 1 page; JP Patent, XP–002114107.

Clausen, K., et al., "Studies on amino acids and peptides. II. Synthesis of protected endothiodipeptides," *J. Chem. Scr.*, 1982, 20(1–2), 14–18, doc. No. 97:163474 (abstract only, 1 page).

Katritzky, A.R., et al. (Eds.), Comprehensive Organic Functional Group Transformations, Pergamon, 1995.

Corey, E.J. et al., "A Synthetic Method for Formyl → Ethynyl Conversion (RCHO → RC≡CH or RC≡CR')," *Tetrahedron Lett.*, 1972, 36, 3769–3772.

Cornforth, J.W., "Oxazoles and Oxazolones," *Chem. Penicillin*, Princeton Book Review, 1949, pp. 688, 799, and 800.

Davies, S..G., et al., "Asymmetric synthesis of R–β–amino butanoic acid and S–β–tyrosine: homochiral lithium amide equivalents for Michael additions to α,β–unsaturated esters," *Tetra. Asymmetry*, 1991, 2(3), 183–186.

Erle, D.J., et al., "Expression and function of the Mad-CAM–1 receptor, integrin α4β7, on human leukocytes," *J. Immunol.*, 1994, 153, 517–528.

Encyclopedia of Reagents for Organic Synthesis, *John Wiley and Sons* (eds.), 1995.

Ferguson, T.A. et al., "Two integrin–binding peptides abrogate T cell–mediated immune responses in vivo," *Proc. Natl. Acad. Sci. USA*, 1991, 88, 8072–8076.

Frank, R., et al., "Extremely mild reagent for Boc deprotection," *Chem. Commun. (Cambridge)*, 1996, 22, 2509–2510, doc. No. 126:104395 (abstract only, 3 pages).

Fu, H. et al., "Preliminary study on synthesis and antitumor activity in vitro of derivatives of timonacic," *Chemicals Abstracts*, 1988, 108(17), Abstract No. 150358k, 1 page.

Giacomello, et al., "Synthesis of 2,6–naphthyridine," *Tetra. Letters*, 1965, 16, 1117–1121.

Green, T.W., et al., "Protective Groups in Organic Synthesis," *John Wiley and Sons* (eds.), 1991.

Hammes, H., et al., "Subcutaneous injection of a cyclic peptide antagonist of vitronectin receptor–type integrins inhibits retinal neovascularization," *Nature Medicine*, 1996, 2, 529–533.

Harris, R.L.N. et al., *Aust. J. Chem.*, "Potential wool growth inhibitors. 2(1H)–Pyridone analogs of mimosine," 1977, 30(3), 649–655.

Hartke, K. et al., "Dithio and thiono esters. Part 61. Synthesis of α–amino dithioesters and endothiodipeptides,", *J. Prakt. Chem.*, 1996, 338(3), 251–256.

Hodivala–Dilke, K.M., "β3–integrin–deficient mice are a model for glanzmann thrombasthenia showing placental defects and reduced survival," *J. Clin. Invest.*, 1999, 103(2), 229–238.

Holzmann, B., et al., "Peyer's patch–specific lymphocyte homing receptors consist of a VLA–4–like α chain associated with either of two integrin β chains, one of which is novel," *EMBO J.*, 1989, 8(6), 1735–1741.

Humphries, M.J. et al., "Mechanisms of VCAM–1 and fibronectin binding to integrin $\alpha_4\beta_1$: implications for integrin function and rational drug design," *Ciba Foundation Symposium*, 1995, 189, 177–194.

Issekutz, T.B., "Inhibition of Lymphocyte Endothelial Adhesion and In Vivo Lymphocyte Migration to Cutaneous Inflammation by TA–3, a New Monoclonal Antibody to Rat LFA–1," *J. Immunol.*, 1992, 149(10), 3394–3402.

Jaynes, B.H. et al., "Synthesis and In Vivo Antibacterial Activity of Hygromycin a Analogs Modified at the $C_4$' Aryl Position," *Bioorg. Med. Chem. Letts.*, 1993, 3(8), 1531–1536.

Jepson, J.B. et al., "Reactions of α–Thioacylamino–acids. Their conversion into Thiazolones and Derivatives Thereof," *J. Chem. Soc.*, 1955, 1791–1797.

Kalvin, D.M., et al., Synthesis of (4R)–D,L–[4–$^2$H]– and (4S)–D,L–[4–$^2$H] homoserine lactones, *J. Org. Chem.*, 1985, 50, 2259–2263.

Keenan, R.M. et al., "Discovery of Potent Nonpeptide Vitronectin Receptor (avβ$_3$) Antagonists," *J. Med. Chem.*, 1997, 40(15), 2289–2292.

Kobayashi, A., et al., "Synthesis of 2–dialkylamino–4,4–disubstituted 5 (4H)–thiazolones," *J. Yakugaku Zasshi*, 1970, 90(11), 1377–1380, doc. No. 74:31713 (abstract only, 3 pages).

Koenig, H.B., et al., ".beta.–Lactam antibiotics," *Ger. Offen.*, 41 pages, doc. No. 83:97276 (abstract only, 5 pages); German patent.

Koivunen, E., et al., "Selection of peptides binding to the $\alpha_5\beta_1$ integrin from phage display library," *J. Biological Chemistry*, 1993, 268(27), 20205–20210.

Lei, H. et al., "Efficient Synthesis of a Phosphinate Bis–Amino Acid and Its Use in the Construction of Amphiphilic Peptides," *J. Org. Chem.*, 1994, 59, 4206–4210.

Li, Z. et al., "Effect of an anti–Mo1 MAb on ozone–induced airway inflammation and airway hyperresponsiveness in dogs," *Am. J. Physiol.*, 1992, 263(6 Pt 1), L723–726.

Lobb, R.R., et al., "Small molecule antagonists of alpha4 integrins: novel drugs for asthma," *Exp. Opin, Invest. Drugs*, 1999, XP000885957, 8(7), 935–945.

Marlin, S.D. et al., "LFA–1 Immunodeficiency Disease," *J. Exp. Med.*, 1986, 164, 855–867.

Masahiko, N., Japanese Patent No. 57–080370 published May 19, 1982, "Alpha–Methylcinnamic Acid Derivative, its Preparation and Antilipemic Agent Containing The Same," *Patent Abstracts of Japan*, 1982, 1 page.

Masuda, T., *Jpn. Kodai Tokkyo Koho*, 22 pages, doc. No. 115:280022 (abstract only, 1 page); JP patent; 3–184962 dated Aug. 12, 1991.

McDowell, R.S. et al., "From Peptide to Non–Peptide. 2. The de Novo Design of Potent, Non–Peptidal Inhibitors of Platelet Aggregation Based on a Benzodiazepinedione Scaffold," *J. Am. Chem. Soc.*, 1994, 116, 5077–5083.

Miller, W.H. et al., "Structure–Activity Relationships in 3–Oxo–1,4–Benzodiazepine–2–Acetic Acid GPIIb/IIIa Antagonists. The 2–Benzazepine Series," *Bioorg. Med. Chem. Lett.*, 1996, 6(21), 2481–2486.

Mitjans, F., et al., "An anti–αv–integrin antibody that blocks integrin function inhibits the development of a human melanoma in nude mice," *J. Cell Science*, 1995, 108, 2825–2838.

Molina, P., et al., "Iminophosphorane–mediated annelation of a pyridine ring into a preformed pyridine one: synthesis of naphthyridine, pyrido [1,2–c] pyrimidine and pyrido [1,2–c] quinazoline derivatives," *Tetrahedron*, 1992, 48(22), 4601–4616.

Nagasawa, H.T. et al., "β–Substituted Cysteines as Sequestering Agents for Ethanol–Derived Acetaldehyde in Vivo," *J. Med. Chem.*, 1987, 30, 1373–1378.

Newham, P., et al., "Integrin adhesion receptors: structure, function and implications for biomedicine," *Nolecular Medicine Today*, 1996, 304–313.

Noike, Y., "Synthesis of Quinolizine Derivatives. VI. Synthesis of 3–Aminoquinolizines. (1). Synthesis of dl–3–Amino–, dl–3–epi–Amino–, and dl–3–epi–Dimethylaminoquinolizidines," *Yakugaku Zasshi*, 1959, 79(12), 1514–1518 (English summary included).

Numata, A., et al., "General synthetic method for naphthyridines and their N–oxides containing isoquinolinic nitrogen," *Synthesis*, 1999, 2, 306–311.

Ohki, S. et al., "Synthesis of quinolizine derivatives. V. Studies on Diastereoisomer of Ethyl 3–Quinolizidinecarboxylate," *Chem. Pharm. Bull.*, 1959, 7(6), 708–712.

Osborne, L., "Leukocyte Adhesion to Endothelium in Inflammation," *Cell*, 1990, 62, 3–6.

Osborn, L. et al., "Direct Expression Cloning of Vascular Cell Adhesion Molecule 1, a Cytokine–Induced Endothelial Protein that Binds to Lymphocytes," *Cell*, 1989, 59, 1203–1211.

Podolsky, D.K. et al., "Attenuation of Colitis in the Cotton–top Tamarin by Anti–α4 integrin Monoclonal Antibody," *J. Clin. Invest.*, 1993, 92, 372–380.

Pfeifer, T., et al., "Specific fragmentation of thioxo peptides facilitates the assignment of the thioxylated amino acid," *J. Mass Spectrom*, 1997, 32(10), 1064–1071, doc. No. 127:331738 (abstract only 2 pages).

Sakamoto, T., et al., "Condensed heteroaromatic ring systems. III. synthesis of naphthyridine derivatives by cyclization of ethynylpyridinecarboxamides," *Chem. Pharm. Bull.* 1985, 33(2), 626–633.

Samanen, J., et al., "Vascular indications for integrin alpha V antagonists," *Current Pharm. Design.*, 1997, 3, 545–584.

Savrda, J., "CIS–TRANS isomerism of N–ACYL derivatives of proline and its analogues, linear peptides with CIS peptide bonds," *Proc. 14$^{th}$ European Peptide Symposium*, Loffet, A. (ed.), 1976, 653–656.

Sawa, N., et al., "Preparation of 4(5)–thiocarbamoylimidazole compounds," *Jpn. Kokai Tokkyo Koho*, 33 pages, doc. No. 115:183296 (abstract only, 2 pages); JP patent.

Schultz, Von O.–E. et al., "Analogs of nuceic acid bases as antimetabolites," *Arzneimittel Forschung. Drug Res.*, 1967, 17(8), 1060–1064 (English summary included).

Schutkowski, M., et al., "Inhibition of peptidyl–prolyl cis/trans isomerase activity by substrate analog structures: thioxo tetrapeptide–4–nitroanilides," *Biochemistry*, 1995, 34(40), 13016–13026.

Shroff, H.N., et al., "Small peptide inhibitors of $\alpha_4\beta_7$ mediated MadCAM–1 adhesion to lymphocytes," *Bioorg. Med. Chem. Letts.*, 1996, 6(21), 2495–2500.

Singh, G., et al., "Prodrug approach in new drug design and development," *J. Sci. Ind. Res.*, 1996, 55, 497–510.

Sonnenberg, A., "Integrins and their ligands," *Curr. Topics Microbiol. Immunol.*, 1993, 184, 7–35.

Springer, T.A., "Adhesion receptors of the immune system," *Nature*, 1990, 346, 425–434.

Springer, T.A., "Traffic Signals for Lymphocyte Recirculation and Leukocyte Emigration: The Multistep Paradigm," *Cell*, 1994, 76, 301–314.

Srivatsa, S.S., et al., "Selective $\alpha v\beta 3$ integrin blockade potently limits neointimal hyperplasia and lumen stenosis following deep coronary arterial stent injury: evidence for the functional importance of integrin $\alpha v\beta 3$ and osteopontin expression during neointima formation," *Cariovascular Research*, 1997, 36, 408–428.

Stupack, D.G., et al., "induction of $\alpha_v\beta_3$ integrin–mediated attachment to extracellular matrix in $\beta_1$ integrin (CD29)–negative B cell lines," *Experi. Cell Research*, 1992, 203, 443–448.

Tan R., et al., "Synthesis of 2, 6–naphthyridine and some of its derivatives," *Tetrahedron Letters*, 1965, 31, 2737–2744.

Tous, G., et al., "O'–(Epoxyalkyl) tyrosines and (Epoxyalkyl) phenylalanine as irreversible inactivators of serine proteases: synthesis and inhibtion mechanism," *J. of Medicinal Chemistry*, 1990, 33(6), 1620–1634.

Tsunematsu, H. et al., "Hydrolysis of phenylthiazolones of p–guanidinophenylalanine and arginine by trypsin and related enzymes," *J. Biochem.*, 1983, 94(4), 1119–1125.

Ukai, Y. et al., "A novel synthetic inhibitor of endopeptidase–24.15," *Chemical Abstracts*, 1997, 127(2), 1 page; J. Enzym Inhib., 1996, 11(1), 39–49, reported in CAS.

Vanderslice, P. et al., "A Cyclic Hexapeptide is a Potent Antagonist of α4 Integrins," *J. Immunol.*, 1997, 158, 1710–1718.

Venturella, V.S. et al., "Substituted 1,3–Dihydro–4H–furo [3,4–d]–1,3–benzodiazepin–3–ones: Synthesis and Scope of the Method," *J. Heterocyclic Chem.*, 1969, 6(5), 671–679.

Yanagisawa, H. et al., WO 97/37970, "Preparation of phenylalkylcarboxylic acid derivatives lowering blood sugar level," *Chemical Abstracts*, 1997, Abstract 127:307307, 4 pages.

Yang, X., "A predominant role of integrin α4 in the spontaneous development of autoimmune diabetes in nonobese diabetic mice," *Proc. Natl. Acad. Sci. USA*, 1994, 91, 12604–12608.

Yednock, T.A., "Prevention of experimental autoimmune encephalomyelitis by antibodies against α4β1 integrin," *Nature*, 1992, 356, 63–66.

Whitlock, B.J. et al., "Structure and synthesis of lathyrine," *J. Org. Chem.*, 1965, 30, 115–118.

Wojciechowska, H. et al., "Preparation of 2,4–dinitrophenyl derivatives of tyrosine," *Chemical Abstracts*, 1968, 68(25), Abstract No. 114926r, 1 page; *Roc. Chem.*, 1967, 41(9), 1621–1623; reported in CAS.

WPI/Derwent No. XP–002076854, Japanese Patent No. JP 04 193 895 A (Ajinomoto, K.K.), Jul. 13, 1992, DW9234, 1 Page, Abstract Only.

WPI/Derwent No. XP–002076855, Japanese Patent No. JP 56 049 373 A (Dainippon Pharm Co. Ltd.), May 2, 1981, DW8125, 1 page, Abstract only.

Hammadi, A., et al., "Diastereoselective hydrogenation of monodehydro enkephalins controlled by chiral rhodium catalysts," *Tetrahedron: Asymmetry*, 1992, 3(10), XP002106601, 1247–1262.

Nunami, K., et al., "A novel synthesis of methyl 1,5–disubstituted imidazole–4–carboxylates using 3–bromo–2–isocyanoacrylates," *J. Org. Chem.*, 1994, 59, XP002106602, 7635–7642.

Shimohigashi, Y., et al., "Dehydro–enkephalins," *Int. J. Peptide Protein Res.*, 1983, 21, XP002106600, 202–208.

Strange, P.G., et al., "Studies of enzyme–mediated reactions. Part II. Stereochemistry of the elimination of ammonia from L–tyrosine catalysed by the enzyme from maize," *J. Chem. Soc., Perkin I*, 1972, 18, XP002106603, 2364–2372.

WPI/Derwent No. XP002106604, Japanese Patent No. JP 60 190749 (Mitsui Toatsu Chem. Inc.), Sep. 28, 1985, 1 page, Abstract only.

Rico, J.G., et al., "A highly steroselective michael addition to an αβ–unsaturated ester as the crucial step in the synthesis of a novel β–amino acid–containing fibrinogen receptor antagonist," *J. Org. Chem.*, 1993, 58, 7948–7951.

Zablocki, J.A., "Potent in vitro and in vivo inhibitors of platelet aggregation based upon the arg–gly–asp sequence of fibrinogen. (Aminobenzamidino)succinyl (ABAS) series of orally active fibrinogen receptor antagonists," *J. Med. Chem.*, 1995, 38, 2378–2394.

Baldwin, J.J., et al., "A novel naphthyridinone synthesis via enamine cyclization," *J. Org. Chem. Soc.*, 1978, 43(25), 4878–4880.

Fieser and Fieser reagents for Organic Synthesis, *John Wiley and Sons*, 1999, vols. 1–19.

Dunn, A.D., "The reaction of some brominated aminopicolines with acetic anhydride and with copper(I) cyanide," *J. Prakt. Chem.*, 1996, 338, 663–666.

Katritzky, A.R., et al. (Eds.), Comprehensive Organic Functional Group Transformations, Pergamon, 1995, vols. 1–7.

Katritzky, et al. (Eds.), Comprehensive Heterocyclic Chemistry, 1984, vols. 1–8.

Katritzky, et al. (Eds.), Comprehensive Organic Functional Group Transformations, 1994, vols. 1–11.

Larock's Comprehensive Organic Transformations, *VCH Publishers, Inc.*, 1989.

March's Advanced Organic Chemistry, *John Wiley and Sons*, 1992.

Paquette (Ed.), Encyclopedia of Reagents for Organic Synthesis, *John Wiley and Sons (eds.)*, 1995, vols. 1–8.

Rodd's Chemistry of Carbon Compounds and Supplementals, *Elsevier Sci. Pub.*, 1989, vols. 1–15.

Sheffield, D.J., "Synthesis of some 4–pyridylpyruvic acids as potential lactate dehydro–genase inhibitors," *J. Chem. Soc. Perkin. Trans.*, 1972, 1, 2506–2509.

*Tetrahedron*, 1992, 48, 4601.

Trost, et al. (Eds.), Comperhensive Organic Synthesis, *Pergamon*, 1991, vols. 1–9.

Wenkert, E., et al., "4–acylmethylnicotinonitrile derivatives," *Aust. J. Chem.*, 1972, 25, 433–438.

Wenkert, E., et al., "General methods of synthesis of indole alkaloids. VI. Syntheses of dl–corynantheidine and a camptothecin model," *J. Am. Chem. Soc.*, 1967, 89, 6741–6745.

2,7-NAPHTHYRIDINE DERIVATIVES

This invention relates to a series of 2,7-naphthyridine derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T. A., Nature, 346, 425, (1990); Springer, T. A., Cell, 76, 301, (1994)]. Specific cell surface molecules collectively referred to as cell adhesion molecules mediate many of these interactions.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 16 different integrin alpha chains and 8 different integrin beta chains have been identified [Newman, P. et al, Molecular Medicine Today, 304, (1996)]. The members of the family are typically named according to their heterodimer composition although trivial nomenclature is widespread in the field. Thus the integrin α4β1 consists of the integrin alpha 4 chain associated with the integrin beta 1 chain, but is also widely referred to as Very Late Antigen 4 or VLA-4. Not all of the potential pairings of integrin alpha and beta chains have yet been observed in nature and the integrin family has been subdivided into a number of subgroups based on the pairings that have been recognised to date [Sonnenberg, A., Current Topics in Microbiology and Immunology, 184, 7, (1993)].

The importance of integrin function in normal physiological responses is highlighted by two human deficiency diseases in which integrin function is defective. Thus in the disease termed Leukocyte Adhesion Deficiency (LAD) there is a defect in one of the families of integrins expressed on leukocytes [Marlin, S. D. et al, J. Exp. Med. 164, 855, (1986)]. Patients suffering from this disease have a reduced ability to recruit leukocytes to inflammatory sites and suffer recurrent infections, which in extreme cases may be fatal. In the case of patients suffering from the disease termed Glanzman's thrombasthenia (a defect in a member of the beta 3 integrin family) there is a defect in blood clotting (Hodivala-Dilke, K. M., J. Clin. Invest. 103, 229, (1999)].

The potential to modify integrin function in such a way as to beneficially modulate cell adhesion has been extensively investigated in animal models using specific antibodies and peptides that block various functions of these molecules [e.g. Issekutz, T. B., J. Immunol. 149, 3394, (1992); Li, Z. et al, Am. J. Physiol. 263, L723, (1992); Mitjans, F. et al, J. Cell Sci. 108, 2825, (1995); Brooks, P. C. et al, J. Clin. Invest. 96, 1815, (1995); Binns, R. M. et al, J. Immunol. 157, 4094, (1996); Hammes, H. -P. et al, Nature Medicine 2, 529, (1996); Srivata, S. et al, Cardiovascular Res. 36, 408 (1997)]. A number of monoclonal antibodies which block integrin function are currently being investigated for their therapeutic potential in human disease, and one, ReoPro, a chimeric antibody against the platelet integrin αIIbβ3 is in use as a potent anti-thrombotic agent for use in patients with cardiovascular complications following coronary angioplasty.

Integrins recognize both cell surface and extracellular matrix ligands, and ligand specificity is determined by the particular alpha-beta subunit combination of the molecule [Newman, P., ibid]. One particular integrin subgroup of interest involves the α4 chain which can pair with two different beta chains β1 and β7 [Sonnenberg, A., ibid]. The α4β1 pairing occurs on many circulating leukocytes (for example lymphocytes, monocytes, eosinophils and basophils) although it is absent or only present at low levels on circulating neutrophils. α4β1 binds to an adhesion molecule (Vascular Cell Adhesion Molecule-1 also known as VCAM-1) frequently up-regulated on endothelial cells at sites of inflammation [Osborne, L., Cell, 62, 3, (1990)]. The molecule has also been shown to bind to at least three sites in the matrix molecule fibronectin [Humphries, M. J. et al, Ciba Foundation Symposium, 189, 177, (1995)]. Based on data obtained with monoclonal antibodies in animal models it is believed that the interaction between α4β1 and ligands on other cells and the extracellular matrix plays an important role in leukocyte migration and activation [Yednock, T. A. et al, Nature, 356, 63, (1992); Podolsky, D. K. et al, J. Clin. Invest. 92, 372, (1993); Abraham, W. M. et al, J. Clin. Invest. 93, 776, (1994)].

The integrin generated by the pairing of α4 and β7 has been termed LPAM-1 [Holzmann, B. and Weissman, I. L., EMBO J. 8, 1735, (1989)]. The α4β7 pairing is expressed on certain sub-populations of T and B lymphocytes and on eosinophils [Erle, D. J. et al, J. Immunol. 153, 517 (1994)]. Like α4β1, α4β7 binds to VCAM-1 and fibronectin. In addition, α4β7 binds to an adhesion molecule believed to be involved in the homing of leukocytes to mucosal tissue termed MAdCAM-1 [Berlin, C. et al, Cell, 74, 185, (1993)]. The interaction between α4β7 and MAdCAM-1 may also be important sites of inflammation outside of mucosal tissue [Yang, X. -D. et al, PNAS, 91, 12604, (1994)].

Regions of the peptide sequence recognizeded by α4β1 and α4β7 when they bind to their ligands have been identified. α4β1 seems to recognise LDV, IDA or REDV peptide sequences in fibronectin and a QIDSP sequence in VCAM-1 [Humphries, M. J. et al, ibid] whilst α4β7 recognises a LDT sequence in MAdCAM-1 [Birskin, M. J. et al, J. Immunol. 156, 719, (1996)]. There have been several reports of inhibitors of these interactions being designed from modifications of these short peptide sequences [Cardarelli, P. M. et al, J. Biol. Chem., 269, 18668, (1994); Shorff, H. N. et al, Biorganic Med. Chem. Lett., 6, 2495, (1996); Vanderslice, P. et al, J. Immunol., 158, 1710, (1997)]. It has also been reported that a short peptide sequence derived from the α4β1 binding site in fibronectin can inhibit a contact hypersensitivity reaction in a trinitrochlorobenzene sensitised mouse [Ferguson, T. A., et al, PNAS, 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is important to be able to identify selective inhibitors of the alpha 4 subgroup.

We have now found a group of 2,7-naphthyridines which are potent and selective inhibitors of α4-integrins. Members of the group are able to inhibit α4 integrins such as α4β1 and α4β7 at concentrations at which they generally have no or minimal inhibitory action on α integrins of other subgroups. The 2,7-naphthyridines also show unexpectedly high metabolic stability when compared to other naphthyridines. The compounds are thus of use in medicine, for example in the prophylaxis and treatment of immune or inflammatory disorders as described hereinafter.

Thus according to one aspect of the invention we provide a compound of formula (1):

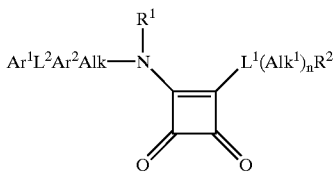

(1)

wherein

Ar$^1$ is an optionally substituted 2,7-naphthridin-1-yl group;

L$^2$ is a covalent bond or a linker atom or group;

Ar$^2$ is an optionally substituted aromatic or heteroaromatic chain;

Alk is a chain

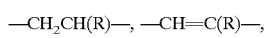

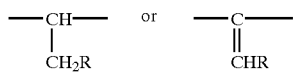

in which R is a carboxylic acid (—CO$_2$H) or a derivative or biostere thereof;

R$^1$ is a hydrogen atom or a C$_{1-6}$alkyl group;

L$^1$ is a covalent bond or a linker atom or group;

Alk$^1$ is an optionally substituted aliphatic chain;

n is zero or the integer 1;

R$^2$ is a hydrogen atom or an optionally substituted heteroaliphatic, cycloaliphatic, heterocycloaliphatic, polycycloalphatic, heteropolycyclo-aliphatic, aromatic or heteroaromatic group;

and the salts, solvates, hydrates and N-oxides thereof.

It will be appreciated that compounds of formula (1) may have one or more chiral centers, and exist as enantiomers or diastereomers. The invention is to be understood to extend to all such enantiomers, diastereomers and mixtures thereof, including racemates. Formula (1) and the formulae hereinafter are intended to represent all individual isomers and mixtures thereof, unless stated or shown otherwise.

The 2,7-naphthyridin-1-yl group represented by Ar$^1$ may be optionally substituted on any available carbon atom. One, two, three or more of the same or different substituents (R$^{16}$) may be present and each substituent may be selected for example from an atom or group -L$^3$(Alk$^2$)$_t$L$^4$(R$^4$)$_u$ in which L$^3$ and L$^4$, which may be the same or different, is each a covalent bond or a linker atom or group, t is zero or the integer 1, u is an integer 1, 2 or 3, Alk$^2$ is an aliphatic or heteroaliphatic chain and R$^4$ is a hydrogen or halogen atom or a group selected from optionally substituted C$_{1-6}$alkyl or C$_{3-8}$ cycloalkyl, —OR$^5$ [where R$^5$ is a hydrogen atom, an optionally substitued C$_{1-6}$alkyl or C$_{3-8}$ cycloalkyl group], —SR$^5$, —NR$^5$R$^6$ [where R$^6$ is as just defined for R$^5$ and may be the same or different], —NO$_2$, —CN, —CO$_2$R$^5$, —SO$_3$H, —SOR$^5$, —SO$_2$R$^5$, —SO$_3$R$^5$, —OCO$_2$ R$^5$, —CONR$^5$R$^6$, —OCONR$^5$R$^6$, —CSNR$^5$R$^6$, —COR$^5$, —OCOR$^5$, —N(R$^5$)COR$^6$, —N(R$^5$)CSR$^6$, —SO$_2$N(R$^5$)(R$^6$), —N(R$^5$)SO$_2$R$^6$, N(R$^5$)CON(R$^6$)(R$^7$) [where R$^7$ is a hydrogen atom, an optionally substituted C$_{1-6}$alkyl or C$_{3-8}$cycloalkyl group], —N(R$^5$)CSN(R$^6$)(R$^7$) or —N(R$^5$)SO$_2$N(R$^6$)(R$^7$), provided that when t is zero and each of L$^3$ and L$^4$ is a covalent bond then u is the integer 1 and R$^4$ is other than a hydrogen atom When L$^3$ and/or L$^4$ is present in these substituents as a linker atom or group it may be any divalent linking atom or group. Particular examples include —O— or —S— atoms or —C(O)—, —C(O)O—, —OC(O)—, —C(S)—, —S(O)—, —S(O)$_2$—, —N(R$^8$)— [where R$^8$ is a hydrogen atom or an optionally substituted C$_{1-6}$alkyl group], —N(R$^8$)O—, —N(R$^8$)N—, —CON(R$^8$)—, —OC(O)N(R$^8$)—, —CSN(R$^8$)—, —N(R$^8$)CO—, —N(R$^8$)C(O)O—, —N(R$^8$)CS—, —S(O)$_2$N(R$^8$)—, —N(R$^8$)S(O)$_2$—, —N(R$^8$)CON (R$^8$)—, —N(R$^8$)CSN(R$^8$)—, or —N(R$^8$)SO$_2$N(R$^8$)— groups. Where the linker group contains two R$^8$ substituents, these may be the same or different.

When R$^4$, R$^5$, R$^6$, R$^7$ and/or R$^8$ is present as a C$_{1-6}$alkyl group it may be a straight or branched C$_{1-6}$alkyl group, e.g. a C$_{1-3}$alkyl group such as a methyl or ethyl group. C$_{3-8}$cycloalkyl groups represented by R$^4$, R$^5$, R$^6$, R$^7$ and/or R$^8$ include C$_{3-6}$cycloalkyl groups e.g. cyclopropyl, cyclobutyl, cyclopentyl and cyclohexyl groups. Optional substituents which may be present on such groups include for example one, two or three substituents which may be the same or different selected from halogen atoms, for example fluorine, chlorine, bromine or iodine atoms, or hydroxy or C$_{1-6}$alkoxy e.g. methoxy or ethoxy groups.

When the groups R$^5$ and R$^6$ or R$^6$ and R$^7$ are both C$_{1-6}$alkyl groups these groups may be joined, together with the N atom to which they are attached, to form a heterocyclic ring. Such heterocyclic rings may be optionally interrupted by a further heteroatom selected from —O—, —S— or —N(R$^5$)—. Particular examples of such heterocyclic rings include piperidinyl, morpholinyl, thiomorpholinyl, pyrrolidinyl, imidazolidinyl and piperazinyl rings.

When Alk$^2$ is present as an aliphatic or heteroaliphatic chain it may be for example any divalent chain corresponding to the below-mentioned aliphatic chains described for Alk$^1$ or heteroaliphatic groups described for R2 in which one of the terminal hydrogen atoms is replaced by a bond.

Halogen atoms represented by R$^4$ in the optional Ar$^1$ substituents include fluorine, chlorine, bromine, or iodine atoms.

Examples of the substituents represented by -L$^3$(Alk$^2$)$_t$L$^4$ (R$^4$)$_u$ when present in Ar$^1$ groups in compounds of the invention include atoms or groups -L$^3$Alk$^2$L$^4$R$^4$, -L$^3$Alk$^2$R$^4$, -L$^3$R$^4$, -R4 and -Alk$^2$R$^4$ wherein L$^3$, AlK$^2$, L$^4$ and R$^4$ are as defined above. Particular examples of such substituents include -L$^3$CH$_2$L$^4$R$^4$, -L$^3$CH(CH$_3$)L$^4$R$^4$, -L$^3$CH(CH$_2$)$_2$L$^4$R$^4$, -L$^3$CH$_2$R$^4$, -L$^3$CH(CH$_3$)R$^4$, -L$^3$(CH$_2$)$_2$R$^4$, —CH$_2$R$^4$, —CH(CH$_3$)R$^4$, —(CH$_2$)$_2$R$^4$ and —R$^4$ groups.

Thus the 2,7-naphthyridin-1-yl group in compounds of the invention may be optionally substituted for example by one, two, three or more halogen atoms, e.g. fluorine, chlorine, bromine or iodine atoms, and/or C$_{1-6}$alkyl, e.g. methyl, ethyl, n-propyl, i-propyl, n-butyl or t-butyl, C$_{3-8}$cycloalkyl, e.g. cyclopropyl, cyclobutyl, cyclopentyl or cyclohexyl, C$_{1-6}$hydroxyalkyl, e.g. hydroxymethyl, hydroxyethyl or —C(OH)(CF$_3$)$_2$, carboxyC$_{1-6}$alkyl, e.g. carboxyethyl, C$_{1-6}$alkylthio e.g. methylthio or ethylthio, carboxyC$_{1-6}$alkylthio, e.g. carboxymethylthio, 2-carboxyethylthio or 3-carboxypropylthio, C$_{1-6}$alkoxy, e.g. methoxy or ethoxy, hydroxyC$_{1-6}$alkoxy, e.g. 2-hydroxyethoxy, haloC$_{1-6}$alkyl, e.g. —CF$_3$, —CHF$_2$, CH$_2$F, haloC$_{1-6}$alkoxy, e.g. —OCF$_3$, —OCHF$_2$, —OCH$_2$F, C$_{1-6}$alkylamino, e.g. methylamino or ethylamino, amino (—NH$_2$), aminoC$_{1-6}$alkyl, e.g. aminomethyl or aminoethyl, C$_{1-6}$dialkylamino, e.g. dimethylamino or diethylamino, C$_{1-6}$alkylaminoC$_{1-6}$alkyl, e.g. ethylaminoethyl, C$_{1-6}$ dialkylaminoC$_{1-6}$alkyl, e.g. diethylaminoethyl, aminoC$_{1-6}$alkoxy, e.g. aminoethoxy, C$_{1-6}$alkylaminoC$_{1-6}$alkoxy, e.g.

methylaminoethoxy, $C_{1-6}$dialkylamino$C_{1-6}$alkoxy, e.g. dimethylamino-ethoxy, diethylaminoethoxy, isopropylaminoethoxy, or dimethylamino-propoxy, nitro, cyano, amidino, hydroxyl (—OH), formyl [HC(O)—], carboxyl (—$CO_2$H), —$CO_2$Alk$^3$ [where Alk$^3$ is as defined below for Alk$^7$], $C_{1-6}$ alkanoyl e.g. acetyl, thiol (—SH), thio$C_{1-6}$alkyl, e.g. thiomethyl or thioethyl, sulphonyl (—$SO_3$H), —$SO_3$Alk$^3$, $C_{1-6}$alkylsulphinyl, e.g. methylsulphinyl, $C_{1-6}$alkylsulphonyl, e.g. methylsulphonyl, aminosulphonyl (—$SO_2NH_2$), $C_{1-6}$ alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, aminosulphonylamino (—$NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino groups.

$L^2$ when present as part of the group $R^1$ in compounds of the invention may be a linker atom or group $L^{2a}$ or a linker -Alk$^a$($L^{2a}$)$_y$-, where Alk$^a$ is an optionally substituted aliphatic or heteroaliphatic chain as previously defined for Alk$^2$, $L^{2a}$ is a covalent bond or a linker atom or group as described above for $L^3$ and $L^4$, and y is zero or the integer 1.

Optionally substituted aromatic or heteroaromatic groups represented by Ar$^2$ include those aromatic or heteroaromatic groups described hereinafter in relation to R$^2$ aromatic or heteroaromatic groups respectively. The optional substituents which may be present on these groups include one, two, three or four optional substituents (R$^{17a}$, R$^{17b}$, R$^{17c}$, and R$^{17d}$) where such substituents include those R$^{16}$ optional substituents as described hereinbefore.

It will be appreciated that when the optional substituents R$^{17a}$, R$^{17b}$, R$^{17c}$ and R$^{17d}$ are absent then the aromatic or heteroaromatic ring Ar$^2$ is substituted by hydrogen atoms in place of those substituents.

When the group R is present in compounds of the invention as a derivative of a carboxylic acid it may be for example a carboxylic acid ester or amide. Particular esters and amides include —$CO_2$Alk$^7$ and —CONR$^5$R$^6$ groups as defined herein. When R is a biostere of a carboxylic acid it may be for example a tetrazole or other acid such as phosphonic acid, phosphinic acid, sulphonic acid, sulphinic acid or boronic acid or an acylsulphonamide group.

Esters (—$CO_2$Alk$^7$) and amide (—CONR$^5$R$^6$) derivatives of the carboxylic acid group (—$CO_2$H) in compounds of formula (1) may advantageously be used as prodrugs of the active compound. Such prodrugs are compounds which undergo biotransformation to the corresponding carboxylic acid prior to exhibiting their pharmacological effects and the invention particularly extends to produgs of the acids of formula (1). Such prodrugs are well known in the art, see for example International Patent Application No. WO00/23419, Bodor, N. (Alfred Benzon Symposium, 1982, 17, 156–177), Singh, G. et al (J. Sci. Ind. Res., 1996, 55, 497–510) and Bundgaard, H., (Design of Prodrugs, 1985, Elsevier, Amsterdam).

Esterified carboxyl groups represented by the group —$CO_2$Alk$^7$ wherein Alk$^7$ include groups is a straight or branched optionally substituted $C_{1-8}$alkyl group such as a methyl, ethyl, n-propyl, i-propyl, n-butyl, i-butyl, s-butyl or t-butyl group, an optionally substituted $C_{2-8}$alkenyl group such as a propenyl e.g. 2-propenyl or butenyl e.g. 2-butenyl or 3-butenyl group, an optionally substituted $C_{2-8}$alkynyl group such as a ethynyl, propynyl e.g. 2-propynyl or butynyl e.g. 2-butynyl or 3-butynyl group, an optionally substituted $C_{3-8}$cycloalkyl group such as a cyclopropyl, cyclobutyl, cyclopentyl, cyclohexyl or cycloheptyl group; an optionally substituted $C_{3-8}$cycloalkyl$C_{1-8}$alkyl group such as a cyclopentylmethyl, cyclohexylmethyl or cyclohexylethyl group; an optionally substituted $C_{3-8}$heterocycloalkyl$C_{1-6}$alkyl group such as a morpholinyl-N-ethyl, thiomorpholinyl-N-methyl, pyrrolidinyl-N-ethyl, pyrrolidinyl-N-propyl, piperidinyl-N-ethyl, pyrazolidinyl-N-methyl or piperazinyl-N-ethyl group; an optionally substituted $C_{1-6}$alkyloxy$C_{1-6}$alkyl group such as a methyloxyethyl or propyloxyethyl group; an optionally substituted $C_{1-6}$alkylthio$C_{1-6}$alkyl group such as an ethylthioethyl group; an optionally substituted $C_{1-6}$alkylsulfinyl$C_{1-6}$alkyl group such as an methylsulfinylethyl group; an optionally substituted $C_{1-6}$alkylsulfonyl$C_{1-6}$alkyl group such as an methylsulfonylmethyl group; an optionally substituted $C_{3-8}$cycloalkyloxy$C_{1-6}$alkyl group such as a cyclohexyloxymethyl group; an optionally substituted $C_{3-8}$cycloalkylthio$C_{1-6}$alkyl group such as a cyclopentylthiomethyl group; an optionally substituted $C_{3-8}$cycloalkylsulfinyl$C_{1-6}$alkyl group such as a cyclopentylsulfinylmethyl group; an optionally substituted $C_{3-8}$cycloalkylsulfonyl$C_{1-6}$alkyl group such as a cyclopentylsulfonylmethyl group; an optionally substituted $C_{1-6}$alkyloxycarbonyl$C_{1-6}$alkyl group such as isobutoxycarbonylpropyl group; an optionally substituted $C_{1-6}$alkyloxycarbonyl$C_{1-6}$alkenyl group such as isobutoxycarbonylpentenyl group; an optionally substituted $C_{1-6}$alkyloxycarbonyloxy$C_{1-6}$alkyl group such as an isopropoxycarbonyloxyethyl e.g. a 1-(isopropoxycarbonyloxy)ethyl, 2-(isopropoxycarbonyloxy)ethyl or ethyloxycarbonyloxymethyl group; an optionally substituted $C_{1-6}$alkyloxycarbonyloxy$C_{1-6}$alkenyl group such as a isopropoxycarbonyloxybutenyl group, an optionally substituted $C_{3-8}$cycloalkyloxycarbonyloxy$C_{1-6}$alkyl group such as a cyclohexyloxycarbonyloxyethyl, e.g. a 2-(cyclohexyloxycarbonyloxy)ethyl group, an optionally substituted N-di-$C_{1-8}$alkylamino$C_{1-8}$alkyl group such as a N-dimethylaminoethyl or N-diethylaminoethyl group; an optionally substituted N-$C_{6-12}$aryl-N-$C_{1-6}$alkylamino$C_{1-6}$alkyl group such as a N-phenyl-N-methylaminomethyl group; an optionally substituted N-di-$C_{1-8}$alkylcarbamoyl$C_{1-8}$alkyl group such as a N-diethylcarbamoylmethyl group; an optionally substituted $C_{6-10}$aryl$C_{1-6}$alkyl group such as an optionally substituted benzyl, phenylethyl, phenylpropyl, 1-naphthylmethyl or 2-naphthylmethyl group; a $C_{6-10}$aryl group such as an optionally substituted phenyl, 1-naphthyl or 2-naphthyl group; a $C_{6-10}$aryloxy$C_{1-8}$alkyl group such as an optionally substituted phenyloxymethyl, phenyloxyethyl, 1-naphthyloxymethyl, or 2-naphthyloxymethyl group; a $C_{6-12}$arylthio$C_{1-8}$alkyl group such as an optionally substituted phenylthioethyl group; a $C_{6-12}$arylsulfinyl$C_{1-8}$alkyl group such as an optionally substituted phenylsulfinylmethyl group; a $C_{6-12}$arylsulfonyl$C_{12-8}$alkyl group such as an optionally substituted phenylsulfonylmethyl group; an optionally substituted $C_{1-8}$alkanoyloxy$C_{1-8}$alkyl group, such as a acetoxymethyl, ethoxycarbonyloxyethyl, pivaloyloxymethyl, propionyloxyethyl or propionyloxypropyl group; an optionally substituted $C_{4-8}$imido$C_{1-8}$alkyl group such as a succinimidomethyl or phthalamidoethyl group; a $C_{6-12}$aroyloxy$C_{1-8}$alkyl group such as an optionally substituted benzoyloxyethyl or benzoyloxypropyl group or a triglyceride such as a 2-substituted triglyceride e.g. a 1,3 -di-$C_{1-8}$alkylglycerol-2-yl group such as a 1,3-diheptylglycerol-2-yl group.

Optional substituents present on the $Alk^7$ group include $R^{13a}$ substituents described above.

It will be appreciated that in the forgoing list of $Alk^7$ groups the point of attachment to the remainder of the compound of formula (1) is via the last described part of the $Alk^7$ group. Thus, for example a methoxyethyl group would be attached by the ethyl group, whilst a morpholinyl-N-ethyl group would be attached via the N-ethyl group.

It will be further appreciated that in the forgoing list of $Alk^7$ groups, where not specifically mentioned, alkyl groups may be replaced by alkenyl or alkynyl groups where such groups are as defined hereinafter for $Alk^1$. Additionally these alkyl, alkenyl or alkynyl groups may optionally be interrupted by one, two or three linker atoms or groups where such linker atoms and groups are as previously defined for $L^3$.

When the group $R^2$ is present in compounds of the invention as a $C_{1-6}$alkyl group it may be for example a straight or branched $C_{1-6}$alkyl group, e.g. a $C_{1-3}$alkyl group such as a methyl or ethyl group.

The linker atom or group represented by $L^1$ in compounds of formula (1) may be any linker atom or group as described above for the linker atom or group $L^3$.

When the group $Alk^1$ is present in compounds of formula (1) as an optionally substituted aliphatic chain it may be an optionally substituted $C_{1-10}$ aliphatic chain. Particular examples include optionally substituted straight or branched chain $C_{1-6}$ alkylene, $C_{2-6}$ alkenylene, or $C_{2-6}$ alkynylene chains.

Particular examples of aliphatic chains represented by $Alk^1$ include optionally substituted —$CH_2$—, —$(CH_2)_2$—, —$CH(CH_3)CH_2$—, —$(CH_2)_2CH_2$—, —$(CH_2)_3CH_2$—, —$CH(CH_3)(CH_2)_2$—, —$CH_2CH(CH_3)CH_2$—, —$C(CH_3)_2CH_2$—, —$CH_2C(CH_3)_2CH_2$—, —$(CH_2)_2C(CH_3)_2CH_2$—, —$(CH_2)_4CH_2$—, —$(CH_2)_5CH_2$—, —CHCH—, —CHCHCH$_2$—, —$CH_2$CHCH—, —CHCHCH$_2CH_2$—, —$CH_2$CHCHCH$_2$—, —$(CH_2)_2$CHCH—, —CC—, —CCCH$_2$—, —$CH_2$CC—, —CCCH$_2CH_2$—, —$CH_2$CCCH$_2$— or —$(CH_2)_2$CCH— groups.

Heteroaliphatic groups represented by the group $R^2$ in the compounds of formula (1) include the aliphatic chains just described for $Alk^1$ but with each containing a terminal hydrogen atom and additionally containing one, two, three or four heteroatoms or heteroatom-containing groups. Particular heteroatoms or groups include atoms or groups $L^5$ where $L^5$ is as defined above for $L^3$ when $L^3$ is a linker atom or group. Each $L^5$ atom or group may interrupt the aliphatic group, or may be positioned at its terminal carbon atom to connect the group to an adjoining atom or group. Particular examples include optionally substituted -$L^5CH_3$, —$CH_2L^5CH_3$, -$L^5CH_2CH_3$, —$CH_2L^5CH_2CH_3$, —$(CH_2)_2L^5CH_3$, —$(CH_2)_3L^5CH_3$, -$L^5(CH_2)_3$, and —$(CH_2)_2L^5CH_2CH_3$ groups.

The optional substituents which may be present on aliphatic or heteroaliphatic chains represented by $Alk^1$ and $R^2$ respectively include one, two, three or more substituents where each substituent may be the same or different and is selected from halogen atoms, e.g. fluorine, chlorine, bromine or iodine atoms, or —OH, —$CO_2H$, —$CO_2R^9$, where $R^9$ is an optionally substituted straight or branched $C_{1-6}$alkyl group as defined above for $R^4$, —$CONHR^9$, —$CON(R^9)_2$, —$COCH_3$, $C_{1-6}$alkoxy, e.g. methoxy or ethoxy, thiol, —$S(O)R^9$, —$S(O)_2R^9$, $C_{1-6}$alkylthio e.g. methylthio or ethylthio, amino or substituted amino groups. Substituted amino groups include —$NHR^9$ and —$N(R^9)_2$ groups . Where two $R^9$ groups are present in any of the above substituents these may be the same or different.

Optionally substituted cycloaliphatic groups represented by the group $R^2$ in compounds of the invention include optionally substituted $C_{3-10}$ cycloaliphatic groups. Particular examples include optionally substituted $C_{3-10}$ cycloalkyl, e.g. $C_{3-7}$ cycloalkyl or $C_{3-10}$ cycloalkenyl, e.g. $C_{3-7}$ cycloalkenyl groups.

Optionally substituted heterocycloaliphatic groups represented by the group $R^2$ include optionally substituted $C_{3-10}$heterocycloaliphatic groups. Particular examples include optionally substituted $C_{3-10}$heterocycloalkyl, e.g. $C_{3-7}$ heterocycloalkyl, or $C_{3-10}$heterocycloalkenyl, e.g. $C_{3-7}$ hetercycloalkenyl groups, each of said groups containing one, two, three or four heteroatoms or heteroatom-containing groups $L^5$ as defined above.

Optionally substituted polycycloaliphatic groups represented by the group $R^2$ include optionally substitued $C_{7-10}$ bi- or tricycloalkyl or $C_{7-10}$bi- or tricycloalkenyl groups. Optionally substituted heteropolycycloaliphatic groups represented by the group $R^2$ include the optionally substituted polycycloalkyl groups just described, but with each group additionally containing one, two, three or four $L^5$ atoms or groups.

Particular examples of cycloaliphatic, polycycloaliphatic, heterocycloaliphatic and heterpolyocycloaliphatic groups represented by the group $R^2$ include optionally substituted cyclopropyl, cyclobutyl, cyclopentyl, cyclohexyl, cycloheptyl, 2-cyclobuten-1-yl, 2-cyclopenten-1-yl, 3 -cyclopenten-1-yl, adamantyl, norbornyl, norbornenyl, tetrahydrofuranyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, homopiperidinyl (azepanyl), heptamethyleneiminyl, piperidinone, 1,4-dioxanyl, morpholinyl, morpholinone, 1,4-dithianyl, thiomorpholinyl, piperazinyl, homopiperazinyl, 1,3,5-trithianyl, oxazinyl, e.g. 2H-1,3-, 6H-1,3-, 2H-1,2- or 4H-1,4 -oxazinyl, 1,2,5-oxathiazinyl, isoxazinyl, e.g. o- or p-isoxazinyl, oxathiazinyl, e.g. 1,2,5 or 1,2,6-oxathiazinyl, or 1,3,5,-oxadiazinyl groups.

The optional substituents which may be present on the cycloaliphatic, polycycloaliphatic, heterocycloaliphatic or polyheterocycloaliphatic groups represented by the group $R^2$ include one, two, three or more substituents each selected from halogen atoms, e.g. fluorine, chlorine, bromine or iodine atoms, or $C_{1-6}$alkyl, e.g. methyl or ethyl, halo$C_{1-6}$alkyl, e.g. halomethyl or haloethyl such as difluoromethyl or trifluoromethyl, optionally substituted by hydroxyl, e.g. —C(OH)(CF$_3$)$_2$, $C_{1-6}$alkoxy, e.g. methoxy or ethoxy, halo$C_{1-6}$alkoxy, e.g. halomethoxy or haloethoxy such as difluoromethoxy or trifluoromethoxy, thiol, $C_{1-6}$alkylthio e.g. methylthio or ethylthio, or -(Alk$^4$)$_v$R$^{10}$ groups in which Alk$^4$ is a straight or branched $C_{1-3}$alkylene chain, v is zero or an integer 1 and $R^{10}$ is a —OH, —SH, —N(R$^{11}$)$_2$, (in which $R^{11}$ is an atom or group as defined herein for $R^8$)—CN, —CO$_2$R$^{11}$, —NO$_2$, —CON(R$^{11}$)$_2$, —CSN(R$^{11}$)$_2$, —COR$^{11}$, —CSN(R$^{11}$)$_2$, —N(R$^{11}$)COR$^{11}$, —N(R$^{11}$)CSR$^{11}$, —SO$_2$N(R$^{11}$)$_2$, —N(R$^{11}$)SO$_2$R$^{11}$, —N(R$^{11}$)CON(R$^{11}$)$_2$, —N(R$^{11}$)CSN(R$^{11}$), N(R$^{11}$)SO$_2$N(R$^{11}$)$_2$ or optionally substituted phenyl group. Where two R$^{11}$ atoms or groups are present in these substituents these may be the same or different. Optionally substituted phenyl groups include phenyl substituted by one, two or three of the R$^{13}$ groups described below.

Particular examples of Alk$^4$ chains include —CH$_2$—, —CH$_2$CH$_2$—, —CH$_2$CH$_2$CH$_2$— and —CH(CH$_3$)CH$_2$— chains.

Additionally, when the group $R^2$ is a heterocycloaliphatic group containing one or more nitrogen atoms each nitrogen atom may be optionally substituted by a group -(L$^6$)$_p$(Alk$^5$)$_q$R$^{12}$ in which L$^6$ is —C(O)—, —C(O)O—, —C(S)—, —S(O)$_2$—, —CON(R$^{11}$)—, —CSN(R$^{11}$)— or SO$_2$N(R$^{11}$)—; p is zero or an integer 1; Alk$^5$ is an optionally substituted aliphatic or heteroaliphatic chain; q is zero or an integer 1; and $R^{12}$ is a hydrogen atom or an optionally substituted cycloaliphatic, heterocycloaliphatic, polycycloaliphatic, polyheterocycloaliphatic, aromatic or heteroaromatic group.

Optionally substituted aliphatic or heteroaliphatic chains represented by Alk$^5$ include those optionally substituted chains described above for Alk$^2$.

Cycloaliphatic, heterocycloaliphatic, polycycloaliphatic or polyheterocyclo-aliphatic groups represented by R$^{12}$ include those groups just described for the group R$^2$. Optional substituents which may be present on these groups include those described above in relation to Alk$^1$ and R$^2$ aliphatic and heteroaliphatic chains.

Optionally substituted aromatic groups represented by R$^2$ when present in the group R$^1$ include for example optionally substituted monocyclic or bicyclic fused ring $C_{6-12}$ aromatic groups, such as phenyl, 1- or 2-naphthyl, 1- or 2-tetrahydronaphthyl, indanyl or indenyl groups.

Optionally substituted heteroaromatic groups represented by the group R$^2$ include for example optionally substituted $C_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused-ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N-$C_{1-6}$alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, [2,3-dihydro]benzothienyl, benzothienyl, benzotriazolyl, indolyl, isoindolyl, benzimidazolyl, imidazo[1,2-a]pyridyl, benzothiazolyl, benzoxazolyl, benzopyranyl, [3,4-dihydro]benzopyranyl, quinazolinyl, quinoxalinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Optional substituents which may be present on the aromatic or heteroaromatic groups represented by the group R$^2$ include one, two, three or more substituents, each selected from an atom or group R$^{13}$ in which R$^{13}$ is —R$^{13a}$ or -Alk$^6$(R$^{13a}$)$_m$, where R$^{13a}$ is a halogen atom, or an amino (—NH$_2$), substituted amino, nitro, cyano, amidino, hydroxyl (—OH), substituted hydroxyl, formyl, carboxyl (—CO$_2$H), esterified carboxyl, thiol (—SH), substituted thiol, —COR$^{14}$ [where R$^{14}$ is an -Alk$^6$(R$^{13a}$)$_m$, cycloaliphatic, heterocycloaliphatic, aryl or heteroaryl group], —CSR$^{14}$, —SO$_3$H, —SOR$^{14}$, —SO$_2$R$^{14}$, —SO$_3$R$^{14}$, —SO$_2$NH$_2$, —SO$_2$NHR$^{14}$, —SO$_2$N(R$^{14}$)$_2$, —CONH$_2$, —CSNH$_2$, —CONHR$^{14}$, —CSNHR$^{14}$, —CON[R$^{14}$]$_2$, —CSN(R$^{14}$)$_2$, —N(R$^{11}$)SO$_2$R$^{14}$, —N(SO$_2$ R$^{14}$)$_2$, —NH(R$^{11}$)SO$_2$NH$_2$, —N(R$^{11}$)SO$_2$NHR$^{14}$, —N(R$^{11}$)SO$_2$N(R$^{14}$)$_2$, —N(R$^{11}$)COR$^{14}$, —N(R$^{11}$)CONH$_2$, —N(R$^{11}$)CONHR$^{14}$, —N(R$^{11}$)CON(R$^{14}$)$_2$, —N(R$^{11}$)CSNH$_2$, —N(R$^{11}$)CSNHR$^{14}$, —N(R$^{11}$)CSN(R$^{14}$)$_2$, —N(R$^{11}$)CSR$^{14}$, —N(R$^{11}$)C(O)OR$^{14}$, —SO$_2$NHet$^1$ [where -NHet$^1$ is an optionally substituted $C_{5-7}$cyclicamino group optionally containing one or more other —O— or —S— atoms or —N(R$^{11}$)—, —C(O)—, —C(S)—, S(O) or —S(O)$_2$ groups], —CONHet$^1$, —CSNHet$^1$, —N(R$^{11}$)SO$_2$NHet$^1$, —N(R$^{11}$)CONHet$^1$, —N(R$^{11}$)CSNHet$^1$, —SO$_2$N(R$^{11}$)Het$^2$ [where Het$^2$ is an optionally substituted monocyclic $C_{5-7}$carbocyclic group optionally containing one or more —O— or —S— atoms or —N(R$^{11}$)—, —C(O)— or —C(S)— groups], -Het$^2$, —CON(R$^{11}$)Het$^2$, —CSN(R$^{11}$)Het$^2$, —N(R$^{11}$)CON(R$^{11}$)Het$^2$, —N(R$^{11}$)CSN(R$^{11}$)Het$^2$, cycloaliphatic, heterocycloaliphatic, aryl or heteroaryl group; Alk$^6$ is a straight or branched $C_{1-6}$alkylene, $C_{2-6}$alkenylene or $C_{2-6}$alkynylene chain, optionally interrupted by one, two or three —O— or —S— atoms or —S(O)$_n$ [where n is an integer 1 or 2] or —N(R$^{15}$)— groups [where R$^{15}$ is a hydrogen atom or $C_{1-6}$alkyl, e.g. methyl or ethyl group]; and m is zero or an integer 1, 2 or 3. It will be appreciated that when two R$^{11}$ or R$^{14}$ groups are present in one of the above substituents, the R$^{11}$ or R$^{14}$ groups may be the same or different.

When in the group -Alk$^6$(R$^{13a}$)$_m$ m is an integer 1, 2 or 3, it is to be understood that the substituent or substituents R$^{13a}$ may be present on any suitable carbon atom in -Alk$^6$. Where more than one R$^{13a}$ substituent is present these may be the same or different and may be present on the same or different atom in -Alk$^6$. Clearly, when m is zero and no substituent R$^{13a}$ is present the alkylene, alkenylene or alkynylene chain represented by Alk$^6$ becomes an alkyl, alkenyl or alkynyl group.

When R$^{13a}$ is a substituted amino group it may be for example a group —NHR$^{14}$ [where R$^{14}$ is as defined above] or a group —N(R$^{14}$)$_2$ wherein each R$^{14}$ group is the same or different.

When $R^{13a}$ is a halogen atom it may be for example a fluorine, chlorine, bromine, or iodine atom.

When $R^{13a}$ is a substituted hydroxyl or substituted thiol group it may be for example a group —$OR^{14}$ or a —$SR^{14}$ or —SC(=NH)NH$_2$ group respectively.

Esterified carboxyl groups represented by the group $R^{13a}$ include groups of formula —CO$_2$Alk$^7$ wherein Alk$^7$ is a group as defined hereinbefore.

Esterified carboxyl groups represented by the group $R^{13a}$ include groups of formula —CO$_2$Alk$^7$ wherein Alk$^7$ is a group as defined hereinbefore.

When Alk$^6$ is present in or as a substituent it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^9$)— groups.

Cycloaliphatic or heterocycloaliphatic groups represented by the groups $R^{13a}$ or $R^{14}$ include those optionally substituted $C_{3-10}$cycloaliphatic or $C_{3-10}$ heterocycloaliphatic groups described above for $R^2$.

Aryl or heteroaryl groups represented by the groups $R^{13a}$ or $R^{14}$ include mono- or bicyclic optionally substituted $C_{6-12}$ aromatic or $C_{1-9}$ heteroaromatic groups as described above for the group $R^2$. The aromatic and heteroaromatic groups may be attached to the remainder of the compound of formula (1) by any carbon or hetero e.g. nitrogen atom as appropriate.

When -NHet$^1$ or -Het$^2$ forms part of a substituent $R^{13}$ each may be for example an optionally substituted pyrrolidinyl, pyrazolidinyl, piperazinyl, morpholinyl, thiomorpholinyl, piperidinyl or thiazolidinyl group. Additionally Het$^2$ may represent for example, an optionally substituted cyclopentyl or cyclohexyl group. Optional substituents which may be present on -NHet$^1$ or -Het$^2$ include those $R^7$ substituents described above.

Particularly useful atoms or groups represented by $R^{13}$ include fluorine, chlorine, bromine or iodine atoms, or $C_{1-6}$alkyl, e.g. methyl, ethyl, n-propyl, i-propyl, n-butyl or t-butyl, optionally substituted phenyl, pyridyl, pyrimidinyl, pyrrolyl, furyl, thiazolyl, thienyl, morpholinyl, thiomorpholinyl, piperazinyl, e.g. t-butyloxycarbonylpiperazinyl, pyrrolidinyl, dioxolanyl, dioxanyl, oxazolidinyl, thiazolidinyl, imidazolidinyl or piperidinyl, $C_{1-6}$hydroxyalkyl, e.g. hydroxymethyl or hydroxyethyl, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, optionally substituted phenoxy, pyridyloxy, thiazolyoxy, phenylthio or pyridylthio, $C_{4-7}$cycloalkyl, e.g. cyclobutyl, cyclopentyl, $C_{5-7}$cycloalkoxy, e.g. cyclopentyloxy, halo$C_{1-6}$alkyl, e.g. trifluoromethyl, halo$C_{1-6}$alkoxy, e.g. trifluoromethoxy, $C_{1-6}$alkylamino, e.g. methylamino, ethylamino or propylamino, C6-12arylC1-6alkylamino, e.g. benzylamino, 4-fluorobenzylamino or 4-hydroxyphenylethylamino, amino (—NH$_2$), amino$C_{1-6}$alkyl, e.g. aminomethyl or aminoethyl, $C_{1-6}$dialkylamino, e.g. dimethylamino or diethylamino, aminoC1-6alkylamino, e.g. aminoethylamino or aminopropylamino, optionally substituted Het$^1$NC$_{1-6}$alkylamino, e.g. 3-morpholinopropylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, diisopropylaminethoxy, or dimethylaminopropoxy, hydroxy$C_{1-6}$alkylamino, e.g. 2-hydroxyethylamino, 3-hydroxypropylamino or 3-hydroxybutylamino, imido, such as phthalimido or naphthalimido, e.g. 1,8-naphthalimido, nitro, cyano, amidino, hydroxyl (—OH), formyl [HC(O)—], carboxyl (—CO$_2$H), —CO$_2$Alk$^7$ [where Alk$^7$ is as defined above], $C_{1-6}$alkanoyl e.g. acetyl, propyryl or butyryl, optionally substituted benzoyl, thiol (—SH), thio$C_{1-6}$alkyl, e.g. thiomethyl or thioethyl, —SC(=NH)NH$_2$, sulphonyl (—SO$_3$H), —SO$_3$Alk$^7$, $C_{1-6}$alkylsulphinyl, e.g. methylsulphinyl, ethylsulphinyl or propylsulphinyl, $C_{1-6}$alkylsulphonyl, e.g. methylsulphonyl, ethylsulphonyl or propylsulphonyl, aminosulphonyl (—SO$_2$NH$_2$), $C_{1-6}$alkylaminosulphonyl, e.g. methylaminosulphonyl, ethylaminosulphonyl or propylaminosulphonyl $C_{1-6}$dialkylaminosulphonyl, e.g. dimethylaminosulphonyl or diethylaminosulphonyl, phenylaminosulphonyl, carboxamido (—CONH$_2$), $C_{1-6}$alkylaminocarbonyl, e.g. methylaminocarbonyl, ethylaminocarbonyl or propylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$alkylamino$C_{1-6}$alkylaminocarbonyl, e.g. methylaminoethylaminocarbonyl, $C_{1-6}$dialkyl-amino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethyl-amino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, —CONHC(=NH)NH$_2$, $C_{1-6}$alkyl-sulphonylamino, e.g. methylsulphonylamino or ethylsulphonylamino, halo$C_{1-6}$alkylsulphonylamino, e.g. trifluoromethylsulphonylamino, $C_{1-6}$ dialkylsulphonylamino, e.g. dimethylsulphonylamino or diethylsulphonylamino, optionally substituted phenylsulphonylamino, aminosulphonylamino (—NHSO$_2$NH$_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, optionally substituted morpholinesulphonylamino or morpholinesulphonyl$C_{1-6}$alkylamino, optionally substituted phenylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylamino$C_{1-6}$alkyl e.g. benzyloxycarbonylaminoethyl, thiobenzyl, pyridylmethylthio or thiazolylmethylthio groups.

Where desired, two $R^{13}$ substituents may be linked together to form a cyclic group such as a cyclic ether, e.g. a $C_{1-6}$alkylenedioxy group such as methylenedioxy or ethylenedioxy.

It will be appreciated that where two or more $R^{13}$ substituents are present, these need not necessarily be the same atoms and/or groups. In general, the substituent(s) may be present at any available ring position in the aromatic or heteroaromatic group represented by $R^2$.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

The group $Ar^2$ in compounds of formula (1) is preferably an optionally substituted phenylene group.

A particularly useful group of compounds according to the invention has the formula (2):

(2)

wherein $R^{16}$ is a hydrogen atom or an atom or group $-L^3(Alk^2)_t L^4(R^4)_u$ in which $L^3$, $Alk^2$, $t$, $L^4$, $R^4$, and $u$ are as previously generally and particularly defined;
$R^{17a}$ and $R^{17b}$ is each a hydrogen atom or an optional substituent as defined for formula (1);
$L^1$, $L^2$, $Ar^2$, Alk, $R^1$, $Alk^1$, n and $R^2$ are as defined for formula (1);
g is zero or the integer 1, 2, 3,4 or 5;
and the salts, solvates, hydrates and N-oxides thereof.

Particularly useful $R^{16}$ substituents when present in compounds of formula (2) include halogen atoms, especially fluorine or chlorine atoms, or straight or branched $C_{1-6}$alkyl especially methyl, ethyl, propyl or isopropyl, $C_{3-8}$cycloalkyl especially cyclopropyl, cyclobutyl, cyclopentyl or cyclohexyl, halo$C_{1-6}$alkyl especially halomethyl, most especially —$CF_3$ or —$CHF_2$ $C_{1-6}$alkoxy especially methoxy or ethoxy, halo$C_{1-6}$alkoxy especially halomethoxy, most especially —$OCF_3$, or —$OCHF_2$, —$SR^5$ especially methylthio or ethylthio, —CN, —$CO_2Alk^3$, especially —$CO_2CH_3$, —$NO_2$, amino (—$NH_2$), substituted amino (—$NR^5R^6$), and —$N(R^5)COCH_3$, especially —$NHCOCH_3$ and —$COR^5$, especially —$COCH_3$ groups.

Particularly useful $R^{17a}$ and $R^{17b}$ substituents when present in compounds of formula (2) include those particularly useful substituents as just described for $R^{16}$.

In one preferred class of compounds of formula (2) g is zero.

In another preferred class of compounds of formula (2) g is the integer 1 or 2.

Alk in compounds of the invention is preferably:

$$-CH-$$
$$|$$
$$CH_2R$$

or, especially, —$CH_2CH(R)$—.

In one preferred class of compounds of formulae (1) and (2) R is a —$CO_2H$ group.

In another preferred class of compounds of formulae (1) and (2) R is an esterified carboxyl group of formula —$CO_2Alk^7$. In this class of compound $Alk^7$ is preferably a $C_{1-8}$alkyl group, especially a methyl, ethyl, propyl, i-propyl, butyl or pentyl group, an optionally substituted $C_{3-8}$cycloalkyl group, especially a cyclopropyl, cyclobutyl, cyclopentyl, cyclohexyl or cycloheptyl group, an optionally substituted $C_{6-10}$aryl group, especially a phenyl group, an optionally substituted $C_{6-10}$aryl$C_{1-6}$alkyl group, especially a benzyl group, an optionally substituted $C_{3-8}$heterocycloalkyl$C_{1-6}$alkyl group, especially a morpholinyl-N-ethyl group, an optionally substituted N-di-$C_{1-8}$alkylamino$C_{1-8}$alkyl group, especially a N-dimethylaminoethyl or N-diethylaminoethyl group or a $C_{1-6}$alkyloxy$C_{1-6}$alkyl group, especially a methyloxyethyl group. Especially preferred esterified carboxyl groups include —$CO2CH_3$, —$CO_2CH_2CH_3$, —$CO_2CH_2CH_2CH_3$ and —$CO_2CH(CH_3)_2$ groups.

In general in compounds of formulae (1) and (2) $R^1$ is preferably a hydrogen atom.

In general in compounds of formulae (1) and (2) $L^2$ is preferably $L^{2a}$ where $L^{2a}$ is an —O— atom or —$N(R^8)$— group in which $R^8$ is preferably a hydrogen atom or a methyl group. An especially useful —$N(R^8)$— group is —NH—.

In general in compounds of formulae (1) and (2) when n is zero or the integer 1 the group $R^2$ may especially be an optionally substituted heteroaliphatic, cycloaliphatic, heterocycloaliphatic, aromatic or heteroaromatic group as defined herein. Particularly useful groups of this type include optionally substituted $C_{2-6}$heteroalkyl, particularly $C_{1-3}$alkoxy$C_{1-3}$alkyl, especially methoxypropyl, optionally substituted $C_{3-7}$cycloalkyl, especially optionally substituted cyclopropyl, cyclobutyl cyclopropyl or cyclohexyl, optionally substituted $C_{5-7}$heterocycloaliphatic, especially optionally substituted pyrrolidinyl, morpholinyl, thiomorpholinyl, or thiazolidinyl, especially optionally substituted phenyl and optionally substituted $C_{5-7}$heteroaromatic, especially optionally substituted pyridyl groups. Optional substituents on these groups include in particular $R^{13}$ atoms or groups where the group is an aromatic or heteroaromatic group and -$(L^6)_p(Alk^5)_qR^{12}$ groups as described earlier where the group is a nitrogen-containing heterocycloaliphatic group such as a pyrrolidinyl or thiazolidinyl, piperidinyl, homopiperidinyl, heptamethyleneiminyl, piperazinyl, homopiperazinyl, morpholinyl or thiomorpholinyl piperidinyl, homopiperidinyl, heptamethyleneiminyl, piperazinyl, morpholinyl or thiomorpholinyl group. Particularly useful -$(L^6)_p(Alk^5)_qR^{12}$ groups include those in which $L^6$ is a —CO— group. $Alk^5$ in these groups is preferably present (i.e. q is preferably an integer 1) and in particular is a —$CH_2$-chain. Compounds of this type in which $R^{12}$ is a hydrogen atom or an optionally substituted aromatic or heteroaromatic group, especially an optionally substituted phenyl, pyridyl or imidazolyl group are particularly preferred.

In one preferred class of compounds of formulae (1) and (2) $L^1$ is present as a —N($R^8$)— group. Particularly useful —N($R^8$)— groups include —NH— and —N($C_{1-6}$alkyl)—, especially —N(CH$_3$)—, —N(CH$_2$CH$_3$)— and —N(CH$_2$CH$_2$CH$_3$)— groups. In this class of compounds n is preferably the integer 1 and Alk$^1$ is preferably an optionally substituted straight or branched $C_{1-6}$alkylene chain. Particularly useful Alk$^1$ chains include —CH$_2$—, —CH$_2$CH$_2$—, —CH$_2$CH$_2$CH$_2$—, —CH(CH$_3$)CH$_2$— and —C(CH$_3$)$_2$CH$_2$—. $R^2$ in this class of compounds is preferably a hydrogen atom.

In another preferred class of compounds of formulae (1) and (2) $L^1$ is a covalent bond, n is the integer (1) and Alk$^1$ is an optionally substituted straight or branched $C_{1-6}$alkylene chain. Particularly useful Alk$^1$ chains include —CH$_2$—, —CH$_2$CH$_2$—, —CH$_2$CH$_2$CH$_2$—, —CH(CH$_3$)CH$_2$— and especially —C(CH$_3$)$_2$CH$_2$— chains. $R^2$ in this class of compounds is preferably a hydrogen atom. A most especially useful optionally substituted Alk$^1$R$^2$ group is —C(CH$_3$)$_3$.

In another preferred class of compounds of formulae (1) and (2), $L^1$ is a covalent bond, n is zero and $R^2$ is an optionally substituted $C_{5-7}$heterocycloaliphatic group most especially an optionally substituted $C_{5-7}$heterocycloalkyl group. Especially useful $C_{5-7}$heterocycloalkyl groups include optionally substituted piperidinyl, homopiperidinyl (azepanyl), heptamethyleneiminyl, pyrrolidinyl, piperazinyl, homopiperazinyl, morpholinyl and thiomorpholinyl groups. Most preferred $C_{5-7}$heterocycloaliphatic groups are those linked via a ring nitrogen atom to the remainder of the compound of formulae (1) or (2). Most especially useful $C_{5-7}$heterocycloaliphatic groups include optionally substituted pyrolidin-1-yl, piperidin-1-yl and homopiperidin-1-yl (azepan-1-yl) groups. Especially useful optional substituents on these $C_{5-7}$heterocycloaliphatic groups include optionally substituted $C_{1-6}$alkyl groups, especially methyl, ethyl or i-propyl groups. Most preferred optionally substituted $C_{5-7}$heterocycloaliphatic groups include 2-methylpyrrolidin-1-yl, cis and trans 2,5-dimethylpyrrolidin-1-yl, 2-methylpiperidin-1-yl and 2,6-dimethylpiperidin-1-yl, homopiperidin-1-yl (azepan-1-yl), 2-methylhomopiperidin-1-yl (2-methyazepan-1-yl) and cis and trans 2,7-dimethylhomopiperidin-1-yl groups.

Particularly useful compounds of the invention include:

(S)-3-[4-(2,7-Naphthyridin-1-ylamino)phenyl]-2-[2-N,N-diethylamino-3,4-dioxocyclobut-1-enylamino]propanoic acid;

(S)-3 [4-(2,7-Naphthyridin-1-ylamino)phenyl]-2-[2-N,N-di-n-propylamino-3,4-dioxocyclobut-1-enylamino] propanoic acid;

(S)-3-[4-(2,7-Naphthyridin-1-ylamino)phenyl]-2-[2-(cis-2,5-dimethylpyrrolidin-1-yl)-3,4-dioxocyclobut-1-enylamino]propanoic acid;

(S)-3-[4-(2,7-Naphthyridin-1-ylamino)phenyl]-2-[(trans-2,5-dimethylpyrrolidin-1-yl)-3,4-dioxocyclobut-1-enylamino]propanoic acid;

(S)-3-[4-(2,7-Naphthyridin-1-yloxy)phenyl]-2-[2-N,N-diethylamino-3,4-dioxocyclobut-1-enylamino]propanoic acid;

(S)-3-[4-(2,7-Naphthyridin-1-yloxy)phenyl]-2-[2-(N,N-di-n-propylamino)-3,4-dioxocyclobut-1-enylamino] propanoic acid;

(S)-3-[4-(2,7-Naphthyridin-1-yloxy)phenyl]-2-[2-(cis-2,5-dimethylpyrrolidin-1-yl)-3,4-dioxocyclobut-1-enylamino]propanoic acid;

(S)-3-[4-(2,7-Naphthyridin-1-ylamino)phenyl]-2-[(2-[(2S),(5S)-dimethylpyrrolidin-1-yl)-3,4-dioxocyclobut-1-enyl)amino]propanoic acid;

(S)-3-[4-(2,7-Naphthyridin-1-yloxy)phenyl]-2-[2-(azepan-1-yl)-3,4-dioxocyclobut-1-enylamino]propanoic acid;

(S)-3-[4-(3-Methyl-2,7-naphthyridin-1-ylamino)phenyl]-2-[2-N,N-diethylamino-3,4-dioxocyclobut-1-enylamino]-propanoic acid;

(S)-3-[4-(3-Methyl-2,7-naphthyridin-1-ylamino)phenyl]-2-[2-N,N-di-n-propylamino-3,4-dioxocyclobut-1-enylamino]-propanoic acid;

(S)-3-[4-(3-Methyl-2,7-naphthyridin-1-ylamino)phenyl]-2-[2-(cis-2,5-dimethylpyrrolidin-1-yl)-3,4-dioxocyclobut-1-enylamino]propanoic acid;

(S)-3-[4-(3-Methyl-2,7-naphthyridin-1-yloxy)phenyl]-2-[2-N,N-diethylamino-3,4-dioxocyclobut-1-enylamino] propanoic acid;

(S)-3-[4-(3-Methyl-2,7-naphthyridin-1-yloxy)phenyl]-2-[2-N,N-di-n-propylamino-3,4-dioxocyclobut-1-enylamino] propanoic acid;

(S)-3-[4-(3-Methyl-2,7-naphthyridin-1-yloxy)phenyl]-2-[2-(cis-2,5-dimethylpyrrolidin-1-yl)-3,4-dioxocyclobut-1-enylamino]propanoic acid;

(S)-3-[4-(3-Methyl-2,7-naphthyridin-1-yloxy)phenyl]-2-[2-(trans-dimethylpyrrolidin-1-yl)-3,4-dioxocyclobut-1-enylamino]propionic acid;

(S)-3-[4-(3-Methyl-2,7-naphthyridin-1-yloxy)phenyl]-2-[2-(azepan-1-yl)-3,4-dioxocyclobut-1-enylamino]propanoic acid;

(S)-3-[4-(3-Methyl-2,7-naphthyridin-1-ylamino)phenyl]-2-[2-(azepan-1-yl-3,4-dioxocyclobut-1-enylamino] propanoic acid;

(S)-3-[4-(3-Isobutyl-2,7-naphthyridin-1-yloxy)phenyl]-2-(2-azepan-1-yl-3,4-dioxocyclobut-1-enylamino) propanoic acid;

(S)-3-[4-(3-Isobutyl-2,7-naphthyridin-1-yloxy)phenyl]-2-(2-N,N-diethylamino-3,4-dioxocyclobut-1-enylamino) propanoic acid;

and the salts, solvates, hydrates, N-oxides and carboxylic acid ester, particularly methyl, ethyl, propyl and i-propyl esters thereof Most especially preferred compounds of the invention include:

(S)-3-[4-(2,7-Naphthyridin-1-yloxy)phenyl]-2-[2-N,N-diethylamino-3,4-dioxocyclobut-1-enylamino]-propanoic acid;

(S)-3-[4-(2,7-Naphthyridin-1-yloxy)phenyl]-2-[2-(N,N-di-n-propylamino)-3,4-dioxocyclobut-1-enylamino] propanoic acid;

(S)-3-[4-(2,7-Naphthyridin-1-yloxy)phenyl]-2-[2-(azepan-1-yl)-3,4-dioxocyclobut-1-enylamino]propanoic acid;

(S)-3-[4-(3-Methyl-2,7-naphthyridin-1-yloxy)phenyl]-2-[2-N,N-di-n-propylamino-3,4-dioxocyclobut-1-enylamino]-propanoic acid;

(S)-3-[4-(3-Methyl-2,7-naphthyridin-1-yloxy)phenyl]-2-[2-N,N-diethylamino-3,4-dioxocyclobut-1-enylamino] propanoic acid;

(S)-3-[4-(3-Methyl-2,7-naphthyridin-1-yloxy)phenyl]-2-[2-NN-di-n-propylamino-3,4-dioxocyclobut-1-enylamino] propanoic acid, dimethylpyrrolidin-1-yl)-3,4-dioxocyclobut-1-enylamino]propanoic acid (S)-3-[4-(3-Methyl-2,7-naphthyridin-1-yloxy)phenyl]-2-[2-(azepan-1-yl)-3,4-dioxocyclobut-1-enylamino]propanoic acid;

(S)-3-[4-(3-Isobutyl-2,7-naphthyridin-1-yloxy)phenyl]-2-(2-azepan-1-yl-3,4-dioxocyclobut-1-enylamino) propanoic acid;

(S)-3-[4-(3-Isobutyl-2,7-naphthyridin-1-yloxy)phenyl]-2-(2-N,N-diethylamino-3,4-dioxocyclobut-1-enylamino)propanoic acid;

and the salts, solvates, hydrates, N-oxides and carboxylic acid ester, particularly methyl, ethyl, propyl and i-propyl esters thereof.

Compounds according to the inventions are potent and selective inhibitors of α4 integrins and have advantageous clearance properties, especially those compounds where R is a carboxylic ester or amide. The ability of the compounds to act in this way may be simply determined by employing tests such as those described in the Examples hereinafter.

The compounds are of use in modulating cell adhesion and in particular are of use in the prophylaxis and treatment of diseases or disorders involving inflammation in which the extravasation of leukocytes plays a role and the invention extends to such a use and to the use of the compounds for the manufacture of a medicament for treating such diseases or disorders.

Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, coloring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use. For particle mediated administration the compounds of formula (1) may be coated on particles such as microscopic gold particles.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 10 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $Ar^1$, $Ar^2$, Alk, $R^1$, $R^2$, $L^1$, $L^2$, $Alk^1$ and n when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1999]. In some instances, deprotection may be the final step in the synthesis of a compound of formula (1) and the processes according to the invention described hereinafter are to be understood to extend to such removal of protecting groups. For convenience the processes described below all refer to a preparation of a compound of formula (1) but clearly the description applies equally to the preparation of compounds of formula (2).

Thus according to a further aspect of the invention, a compound of formula (1) in which R is a —$CO_2H$ group may be obtained by hydrolysis of an ester of formula (3):

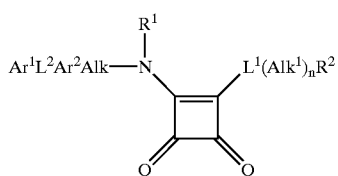

(3)

where Alk represents a group

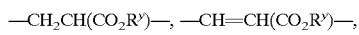

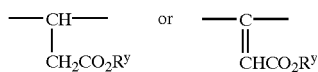

[where $R^y$ is an alkyl group for example a $C_{1-6}$alkyl group]

The hydrolysis may be performed using either an acid or a base depending on the nature of $R^y$, for example an organic acid such as trifluoroacetic acid or an inorganic base such as lithium, sodium or potassium hydroxide optionally in an aqueous organic solvent such as an amide e.g. a substituted amide such as dimethylformamide, an ether e.g. a cyclic ether such as tetrahydrofuran or dioxane or an alcohol e.g. methanol at a temperature from ambient to the reflux temperature. Where desired, mixtures of such solvents may be used.

According to a further aspect of the invention a compound of formula (1) may be prepared by displacement of a leaving group from a compound of formula (4):

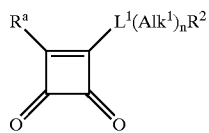

(4)

where $R^a$ is a leaving group, with an amine $Ar^1L^2Ar^2AlkN(R^1)H$ or a salt thereof. Suitable leaving groups represented by $R^a$ include halogen atoms, especially chlorine and bromine atoms, or alkoxy, e.g. methoxy, ethoxy or isopropoxy, aryloxy, e.g. dinitrophenyloxy, or aralkoxy, e.g. benzyloxy, groups.

The reaction may be performed in an inert solvent or mixture of solvents, for example a substituted amide such as dimethylformamide, an alcohol such as ethanol and/or a halogenated hydrocarbon such as dichloromethane, at a temperature from 0° C. to the reflux temperature. Where necessary, for example when a salt of an amine $Ar^1L^2Ar^2AlkN(R^1)H$ is used, an organic base such as diisopropylethylamine can be added.

Any carboxylic acid group present in the intermediate of formula (4) or the amine $Ar^1L^2Ar^2AlkN(R^1)H$ may need to be protected during the displacement reaction, for example as an ethyl ester. The desired acid may then be obtained through subsequent hydrolysis, for example as particularly described above and generally described below.

It will be appreciated that the displacement reaction may also be performed on a compound of formula (5):

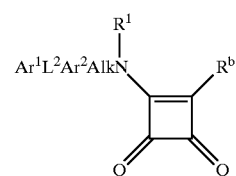

(5)

where $R^b$ is a leaving group as defined for $R^a$ using an intermediate $R^2(Alk^1)_nL^1H$ where $-L^1H$ is a functional group such as an amine ($-NH_2$) using the reaction conditions just described.

Where desired the displacement reaction may also be performed on an intermediate of formulae (4) or (5), $Ar^1L^2Ar^2AlkN(R^1)H$ or $R^2(Alk^1)_nL^1H$ which is linked, for example via its $Ar^1$ or $R^2$ group, to a solid support, such as a polystyrene resin. After the reaction the desired compound of formula (1) may be displaced from the support by any convenient method, depending on the original linkage chosen.

Intermediates of formulae (4) and (5) are either readily available or may be prepared from an intermediate of formula (6):

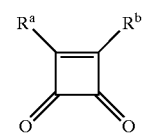

(6)

where $R^a$ and $R^b$ are as previously defined and an amine $Ar^1L^2Ar^2AlkN(R^1)H$ or $R^2(Alk^1)_nN(R^8)H$ by displacement as just described for the preparation of compounds of formula (1).

Intermediates of formulae $Ar^1L^2Ar^2AlkN(R^1)H$ and $R^2(Alk^1)_nN(R^8)H$ may be obtained from simpler, known compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other compounds of formulae (1) and (2) where appropriate functional groups exist in these compounds.

Thus compounds of the invention and intermediates thereto may be prepared by alkylation, arylation or heteroarylation. For example, compounds containing a $-L^1H$ or $-L^2H$ group (where $L^1$ and $L^2$ is each a linker atom or group) may be treated with a coupling agent $R^2(Alk^1)_nX^1$ or $Ar^1X^1$ respectively in which $X^1$ is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. p-toluenesulphonyloxy group.

The reaction may be carried out in the presence of a base such as a carbonate, e.g. caesium or potassium carbonate, an alkoxide, e.g. potassium t-butoxide, or a hydride, e.g. sodium hydride, or an organic amine e.g. triethylamine or N,N-diisopropylethylamine or a cyclic amine, such as N-methylmorpholine or pyridine, in a dipolar aprotic solvent such as an amide, e.g. a substituted amide such as dimethylformamide or an ether, e.g. a cyclic ether such as tetrahydrofuran.

Intermediates of formulae $Ar^1X^1$ and $R^2(Alk^1)_nX^1$ are generally known readily available compounds or may be prepared from known compounds by standard substitution and other synthetic procedures, for example as described herein. Thus for example compounds of formula $Ar^1X^1$ in which $Ar^1$ represents an optionally substituted 2,7-naphthyridin-1-yl group may be prepared from alcohols of formula $Ar^1OH$ by reaction with a halogenating agent, for example a phosphorous oxyhalide such as phosphorous oxychloride at an elevated temperature e.g. 110° C.

Intermediate alcohols of formula $Ar^1OH$ in which $Ar^1$ represents an optionally substituted 2,7-naphthyridin-1-yl group may be prepared by methods well known to a person skilled in the art, e.g. by the method of Sakamoto, T. et al [Chem. Pharm. Bull. 33, 626–633, (1985)] or Baldwin, J, J. et al [J. Org. Chem, 43, 4878–4880, (1978)]. Thus for example the method of Baldwin may be modified to allow the synthesis of intermediate 3-substituted 2,7-naphthyridin-1-yl groups of formula $Ar^1OH$ as depicted in Scheme 1:

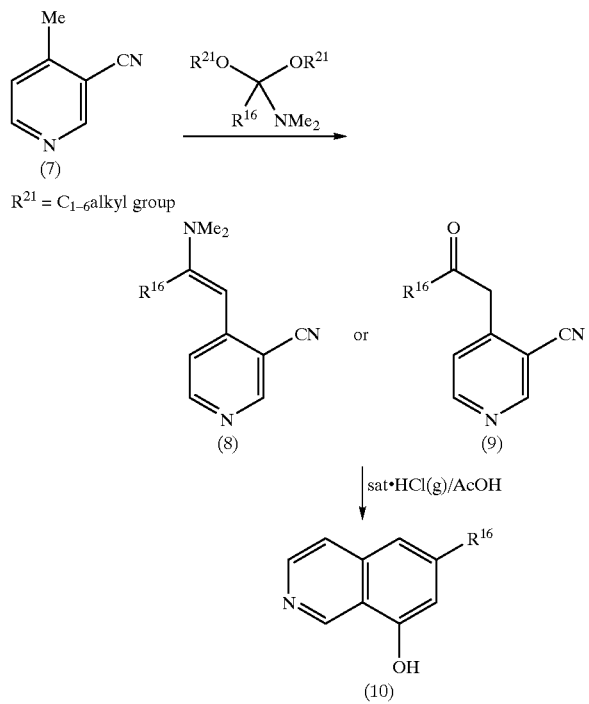

$R^{21}$ = $C_{1-6}$alkyl group

Reaction of an optionally substituted 4-methyl-3-cyano pyridine of formula (7) with a N,N-dimethylformamide di-$C_{1-6}$alkyl acetal, e.g. N,N-dimethylformamide diethyl acetal, in a dipolar solvent such as an amide e.g. a substituted amide such as dimethylformamide at an elevated temperature e.g. 140–150° gives a compound of formula (8) or (9) or a mixture thereof depending on the nature of the group $R^{16}$.

Compounds of formula (8) or (9) may be cyclised to 3-substituted 2,7-naphthyridin-1-yl alcohol of formula (10) by treatment with an acid e.g. an inorganic acid such as hydrochloric acid or hydrobromic acid or an acidic gas such as hydrogen chloride gas in an organic solvent e.g. an organic acid such as acetic acid optionally in the presence of water at a temperature from about ambient to 50° C.

Alternatively alkylating agents of formula $Ar^1X^1$ in which $Ar^1$ represents an optionally substituted 2,7-naphthyridin-yl group may be prepared by reaction of a 2,7-naphthyridine N-oxide or N, N'-dioxide with a halogenating agent, e.g. a phosphorous oxyhalide such as phosphorous oxychloride to give a 1-halo or 1,6-dihalo- and/or-1,8-dihalo-2,7-napthyridine respectively. In the case of 1,6-dihalo- and/or 1,8-dialo-2,6-napthyridines each halogen atom may be substituted separately by a reagent such as $HL^2Ar^2AlkN(R^1)H$ or $HL^3(Alk^2)_tL^4(R^4)_u$ by the particular methods just described above.

2,7-Napthyridine N-oxides and N,N'-dioxides may be generated from the corresponding 2,7-napthyridines by the general methods of synthesis of N-oxides described below or they may be synthesised by the methods of Numata, A. et al (Synthesis, 1999, 306–311).

Further alkylating agents of formula $Ar^1X^1$ in which, for example, $Ar^1$ represents a 2,7-naphthyridin-1-yl, may be prepared by the methods of Wenkert E. et al J. Am. Chem. Soc. 89, 6741–5 (1967), and Aust. J. Chem. 433 (1972), and Sheffield D. J. J. Chem. Soc. Perkin. Trans I, 2506 (1972).

In a further example intermediates of formula $Ar^1L^2Ar^2AlkN(R^1)H$ may be obtained by reaction of a compound of formula $Ar^1L^2H$ with a compound of formula $X^1Ar^2AlkN(R^1)H$ under the reaction conditions just described Compounds of formula $Ar^1L^2H$ in which, for example $Ar^1$ represents a 2,7-naphthyridin-1-yl group and $L^2$ is a —$N(R^8)$— group, may be prepared from substituted 4-formylpyridines by the methods of Molina, P. et al Tetrahedron, 48, 4601–4616, (1992), or by the methods described in U.S. Pat. No. 3,938,367.

In another example, compounds containing a -$L^1$H or -$L^2$H or group as defined above may be functionalised by acylation or thioacylation, for example by reaction with one of the alkylating agents just described but in which $X^1$ is replaced by a —$C(O)X^2$, $C(S)X^2$, —$N(R^8)COX^2$ or —$N(R^8)C(S)X^2$ group in which $X^2$ is a leaving atom or group as described for $X^1$. The reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature. Alternatively, the acylation may be carried out under the same conditions with an acid (for example one of the alkylating agents described above in which $X^1$ is replaced by a —$CO_2H$ group) in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction In a further example compounds may be obtained by sulphonylation of a compound containing an —OH group by reaction with one of the above alkylating agents but in which $X^1$ is replaced by a —S(O)Hal or —$SO_2$Hal group in which Hal is a halogen atom such as chlorine atom] in the presence of a base, for example an inorganic base such as sodium hydride in a solvent such as an amide, e.g. a substituted amide such as dimethylformamide at for example ambient temperature.

In another example, compounds containing a -$L^1$H or -$L^2$H group as defined above may be coupled with one of the alkylation agents just described but in which $X^1$ is replaced by an —OH group in a solvent such as tetrahydrofuran in the presence of a phosphine, e.g. triphenylphosphine and an activator such as diethyl, diisopropyl- or dimethylazodicarboxylate.

In a further example, ester groups —$CO_2R^5$, —$CO_2R^{11}$ or —$CO_2Alk^7$ in the compounds may be converted to the corresponding acid [—$CO_2H$] by acid- or base-catalysed hydrolysis depending on the nature of the groups $R^5$, $R^{11}$ or $Alk^7$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a further example, —$OR^5$ or —$OR^{14}$ groups [where $R^5$ or $R^{14}$ each represents an alkyl group such as methyl group] in compounds of formula (1) may be cleaved to the corresponding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding —$OCH_2R^{14}$ group (where $R^{14}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [$CO_2R^{11}$ or $CO_2R^5$] or aldehyde [—CHO] by reduction, using for example a complex metal hydride such as lithium aluminium hydride or sodium borohydride in a solvent such as methanol.

In another example, alcohol —OH groups in the compounds may be converted to a corresponding —$OR^5$ or —$OR^{14}$ group by coupling with a reagent $R^5OH$ or $R^{14}OH$ in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NHR^2$ or —$NHSO_2NHAr^1$] groups in the compounds may be obtained, in another example, by reaction of a corresponding amine [—$NH_2$] with a sulphamide $R^2NHSO_2NH_2$ or $Ar^1NHSO_2NH_2$ in the presence of an organic base such as pyridine at an elevated temperature, e.g. the reflux temperature.

In another example compounds containing a —$NHCSAr^1$, —$CSNHAr^1$, —$NHCSR^2$ or —$CSNHR^2$ may be prepared by treating a corrsponding compound containing a —$NHCOAr^1$, —$CONHAr^1$, —$NHCOR^2$ or —$CONHR^2$ group with a thiation reagent, such as Lawesson's Reagent, in an anhydrous solvent, for example a cyclic ether such as tetrahydrofuran, at an elevated temperature such as the reflux temperature.

In a further example amine (—$NH_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—$NH_2$] groups in compounds of formula (1) may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

Aromatic halogen substituents in the compounds may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyldisulphide as the electrophile.

In another example, sulphur atoms in the compounds, for example when present in a linker group $L^1$ or $L^2$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

In another example compounds of formula $Ar^1X^1$ (where $X^1$ is a halogen atom such as a chlorine, bromine or iodine atom) may be converted to such compounds as $Ar^1CO_2R^{20}$ (in which $R^{20}$ is an optionally substituted alkyl, aryl or heteroaryl group), $Ar^1CHO$, $Ar^1CHCHR^{20}$, $Ar^1CCR^{20}$, $Ar^1N(R^{20})H$, $Ar^1N(R^{20})_2$, for uses in the synthesis of for example compounds of formula $Ar^1L^2Ar^2AlkN(R^1)H$, using such well know and commonly used palladium mediated reaction conditions as are to be found in the general reference texts *Rodd's Chemistry of Carbon Compounds,* Volumes 1–15 and Supplementals (Elsevier Science Publishers, 1989), *Fieser and Fieser's Reagents for Organic Synthesis,* Volumes 1–19 (John Wiley and Sons, 1999), *Comprehensive Heterocyclic Chemistry,* Ed. Katritzky et al, Volumes 1–8, 1984 and Volumes 1–11, 1994 (Pergamon), *Comprehensive Organic Functional Group Transformations,* Ed. Katritzky et al, Volumes 1–7, 1995 (Pergamon), *Comprehensive Organic Synethesis,* Ed. Trost and Flemming, Volumes 1–9, (Pergamon, 1991), *Encyclopedia of Reagents for Organic Synthesis,* Ed. Paquette, Volumes 1–8 (John Wiley and Sons, 1995), *Larock's Comprehensive Organic Transformations* (VCH Publishers Inc., 1989) and *March's Advanced Organic Chemistry* (John Wiley and Sons, 1992).

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

Chromatography, recrystallisation and other conventional separation procedures may also be used with intermediates or final products where it is desired to obtain a particular geometric isomer of the invention.

The following Examples illustrate the invention. All temperatures are in 0° C. The following abbreviations are used:

| | |
|---|---|
| NMM-N-methylmorpholine; | EtOAc-ethyl acetate; |
| MeOH-methanol; | BOC-butoxycarbonyl; |
| DCM-dichloromethane; | AcOH-acetic acid; |
| DIPEA-diisopropylethylamine; | EtOH-ethanol; |
| Pyr-pyridine; | Ar-aryl; |
| DMSO-dimethylsulphoxide; | iPr-isopropyl; |
| Et$_2$O-diethylether; | Me-methyl; |
| THF-tetrahydrofuran, | DMF-N,N-dimethylformamide; |
| FMOC-9-fluorenylmethoxycarbonyl; | TFA-trifluoroactic acid; |

All NMR's were obtained at 300 MHz unless otherwise indicated.

Intermediate 1

4-(2-(N,N-Dimethylamino)ethylen-1-yl)-3-cyanopyridine

A solution of 4-methyl-3-cyanopyridine (prepared according to Ref: J. Prakt. Chem. 338, 663 (1996), 8.0 g, 67.8 mmol) and N,N-dimethylformamide diethyl acetal (11.0 g, 74.8 mmol) in dry DMF (50 ml) was stirred at 140° under $N_2$ for 2 days. An additional portion of N,N,-dimethylformamide diethyl acetal (5 g) was added and stirred at 140° for 4 h. The volatiles were removed in vacuo and the obtained dark oil partitioned between EtOAc (300 ml) and water (50 ml). The phases were separated and the aqueous layer re-extracted with EtOAc (3×100 ml). The combined organic extracts were washed with brine (30 ml), dried ($Na_2SO_4$), treated with activated charcoal, filtered and evaporated in vacuo to afford essentially pure title compound as a dull orange solid (10.1 g, 85%). δH (CDCl$_3$) 8.49 (1H, s), 8.25 (1h, d, J 5.9 hz), 7.29 (1H, d, J 13.2 Hz), 7.09 (1H, d, J 5.9 Hz), 5.25 (1H, d, J 13.2 Hz) and 2.99 (6H, s); m/z (ES$^+$, 70V) 174 (MH$^+$).

Intermediate 2

1-Hydroxy-2,7-naphthyridine Hydrochloride Salt

HCl gas was bubbled through a stirred solution of Intermediate 1 (6.2 g, 3.58 mmol) in glacial acetic acid (50 ml) and water (0.64 ml, 3.55 mmol) for 1–2 min. The reaction mixture was stirred in a stoppered flask at 40° for 18 h. The volatiles were removed in vacuo affording a dark residue, which was treated with water (3×20 ml) and re-evaporated in vacuo. The obtained dark semi-solid was treated with 40 ml warm ethanol, ice-cooled, and the undissolved solid collected by filtration affording the title compound as a green colored solid (5.2 g, 80%) δH (DMSO-D$^6$) 12.5 (1H, br s), 9.38 (1H, s), 8.84 (1H, d, J 7.0 Hz), 8.15 (1H, d, J 7.0 Hz), 7.89 (1H, br dd, J 7.0, 5.0 Hz) and 6.85 (1H, d, J 7.0 Hz); m/z (ES$^+$, 70V), 147 (MH$^+$).

Intermediate 3

1-Chloro-2,7-naphthyridine

Intermediate 2 (5.2 g, 28.5 mmol) was stirred with phosphorous oxychloride (75 ml) at 110° for 24 h. The volatiles were removed in vacuo affording a dark oil which was poured into an ica-bath cooled mixture of saturated aqueous NaHCO$_3$ (100 ml containing 20 g solid NaHCO$_3$) and EtOAc (100 ml). After thorough mixing the phases were separated and the aqueous layer re-extracted with EtOAc (2×75 ml). The combined organic extracts were washed with brine (15 ml), dried (Na$_2$SO$_4$) and evaporated in vacuo to afford the title compound as a yellow solid (4.0 g, 85%) δH (CDCl$_3$) 9.45 (1H, s), 8.81 (1H, d, J 5.7 HZ), 8.47 (1H, d, J 5.7 Hz), 7.66 (1H, d, J 5.7 Hz) and 7.60 (1H, d,J 5.7 HZ); m/z (ES$^+$, 70V) 165 and 167 (MH$^+$).

Intermediate 4

Ethyl (S)-3-[4-(2,7-naphthyridin-1-ylamino)phenyl]-2-aminopropanoate

A solution of ethyl-(S)-3-[4-aminophenyl]-2-[t-butoxycarbonylamino] propanoate (638 mg, 2.07 mmol) and Intermediate 3 (310 mg, 1.88 mmol) in ethoxyethanol (2 ml) was stirred at 120° for 15 min and at 100° for 1 h under nitrogen. The volatiles were removed in vacuo and the dark residue partitioned between EtOAc (70 ml) and saturated aqueous NaHCO$_3$ (10 ml). The phases were separated and the aqueous layer re-extracted with EtOAc (2×30 ml). The combined organic extracts were washed with brine (10 ml), dried (Na$_2$SO$_4$) and evaporated in vacuo to afford a dark foam. Chromatography (SiO$_2$; 5 to 10% MeOH/DCM) afforded a mixture of ethyl-(S)-3-[4-(2,7-naphthyridin-1-ylamino)phenyl]-2-[(t-butoxycarbonyl) amino]propanoate and some of the title compound (730 mg). This mixture was treated with a solution of trifluoroacetic acid (5 ml) and DCM (5 ml) at room temperature for 1 h. The volatiles were removed in vacuo and the residue partitioned between EtOAc (75 ml) and saturated aqueous NaHCO$_3$ (20 ml). The phases were separated and the aqueous layer re-extracted with EtOAc (3×30 ml). The combined organic extracts were washed with brine (10 ml), dried (Na$_2$SO$_4$) and evaporated in vacuo to afford an orange solid. Chromatography (silica; 10% MeOH/DCM) afforded the title compound as a straw-colored solid (420 mg, 60% over two steps). δH (CDCl$_3$) 10.70 (1H, s), 10.31 (1H, s), 9.44 (1H, d, J 5.6 Hz), 8.94 (1H, d, J 5.6 Hz), 8.55 (1H, d, J 7.3 Hz), 8.54 (2H, d, J 8.5 Hz), 8.46 (1H, d, J 5.6 Hz), 7.94 (2H, d, J 8.5 Hz), 4.84 (2H, q, J 7.1 Hz), 4.35 (1H, t, J 6.6 Hz), 4.10 (2H, br s), 3.64 (1H, dd, J 13.5, 6.4 Hz), 3.56 (1H, dd, J 13.5, 7.0 Hz) and 1.95 (3H, t, J 7.1 Hz); m/z (ES$^+$, 70V) 337 (MH$^+$).

Intermediate 5

Methyl-(S)-3-{(4-(3-methoxycarbonyl)-2,7-naphthyridin-1-ylamino) phenyl}-2-[(t-butoxycarbonyl)amino]propanoate To triphosgene (187 mg, 0.63 mmol) in DCM (3.5 ml) was added a solution of methyl-(S)-3-[4-aminophenyl]-2-[t-butoxycarbonylamino]propanate (500 mg, 1.70 mmol) and iPr$_2$EtN (242 mg, 1.87 mmol) in DCM (6 ml) over 1 h. After a further 15 min the reaction was diluted with DCM (50 ml), washed (2×25 ml, 0.5M HCl and 2×25 ml saturated NaCl), dried (MgSO$_4$) and the solvent removed in vacuo to yield the crude intermediate isocyanate as a viscous pale brown oil. To the crude isocyanate (194 mg, 0.61 mol) in toluene (18 ml) was added methyl β-(4-pyridyl)-α-(triphenyl-phosphorilidenamino)acrylate (241 mg, 0.55 mmol) prepared in accordance with the method described in Tetrahedron (1992), 48, 4601. The reaction was stirred at ambient temperature overnight followed by heating at 160° in a sealed tube for 3 days. The solvent was removed and the soluble residues purified by chromatography (SiO$_2$; 50–100% EtOAc: hexane) to yield the title compound (157 mg, 59%) as a bright yellow solid. δH (CD$_3$OD) 9.76 (1H, s), 8.68 (1H, d, J 5.7 Hz), 7.97 (2H, d, J 8.6 Hz), 7.89 (1H, s), 7.82 (1H, d, J 5.7 Hz), 7.21 (2H, d, J 8.6 Hz), 4.39 (1H, m), 3.97 (3H, s), 3.71 (3H, s), 3.10 (1H, m), 2.94 (1H, m), 1.40 (9H, s); m/z (ES$^+$, 70V) 480 (MH$^+$).

Intermediate 6

Methyl (S)-3-[4-(2,7-naphthyridin-1-yloxy)phenyl]-2-aminopropanoate

A mixture of N-(BOC)-(S)-tyrosine methyl ester (1.71 g, 5.80 (mmol) potassium carbonate (0.80 g, 5.80 mmol) and Intermediate 3 (1.0 g, 6.08 mmol) in dry DMF (10 ml) was stirred at room temperature for 18 h, and at 40° for 18 h. The DMF was removed in vacuo and the residue partitioned between EtOAc (80 ml) and 10% aqueous Na$_2$CO$_3$ (20 ml). The phases were separated and the aqueous layer re-extracted with EtOAc (2×20 ml). The combined organic extracts were washed with brine (10 ml), dried (Na$_2$SO$_4$) and evaporated in vacuo to afford a new colorless oil. Chromatography (silica; 2.5% MeOH/DCM) afforded reasonably pure N-t-butoxycarbonyl protected title compound (1.75 g, 71%). This material was dissolved in EtOAc (40 ml) and HCl gas was bubbled through the stirred solution for 1 min. then the mixture was stirred for an additional 0.5 h. The volatiles were removed in vacuo affording a yellow solid which was partitioned between EtOAc (80 ml) and saturated aqueous NaHCO$_3$ (20 ml). The phases were separated and the aqueous layer re-extracted with EtOAc (2×20ml). The combined organic extracts were washed with brine (10 ml), dried (Na$_2$SO$_4$) and evaporated in vacuo. The obtained oil was chromatographed (silica; 5% MeOH/DCM) to afford the title compound as a near colorless oil (0.83 g, 62%) δH (CDCl$_3$) 9.77 (1H. s), 8.75 (1H, d, J 5.8 Hz), 8.10 (1H, d, J 5.8 Hz), 7.58 (1H, d, J 5.8 Hz), 7.29 (2H, d, J 8.4 Hz), 7.25 (1H, d, J 5.9 Hz), 7.21 (2H, d, J 8.4 Hz), 3.80–3.70 (1H, obscured m), 3.72 (3H, s), 3.15 (1H, dd, J 13.6, 5.1 Hz), 2.88 (1H, dd, J 13.6, 8.0 Hz) and 0.78 (2H, br s); m/z (ES$^+$, 70V) 324 (MH$^+$).

Intermediate 7

4-Acetonyl-3-cyanopyridine

A solution of 4-methyl-3-cyanopyridine (4 g, 33.9 mmol) and N,N-dimethylacetamide dimethylacetyl (5.4 g, 40.6 mmol) in dry DMF (20 ml) was stirred at 130° for 7 h. The volatiles were removed in vacuo to afford a dark oil which solidified on standing. This material was chromatographed (silica; 50% EtOAc/Hexane-100% EtOAc) affording the title compound as an off-yellow solid (3.73 g, 69%). δH (CDCl$_3$) 8.87 (1H, s), 8.74 (1H, d, J 5.2 Hz), 7.28 (1H, d, J 5,2 Hz), 4.00 (2H, s) and 2.36 (3H, s); m/z (ES$^+$, 70V) 161 (MH$^+$).

Intermediate 8

1-Hydroxy-3-methyl-2,7-naphthyridine Hydrochloride

HCl gas was bubbled through a stirred solution of Intermediate 7 (3.73 g, 23.3 mmol) in glacial acetic acid (40 ml) for several minutes. The flask was stoppered and reaction stirred for 18 h at ambient temperature. The volatiles were removed in vacuo affording a straw-colored solid. This was twice treated with water (30 ml portions) and re-evaporated in vacuo to dryness, affording the title compound (contaminated with 25% unidentified by-product) as a dark straw colored solid (4.1 g). δH (DMSO-d$^6$) 12.46 (1H, br s), 9.32 (1H, s), 8.71 (1H, d, J 6.5 Hz), 7.98 (1H, d, J 6.5 Hz), 6.67 (1H, s) and 2.38 (3H, s); m/Z (ES$^+$, 70V) 161 (MH$^+$). Used without further purification.

Intermediate 9

1-Chloro-3-methyl-2,7-naphthyridine

Intermediate 8 (4.1 g) was treated with phosphorus oxychloride (50 ml) at 130° for 3 h, affording a dark solution. The volatiles were removed in vacuo and the obtained dark oil extracted with Et$_2$O (100 ml). Saturated aqueous NaHCO$_3$ (ice cold; containing 10 g additional solid NaHCO$_3$) was poured (with CARE!) onto the crude product with swirling and ice-bath cooling. After thorough shaking, addition Et$_2$O (80 ml) was added, the mixture re-shaken, and the phases separated. The aqueous layer was re-extracted with Et$_2$O (2×80 ml) and the combined ethereal extracts washed with brine (20 ml), dried (Na2SO$_4$) and evaporated in vacuo to afford an orange solid (3.6 g). Chromatography (silica; 70% EtOAc/Hexane-100% EtOAc) afforded a more-polar by-product (3-methyl-1H-pyrano[3,4 -C]pyridin-1-one, (0.7 g) and the title compound as a white solid (2.82 g, 79% from intermediate 7) δH (CDCl$_3$) 9.66 (1H, s), 8.73 (1H, d, J 5.8 hz), 7.56 (1H, d, J 5.8 Hz), 7.40 (1H, s) and 2,69 (3H, s); m/z (ES$^+$, 70V) 179 and 181 (MH$^+$).

Intermediate 10

Ethyl (S)-3-[4-(3-methyl-2,7-naphthyridin-1-ylamino)phenyl]-2-[-N-(tertbutyloxycarbonyl) amino]propanoate Hydrochloride Acetylchloride (55 mg, 50 ml, 0.70 mmol) was added to absolute ethanol (25 ml) and stirred for one minute. Intermediate 9 (2.50 g, 14.0 mmol) and ethyl-(S)-3-[4-aminophenyl]-2-{tert-butyloxycarbonyl]propanoate (4.31 g, 14.0 mmol) were added and the reaction mixture stirred at 60° for 2.75 h. The volatiles were removed in vacuo to afford a yellow-orange solid. This was treated with EtOAc (~25 ml), warmed, re-cooled and the precipitate collected by filtration, with Et$_2$O washing, affording the title compound as yellow solid (4.96 g, 73%). δH (CDCl$_3$) 10.44 (1 h, br s), 10.33 (1H, br s), 8.60 (1H, d, J 6.5 Hz), 8.00 (1H, d, J 6.5 Hz), 7.85 (2H, d, J 8.5 Hz), 7.28 (1H, d, J 8.0 Hz), 7.23 (2H, d, J 8.5 Hz), 7.16 (1H, s), 4.19–4.01 (1H, m), 4.08 (2H, q, J 7.0 Hz), 2.97 (1H, dd, J 13.8, 5.4 Hz), 2.86 (1H, dd, J 13.8, 10.0 Hz), 2.50 (3H, s), 1.34 (9H, s) and 1.15 (3H, t, J 7.0 Hz); m/z (ES$^+$, 70V)451 (MH$^+$).

Intermediate 11

Ethyl-(S)-3-[4-3-methyl-2,7-naphthyridin-1-ylamino)phenyl]-2-aminopropanoate

HCl gas was bubbled through a stirred solution of Intermediate 10 (4.95 g, 10.2 mmol) for 1–2min. After 30 min stirring at ambient temperature the volatiles were removed in vacuo affording a yellow powder. This was treatd with saturated aqueous NaHCO$_3$ (30 ml) then extracted with EtOAc (100 ml, and 3×50 ml). The combined organic extracts were washed with brine (10 ml), dried (Na$_2$SO$_4$) and evaporated in vacuo affording the title compound as a yellow solid (3.56, 100%). δH (CDCl$_3$) 9.25 (1H, s), 8.50 (1H, d, J 5.6 Hz), 7.66 (2H, d, J 8.4 Hz), 7.35 (1H, d, J 5.6 Hz), 7.34 (1H, masked s), 7.14 (2H, d, J 8.4 Hz), 6.81 (1H, s), 4.12 (2H, q, J 7.2 Hz), 3.65 91H, dd, J 7.8, 5.2 Hz), 3.02 (1H, dd, J 13.7, 5.2 Hz), 2.80 (1H, dd, J 13.7, 7.8 Hz), 2.48 (3H, s), 1.56 (2H, br s) and 1.21 (3H, t, J 7.2 Hz); m/z (ES$^+$, 70V) 351 (MH$^+$).

Intermediate 12

Methyl (S)-3-[4-(3-methyl-2,7-naphthyridin-1-yloxy)phenyl]-2-(N-t-butyloxycarbonylamino) propanoate A mixture of N-t-butyloxycarbonyl-(S)-tyrosine methyl ester (2.55 g, 8.64 mmol) caesium carbonate (2.81 g, 8.62 mmol) and Intermediate 9 (140 g, 7.84 mmol) in dry DMF (30 ml) was stirred at room temperature for 2 days. The volatiles were removed in vacuo and the residue partitioned between EtOAc (100 ml) and 10% aqueous NH$_4$Cl solution. The aqueous layer was re-extracted with EtOAc (50 ml). The combined organic extracts were washed with brine (15 ml), dried (Na$_2$SO$_4$) and evaporated in vacuo to afford an oil (4.1 g). Chromatography (silica; 50%–70% EtOAc/Hexane) afforded the title compound as a white foam (3.1 g, 90%). δH (DMSO-d$^6$) 9.59 (1H, s), 8.72 (1H, d, J 5.7 Hz), 7.75 (1H, d, J 5.7 Hz), 7.37 (1H, br s), 7.36 (1H, d, J 5.7 Hz), 7.23 (2H, d, J 8.5 Hz), 4.23 (1H, m), 3.64 (3H, s), 3.05 (1H, dd, J 13.8, 5.1 Hz), 2.92 (1H, dd, J 13.8,10.1 Hz), 2.37 (3H, s) and 1.36 (9H, s); m/z (ES$^+$, 70V) 438 (MH$^+$).

Intermediate 13

Methyl (S)-3-[4-(3-methyl-2,7-naphthyridin-1-yl oxy)phenyl]-2-aminopropanoate Dihydrochloride HCl gas was bubbled through a stirred solution of intermediate 12 (3.1 g, 7.09 mmol) in EtOAc (60 ml) for approximately one minute. The reaction mixture was stirred at ambient temperature for 0.5 h then the volatiles were removed in vacuo to afford the title compound as a white powder (3.0 g, 100%) which was used immediately without further purification. δH (DMSO-d$^6$) 9.93 (1H, s), 8.86 (1H, d, J 6.5 Hz), 8.34 (1H, d, J 6.5 Hz), 7.68 (1H, s), 7.39 (2H, d, J 8.6 Hz), 7.34 (2H, d, J 8.6 Hz), 4.28 (1H, m), 3.68 (3H, s), 3.32 (1H, dd, J 14.0, 5.6 Hz), 3.17 (1H, dd, J 14.0, 7.9 Hz) and 2.49 (3H, s); m/z (ES$^+$, 70V) 338 (MH$^+$).

Intermediate 14

Ethyl (S)-3-[4-(3-methyl-2,7-naphthyridin-1-yloxy) phenyl]-2-(N-t-butyloxycarbonylamino)-propanoate A mixture of N-t-butyloxycarbonyl-(S)-tyrosine ethyl ester (14.5 g, 46.9 mmol), caesium carbonate (14.05 g, 43.1 mmol) and Intermediate 9 (7.0 g, 39.2 mmol) in dry DMF (60 ml) was stirred at room temperature for 48 h. The reaction was diluted with Et$_2$O (150 ml) and filtered off. The filtrate was evaporated under high vacuum and the residue was chromatographed (SiO$_2$; 40%–60% EtOAc/Hexane) which afforded the title compound as a viscous, straw-colored oil (16.2 g, 77%) δH (CDCl$_3$) 9.56 (1H, s), 8.58 (1H, d, J 5.8 Hz), 7.39 (1H, d, J 5.8 Hz), 7.15–7.10 (4H, m), 7.00 (1H, s), 4.99–4.91 (1H,m), 4.54–4.46 (1H, m), 4.09 (2H, q, J 7.1 Hz), 3.10–2.99 (2H,m), 2.36 (3H, s), 1.34 (9H, s) and 1.15 (3H, t, J 7.1 Hz); m/z (ES$^+$, 70V) 452 (MH$^+$).

Intermediate 15

Ethyl (S)-3-[4-(3-methyl-2,7-naphthyridin-1-yloxy) phenyl-]2-aminopropanoate

HCl gas was bubbled through a stirred solution of Intermediate 14 (16 g) in EtOAc (300 ml) until a persistent fine white precipitate formed (~2minutes). After stirring for 0.5 h the volatiles were removed in vacuo. The obtained solid was partitioned between EtOAc (250 ml) and saturated aqueous NaHCO$_3$ (80 ml plus 5 g solid NaHCO$_3$). The phases were separated and the aqueous layer re-extracted with EtOAc (5×50 ml). The combined organic extracts were washed with brine (10 ml), dried (Na$_2$SO$_4$) and evaporated in vacuo to afford an oil Chromatography (SiO$_2$; 100% EtOAC-10% EtOH/EtOAc) afforded the title compound as a viscous oil (11 g, 89%). δH (CDCl$_3$) 9.71 (1H, s), 8.70 (1H, d, J 5. Hz), 7.50 (1H, d, J 5.8 Hz), 7.31–7.28 (4H,m), 7.11 (1H, s), 4.23 (2H, q, J 7.1 Hz), 3.79–3.72 (1H, m), 3.14 (1H, dd, J 14.1, 5.4 Hz), 2.94 (1H, dd, J 14.1, 7.8 Hz), 2.47 (3H, s), 1.75–1.50 (2H, br s) and 1.30 (3H, t, J 7.1 Hz); m/z (ES$^+$, 70V) 352 (MH$^+$).

Intermediate 16

3-Trifluoromethyl-2,7-naphthyridone

To a rapidly stirred suspension of 4-methylnicotinic acid HCl (952 mg, 5.48 mmol) in THF (25 ml) at −78° was added n-butyl lithium (17.0 mmol) over 20 min, maintaining the temperature below −50°. The reaction was maintained at −78° for 1.5 h, the temperature raised to −30° and after 40 min CO$_2$ gas bubbled through the solution for 10 min maintaining the temperature between −30 to −20°. The reaction was then allowed to warm to ambient temperature, poured into water (30 ml) and to this was added 1M HCl (30 ml). The solution was washed with DCM (2×20 ml) and the aqueous layer concentrated in vacuo at a temperature below 50° to give crude 4-(carboxymethyl)nicotinic acid as a brown oil. m/z (ES$^+$, 70V) 182 (MH$^+$). The brown oil was dissolved in trifluoroacetic anhydride (15 ml) and after 10 min heated at 100° in a sealed tube for 4 days. The solvent was removed under vacuum and the resulting crude 3-(trifluoromethyl)-1H-pyrano[3,4-C]pyridin-1-one, m/z (ES$^+$, 70V) 216 (MH$^+$) dissolved in concentrated NH$_4$OH (10 ml) and heated at 100° for 1 h, additional concentrated NH$_4$OH (10 ml) added after 20 and 40 minutes. The reaction was allowed to cool to ambient temperature, and the pale brown aqueous solution separated. The organic layer was separated and concentrated in vacuo to yield a brown/orange oily solid purified by column chromatography (SiO$_2$:EtOAC) to give the title compound (957 mg, 82%) as a pale yellow solid. δH (DMSO-d$^6$) 9.24 (1H, s), 8.71 (1H, d, J 5.4 Hz), 7.65 (1H, d J 5.4 Hz), 7.11 91H, s), 3.19 (1H, br s). m/z (ES$^+$, 70V), 215 (MH$^+$).

Intermediate 17

3-Trifluoromethyl)-1-chloro-2,7-naphthyridine

Intermediate 16 (892 mg) was heated at 125° for 5 h in POCl$_3$ (10 ml). The solvent was removed in vacuo to give a brown/orange solid which was suspended in rapidly stirring, ice-cooled DCM (30 ml). Saturated, ice-cooled NaHCO$_3$ (20 ml) was rapidly added to the stirring suspension, the DCM layer separated, the aqueous layer was then extracted with DCM (3×20 ml). The combined DCM layers were washed with saturated brine, dried (MgSO$_4$) and concentrated in vacuo to give the crude title compound (343 mg) contaminated with starting material. δH (DMSO-d$^6$) 9.78 (1H, s), 9.04 (1H, d, J 5.7 Hz), 8.64 (1H, s), 8.20 (1H, d, J 5.6 Hz). m/z (ES$^+$, 70V) 233 (MH$^+$).

Intermediate 18

Ethyl-(S)-3-{4-[(3-trifluoromethyl)-2,7-naphthyridin-1-yloxy]phenyl}-2-[t-butoxycarbonylamino]propanoate To N-tBOC-(S)-tyrosine ethyl ester (296 mg, 0.96 mmol) in DMF (5 ml) were added caesium carbonate (328 mg, 1.01 mmol) and crude Intermediate 17 (234 mg, 1.01 mmol). The reaction was heated at 45° for 18 h then 7 h at 60°. The solvent was removed in vacuo and the residue purified by chromatography (SiO$_2$.30% EtOAc/Hexane) to give the title compound (288 mg, 60%) as a pale yellow glass. δH (CD$_3$OD) 7.64 (1H, s), 8.72 (1H, d, J 5.8 Hz), 7.85 (1H, d, J 5.8 Hz), 7.80 (1H, s), 7.19 (2H, d, J 8.6 Hz), 7.12 (2H, d, J 8.6 Hz), 4.24 (1H, m), 3.98 (2H, q, J 7.1 Hz), 2.99 (1H, dd, J 13.7, 6.1 Hz), 2.84 (1H, dd, J 13.7, 8.6 Hz), 1.25 (9H, s), 1.06 (3H, t, J 7.1 Hz). m/z (ES$^+$, 70V) 528 (MNa$^+$).

Intermediate 19

1-Chloro-3-ethyl-2,7-naphthyridine

Prepared in a similar manner to the compound of Intermediate 9. δH (DMSO-d$^6$) 9.65 (1H, s), 8.88 (1H, d, J 5.7 Hz), 7.99 (1H, d, J 5.7 Hz), 7.82 (1H, s), 2.97 (2H, q, J 7.5 Hz), 1.39 (3H, t, J 7.5 Hz); m/z (ES+70V) 193 (MH$^+$).

Intermediate 20

1-Chloro-3-iso-butyl-2,7-naphthyridine

The title compound was prepared in a similar manner to the compound of Intermediate 9. δH (CDCl$_3$) 9.68 (1H, s), 8.75 (1H, d, J 5.7 Hz), 7.59 (1H, d, J 5.7 Hz), 7.37 (1H, s), 2.78 (2H, d, J 7.2 Hz), 2.25 (1H, septet, J 6.7 Hz) and 0.96 (6H, d, J 6.7 Hz); m/z (ES$^+$, 70V) 221 and 223 (MH$^+$).

Intermediate 21

Ethyl 3-[4-(3-methyl-2,7-naphthyridin-1-ylamino) phenyl]-3-(t-butyloxy-carbonylamino)propanoate The compound of Intermediate 9 (1.5 g, 8.4 mmol) was added to a solution of ethyl-3-(4-aminophenyl)-3-(t-butyloxycaronylamino)propanoate (2.59 g, 8.4 mmol) [prepared according to the methods of International Patent Application WO 00/32575] in 2-ethoxyethanol (20ml) and heated to 100° for 5 h. The mixture was concentrated in vacuo to give a dark brown solid that was used without further purification.

Intermediate 22

Ethyl 3-[4-(3-methyl-2,7-naphthyridin-1-ylamino) phenyl]-2-amino Propanoate

The compound of Intermediate 21 was treated with a 3M solution of HCl in EtOAc for 2 min. The mixture was then concentrated in vacuo and used without further purification.

EXAMPLE 1

Ethyl (S)-3-[4-(2,7-naphthyridin-1-ylamino)phenyl]-2-[2-isopropoxy-3,4-dioxocyclobut-1-enylamino] propanoate A solution of Intermediate 4 (410 mg, 1.22 mmol) and 1,2-diisopropoxy-3,4-dioxocyclobut-1-ene (290 mg, 1.46 mmol) in absolute ethanol (20 ml) was stirred at 50° overnight. The ethanol was removed in vacuo and replaced with isopropanol (10 ml) and the reaction mixture heated at 70° for 5 h. The volatiles were removed in vacuo and the residue chromatographed (silica; 2 to 5% MeOH/DCM) affording the title compound a straw-colored foam (455 mg, 79%). δH (CDCl$_3$) 9.43 (1H, s), 8.65 (1H, d, J 5.6 Hz), 8.19 (1H, d, J 5.7 Hz), 7.66 (2H, d, J 8.4 Hz), 7.65 (1H, masked s), 7.52 (1H, d, J 5.6 Hz), 7.13 (2H, d, J 8.4 Hz), 7.03 (1H, d, J 5.7 Hz), 6.72, 6.01, 5.18 and 4.63 (together 1H, br m), 5.36 (1H, m), 4.26 (2H, q, J 7.1 Hz), 3.29–3.08 (2H, br m), 1.41 (3H, d, J 7.1 Hz), 1.40 (3H, d, J 7.1 HZ) and 1.31 (3H, t, J 7.1 Hz); m/z (ES$^+$, 70V) 475 (MH$^+$).

EXAMPLE 2

Ethyl (S)-3-[4-(2,7-naphthyridin-1-ylamino)phenyl]-2-[2-ethoxy-3,4-dioxocyclobut-1-enylamino] propanoate Prepared from Intermediate 4 and 1,2-diethoxy-3,4-dioxocyclobut-1-ene in a similar manner to Example 1 to give the title compound (1.14 g, 90%) as a yellow glass. δH (CD$_3$OD) 9.45 (1H, s), 8.37 (1H, d, J 5.7 Hz), 7.90 (1H, d, J 5.8 Hz), 7.46 (3H, m), 7.04 (2H, d, J 8.4 Hz), 6.90 (1H, d, J 5.9 Hz), 4.90, 4.50 (1H, sxm), 4.48 (2H, m), 4.06 (2H, m), 3.14 (1H, m), 2.80 (1H, m), 1.22 (3H, t), 1.11 (3H, t); m/z (ES$^+$, 70V, 461 (MH$^+$).

EXAMPLE 3

Ethyl (S)-3-[4-(2,7-naphthyridin-1-ylamino)phenyl]-2-[(2-N,N-diethylamino-3,4-dioxocyclobut-1-enyl) amino]propanoate A solution of the compound of Example 1 (305 mg, 0.64 mmol) and diethylamine (0.193 μl, 136 mg, 1.86 mmol) in ethanol (10 ml) was stirred at 50° for 18 h. The volatiles were removed in vacuo and the residue chromatographed (silica; 3% EtOH/EtOAc) to afford the title compound as a pale yellow foam (290 mg, 93%). δH (DMSO-d$^6$, 340K), 9.82 (1H, s), 9.38 (1H, s), 8.65 (1H, d, J 5.6HZ), 8.16 (1H, d, J 5.7 Hz), 7.78 (2H, d, J 8.55 Hz), 7.65 (1H, d, J 5.7 Hz), 7.45 (1H, br s), 7.24 (2H, d, J 8.6 Hz), 7.10 (1H, d, J 5.75 Hz), 5.22 (1H, narrow m), 4.19 (2H, q, J 7.1 Hz), 3.55 (4H, q, J 7.1 Hz), 3.25 (1H, dd, J 14.1,5.0 Hz), 3.06 (1H, dd, J 14.1, 4.11 Hz), 1.24 (3H, t, J 7.09 Hz) and 1.14 (6H, t, J 7.13 Hz); m/z (ES$^+$, 70V) 488 (MH$^+$).

EXAMPLE 4

(S)-3-[4-(2,7-Naphthyridin-1-ylamino)phenyl]-2-[2-N,N-diethylamino-3,4-dioxocyclobut-1-enylamino] propanoic Acid The compound of Example 3 (290 mg, 0.06 mmol) was treated with LiOH.H$_2$O (39 mg, 0.093 mmol) in dioxan (3 ml) and water (3 ml) at room temperature for 1.5 h. The volatiles were removed in vacuo and the residue chromatographed [silica; DCM (200 to 120) MeOH (20), AcOH (3), H$_2$O (2)] to afford a yellow oil, that was freeze-dried from aqueous methanol to give the title compound as a bright yellow amorphous powder (198 mg, 71%). δH (d$_6$ DMSO, 350K) 9.81 (1H, s), 9.34 (1H, br s), 8.64 (1H, d, J 5.6 Hz), 8.15 (1H, d, J 5.7 Hz), 7.77 (2H, d, J 8.3 Hz), 7.64 (1H, dd, J 5.6, 0.9 Hz), 7.30 (1H, br d, J 8.0 Hz), 7.24 (1H, d, J 8.3 Hz), 7.09 (1H, d, J 5.7 Hz), 5.14–5.10 (1H, m), 3.60–3.49 (4H, m), 3.26 (1H, dd, J 14.1, 4.8 Hz), 3.08 (1H, dd, J 14.1, 9.7 Hz), 1.15 (6H, t, J 7.1 Hz); m/z (ES$^+$, 70V) 460 (MH$^+$).

EXAMPLE 5

(S)-3[4-(2,7-Naphthyridin-1-ylamino)phenyl]2-[2-N,N-di-n-propylamino-3,4-dioxocyclobut-1-enylamino]propanoic Acid Prepared in a similar manner to the compound of Example 4 from the compound of Example 1 and dipropylamine to give the title compound. δH (d$_6$ DMSO, 350K) 9.81 (1H, s), 9.37 (1H, br s), 8.64 (1H, d, J 5.6HZ), 8.15 (1H, d, J 5.6 Hz), 7.77 (2H, d, J 8.2 Hz), 7.62 (1H, dd, J 5.6, 0.8 Hz), 7.29 91H, d, J 7.1 Hz), 7.22 (2H, d, J 8.2 Hz), 7.10 (1H, d, J 5.6 Hz), 5.11–5.07 (1H, narrow m), 3.58–3.46 (2H, m), 3.44–3.37 (2H, m), 3.26 (1H, dd, J 14.0, 4.7 Hz), 3.08 (1H, dd, J 14.0, 9.7 Hz), 1.58–1.49 (4H, m), 0.85 (6H, t, J 7.3 Hz); m/z (ES$^+$, 70V) 488 (MH$^+$).

EXAMPLE 6

(S)-3-[4-(2,7-Naphthyridin-1-ylamino)phenyl]-2-[2-(cis-2,5-dimethylpyrrolidin-1-yl)-3,4-dioxocyclobut-1-enylamino]propanoic Acid Prepared in a similar manner to the compound of Example 4 from the compound of Example 1 and cis-2,5-dimethylpyrrolidine to give the title compound. δH (DMSO-d$^6$) 9.82 (1H, s), 9.52 (1H, S), 8.65 (1H, d, J 5.6 Hz), 8.16 (1H, d, J 5.7 Hz), 7.76 (2H, d, J 8.5 Hz), 7/68 (1H, d, J 5.6 Hz), 7.53 (1H, d, J 7.0 Hz), 7.24 (1H, d, J 8.5 Hz), 7.12 (1H, d, J 5.7 Hz), 5.06 (1H, m), 4.18 (2H, m), 3.24 (1H, dd, J 13.0, 4.1 Hz), 3.04 (1H, dd, J 13.9, 10.7 Hz), 2.08 (2H, m), 1.67 (2H, m), 1.25 (3H, d, J 6.4 Hz) and 1.21 (3H, d, J 6.3 Hz); m/z (ES$^+$, 70V) 486 (MH$^+$).

EXAMPLE 7

Ethyl (S)-3-[4-(2,7-naphthyridin-1-ylamino)phenyl]-2-[2-(2-methyl-piperidin-1-yl)-3,4-dioxocyclobut-1-enylamino]propanoate Prepared in a similar manner to the compound of Example 3 from the compound of Example 1 and 2-methylpiperidine to give the title compound δH (DMSO-d$^6$) 9.81 (1H, s), 9.51 (1H, s), 8.64 (1H, d, J 5.6 Hz), 8.14 (1H, d, J 5.8 Hz), 7.89–7.76 (3H, m), 7.67 (1H, d, J 5.53 Hz), 7.22–7.19 (2H, m), 7.11 (1H, d, J 5.8 Hz), 5.16 (1H, m), 4.45 (1H, m), 4.15 (2H, d, J 7.1 Hz), 4.1–3.9 (2H, m), 3.2–2.9 (2H, m), 1.7–1.3 (6H, m) and 1.3–1.1 (6H, m). m/z (ES$^+$, 70V) 514 (MH$^+$).

EXAMPLE 8

(S)-3-[4-(2,7-Naphthyridin-1-ylamino)phenyl]-2-[2-(2-methyl piperidin-1-yl)-3,4-dioxocyclobut-1-enylamino]propanoic Acid Prepared in a similar manner to the compound of Example 4 from the compound of Example 7. δH (DMSO-d$^6$, 350K), 9.87 (1H, s), 9.39 (1H, s), 8.70 (1H, d, J 5.6 Hz), 8.21 (1H, d, J 5.6 Hz), 7.83 (2H, d, J 8.4 Hz), 7.7 (1H, d, J 5.6 Hz), 7.48 (1H, d, J 7.6 Hz), 7.20 (2H, d, J 8.5 Hz), 7.14 (1H, d, J 5.7 Hz), 5.18 (1H, m), 4.51 (1H, m), 4.10 (1H, m), 3.36–3.07 (2H, m), 3.1–2.9 (1H, m), 1.87–1.47 (6H, m) and 1.29 (3H, d, J 6.85 Hz); m/z (ES$^+$, 70V); 486 (MH$^+$).

EXAMPLE 9

Ethyl (S)-3-[4-2,7-naphthyridin-1-ylamino)phenyl]-2-[(2-pyrrolidin-1-yl-3,4-dioxocyclobut-1-enyl)amino]propanoate Prepared in a similar manner to the compound of Example 3 from the compound of Example 1 and pyrrolidine to give the title compound as an orange solid. δH (CDCl$_3$) 9.43 (1H, br s), 8.66 (1H, d, J 5.6 Hz), 8.20 (1H, d, J 5.7 Hz), 7.69–7.51 (4H, m), 7.10 (2H, d, J 8.4 Hz), 7.04 (1 H, d, J 5.7 Hz), 5.49 (1H, br m), 5.33–5.30 (1H, m), 4.23 (2H, q, J 7.0 Hz), 3.75–3.63 (4H, br m), 3.25–3.20 (2H, m), 1.98–1.93 (4H, m) and 1.23 (3H, t, J 7.0 Hz). m/z (ES$^+$, 70V) 487 (MH$^+$).

EXAMPLE 10

(S)-3-[4-(2,7-Naphthyridin-1-ylamino)phenyl]-2-[(2-pyrrolidin-1-yl-3,4-dioxocyclobut-1-enyl)amino]propanoic Acid Prepared in a similar manner to the compound of Example 4 from the compound of Example 9. δH (DMSO-d$^6$), 9.82 (1H, s), 9.38 (1H, br s), 8.64 (1H, d, J 5.6 Hz), 8.15 (1H, d, J 5.7 Hz), 7.75 (2H, d, J 8.3 Hz), 7.64 (1H, d, J 5.6 Hz), 7.35 (1H, br s), 7.23 (2H, d, J 8.4 Hz), 7.08 (1H, d, J 5.7 Hz), 4.94–4.92 (1H, m), 3.68–3.62 (4H, m), 3.27–3.20 (1H, m), 3.11–3.06 (1H, m), 1.92 (3H, s) and 1.89–1.86 (4H, m). (ES$^+$, 70V) 458 (MH$^+$).

EXAMPLE 11

Methyl (S)-3-[4-(2,7-naphthyridin-1-ylamino) phenyl]-2-[2-(2-methylpyrrolidin-1-yl)-3,4-dioxocyclobut-1-enylamino]propanoate Prepared in a similar manner to the compound of Example 3 from the compound of Example 1 and 2-methylpyrrolidine. δH (DMSO-d$^6$) 9.88 (1H, s), (9.59 (1H, s), 8.72 (1H, d, J 5.6 Hz), 8.21 (1H, d, J 4.7 Hz), 7.86 (3H, m), 7.29 (2H, d, J 8.3 Hz), 7.18 (1H, d, J 5.8 Hz), 5.20 (1H, m), 4.29 (1H, m), 3.89 (1H, m), 3.60 (1H, m), 3.35 (3H, s), 3.31 (1H, m), 3.01 (1H, m), 2.05 (3H, br m), 1.67 (1H, m) and 1.17 (3H, br m). m/z (ES$^+$, 70V) 486 (MH$^+$).

EXAMPLE 12

(S)-3-[4-(2,7-Naphthyridin-1-ylamino)phenyl]-2-[2-(2-methylpyrrolidin-1yl)-3,4-dioxocycylobut-1-enylamino]propanoic Acid Prepared in a similar manner to the compound of Example 4 from the compound of Example 11. δH (DMSO-d$^6$), 9.88 (1H, s), 9.58 (1H, m), 8.71 (1H, d, J 5.6 Hz), 8.21 (1H, d, J 7.1 Hz), 7.84–7.74 (3H, m), 7.29 (2H, d, J 8.5 Hz), 7.18 (1H, d, J 5.8 Hz), 5.13 (1H, m), 4.33 (1H, m), 3.89 (1H, m), 3.57 (1H, m), 3.27 (1H, m), 3.06 (1H, m), 2.09–1.92 (3H, br m), 1.68 (1H, m) and 1.18 (3H, br m). m/z (ES$^+$, 70V) 472 (MH$^+$).

EXAMPLE 13

Ethyl (S)-3-[4-(2,7-naphthyridin-1-ylamino)phenyl]-2-[2-(trans-2,5-dimethyl pyrrolidin-1-yl)-3,4-dioxocyclobut-1-enylamino]propanoate Prepared in a manner similar to Example 3 from the compound of Example 1 and trans-2,5-dimethylpyrrolidine to give the title compound as a pale yellow solid. δH (DMSO-d$^6$, 340K), 9.82 (1H, s), 9.38 (1H, s), 8.64 (1H, d, J 5.6 Hz), 8.16 (1H, d, J 5.7 Hz), 7.79 (2H, d, J 8.6 Hz), 7.65 (1H, d, J 5.7 Hz), 7.41 (1H, d, J 8.9 Hz), 7.24 (2H, d, J 8.6 Hz), 7.11 (1H, d, J 5.6 Hz), 5.22 (1H, m), 4.38 (2H, m), 4.21 (1H, m), 4.17 (2H, q, J 7,0 Hz), 3.48 (1H, m), 3.26 (1H, dd, J 14.3, 5.5 Hz), 3.14 (1H, dd, J 14.3, 9.5 Hz), 2.14 (2H, m), 1.59 (2H, m), 1.22 (3H, t, J 7.1 Hz) and 1.10 (6H, d, J 6.5 Hz) m/z (ES$^+$, 70V) 514 (MH$^+$).

EXAMPLE 14

(S)-3-[4-(2,7-Naphthyridin-1-ylamino)phenyl]-2-[2-(trans-2,5-dimethylpyrrolidin-1-yl)-3,4-dioxocyclobut-1-enylamino]propanoic Prepared in a manner similar to Example 4 from the compound of Example 13 to give the title compound as a pale yellow solid. δH (DMSO-d$^6$, 340K), 9.81 (1H, s), 9.37 (1H, s), 8.64 (1H, d, J 5.8 Hz), 8.15 (1 H, d, J 5.8 Hz), 7.76 (2H, d, J 8.6 Hz), 7.64 (1H, d, J 5.8 Hz), 7.23 (2H, d, J 8.6 Hz), 7.10 (1H, d, J 5.8 Hz), 5.08 (1H, m), 4.36 (2H, m), 3.24 (1H, m), 3.08 (1H, m), 2.15 (2H, m), 1.59 (2H, m), 1.11 (6H, d, J 6.5 Hz). m/z (ESI, 70V) 486 (MH$^+$).

EXAMPLE 15

Ethyl-(S)-3-[4-(2,7-naphthyridin-1-ylamino)phenyl]-2-[2-piperidin-1-yl-3,4-dioxocyclobut-1-enylamino] propanoate Prepared in a similar manner to the compound of Example 3 from the compound of Example 1 and piperidine. δH (CDCl₃), 9.89 (1H, s), 9.59 91H, s), 8.71 (1H, d, J 5.6 Hz), 8.22 (1H, d, J 5.7 Hz), 7.82 (2H, m), 7.75 (1H, d, J 5.6 Hz), 7.28 (2H, d, J 8.5 Hz), 7.19 (1H, d, J 5.7 Hz), 5.22 (1H, dd, J 10.5, 4.7 Hz), 4.26–4.20 (2H, m), 3.28 (1H, dd, J 4,7 4.7 Hz), 3.07 (1H, dd, J 13.8, 10.6 Hz), 2.56 (4H, m), 1.80–1.51 (6H, m) and 1.28 (3H, t, J 7.1 Hz), m/z (ES⁺, 70V) 500 (MH⁺).

EXAMPLE 16

(S)-3-[4-(2,7-Naphthyridin-1-ylamino)phenyl]-2-[2-piperidin-1-yl-3,4 -dioxocyclobut-1-enylamino] propanoic Acid Prepared in a similar manner to the compound of Example 4 from the compound of Example 15. δH (DMSO-d⁶), 9.86 (1H, s), 9.44 (1H, s), 8.65 (1H, d, J 5.6 Hz), 8.16 (1H, d, J 5.7 Hz), 7.97–7.77 (2H, m), 7.67–7.64 (2H, m), 7.24–7.21 (2H, m), 7.13 (1H, d, J 5.7 Hz), 5.02 (1H, br s), 3.63 (4H, br s), 3.23 (1H, dd, J 13.9, 4.2 Hz), 3.02 (1H, dd, J 13.9, 4.49 Hz) and 1.68 -1.52 (6H, m). m/z (ES⁺, 70V) 472 (MH⁺).

EXAMPLE 17

Ethyl-(S)-3-[4-(2,7-naphthyridin-1-ylamino)phenyl]-2-[2-(azepan-1-yl)-3,4-dioxocyclobut-1-enylamino] propanoate Prepared from the compound of Example 2 in a manner similar to that for the compound of Example 3 and azepane to give the title compound as a yellow glass. δH (CD₃OD) 9.66 (1H, s), 8.59 (1H, d, J 5.7 Hz), 8.12 (1H, d, J 5.8 Hz), 7.69 (3H, m), 7.27 (2H, d, J 8.4 Hz), 7.11 (1H, d, J 5.7 Hz), 5.35 (1H, m), 4.28 (2H, q, J 7.2 Hz), 4.1–3.5 (4H, 2 x br), 3.41 (1H, dd, J 14.0, 4.7 Hz), 3.08 (1H, dd, J 14.0, 10.6 Hz), 1.74 (4H, br s), 1.59 (4H, br s), 1.33 (3H, t, J 7.1 Hz). m/z (ES⁺, 70V) 514 (MH⁺).

EXAMPLE 18

(S)-3-[4-(2,7-Naphthyridin-1-ylamino)phenyl]-2-[2-(azepan-1-yl)-3,4 -dioxocyclobut-1-enylamino] proanoic Acid Prepared from the compound of Example 17 in a similar manner to Example 4 to give the title compound as a yellow solid. δH (DMSO-d⁶, 350K) 9.83 (1H, s), 9.35 (1H, s), 8.66 (1H, d, J 5.6 Hz), 8.17 (1H, d, J 5.7 Hz), 7.79 (2H, d, J 8.3 Hz), 7.66 (1H. d, J 5.7 Hz), 7.30 (1H, d, J 7.25 Hz), 7.25 (2H, d, J 8.6 Hz), 7.11 (1H, d, J 5.6 Hz), 5.14 (1H, m), 3.67 (4H, m), 3.27 (1H, dd, J 14.2, 5.0 Hz), 3.10 (1H, dd, J 14.2, 9.8 Hz), 1.68 (4H, br), 1.54 (4H, m). m/z (ES⁺, 70V) 486 (MH⁺).

EXAMPLE 19

Methyl (S)-3-[4-(2,7-naphthyridin-1-yloxy)phenyl]-2-[2-isopropoxy-3,4-dioxocyclobut-1-enyl] propanoate A solution of Intermediate 6 (870 mg, 2.69 mmol) and 1,2-diisopropoxy-3,4-dioxocyclobut-1-ene (587 mg, 2.96 mmol) in methanol (10 ml) was stirred at 70° for 18 h. The volatiles were removed in vacuo and the obtained oil chromatographed (SiO₂; 50% EtOAc/Hexane-100% EtOAc) to afford the title compound as a white foam (850 mg, 68%). δH (CDCl₃) 9.79 (1H, s), 8.78 (1H, d, J 5.7 Hz), 8.11 (1H, d, J 5.8 Hz), 7.61 (1H, d, J 5.8 Hz), 7.28 (1H, d, J 5.9 Hz), 7.28–7.22 (5H, m), 6.44, 5.89, 5.20 and 4.66 (together 1H, br s), 5.38 (1H, m), 3.82 (3H, s), 3.34–3.13 (2H, br m), 1.43 (3H, d, J 6.2 Hz) and 1.41 (3H, d, J 6.2 Hz); m/z (ES⁺, 70V) 462 (MH⁺).

EXAMPLE 20

Ethyl-(S)-3-[4-(2,7-naphthyridin-1-yloxy)phenyl]-2-[2-ethoxy-3,4-dioxocyclobut-1-enylamino] propanoate A solution of N-tbutoxycarbonyl-(S)-tyrosine ethyl ester (5 g, 16.2 mmol) in DMF (80 ml) was treated with caesium carbonate (5.36 g) and the compound of Intermediate 3 (2.7 g) and stirred at room temperature for 16 h then concentrated and purified by chromatography (SiO₂; EtOAc). The product was dissolved in EtOAc and treated with excess HCl gas and the white precipitate isolated by filtration and dried, dissolved in ethanol (100 ml) and treated with Hunigs base (5.94 ml), 1,2-diethyoxy-3,4-dioxocyclobut-1-ene and stirred at room temperature for 16 h. The solution was concentrated in vacuo then purified by chromatography (SiO₂; EtOAc/hexane 1:4–1:2) to give the title compound (4.5 g, 60%) as a white foamy solid. δH (DMSO-d⁶, 350K), 9.71 (1H, s), 8.81 (1H, d, J 5.8 Hz), 8.15 (1H, d, J 5.8 hz), 7.86 (1H, dd, J 8.1, 1.0 Hz), 7.53 (1H, dd, J 5.8, 1.0 Hz), 7.36 (2H, d, J 8.7 Hz), 7.26 (2H, d, J 8.7 Hz), 4.65 (2H, qd, J 7.1, 1.1 Hz), 4.20 (2H, q, J 7.05 Hz), 3.31 (1H, dd, J 14.1, 5.1 Hz), 3.11 (1H, dd, J 14.1, 9.8 Hz), 1.39 (3H, t, J 7.05 Hz) and 1.24 (3H, t, J 7.1 Hz). m/z (ES⁺, 70V) 462 (MH⁺).

EXAMPLE 21

(S)-3-([4-(2,7-Naphthyridin-1-yloxy)phenyl]-2-[2-(cis-2,5-dimethylpyrrolidin-1-yl)-3,4-dioxocyclobut-1-enylamino]propanoic A solution of the compound of Example 19 (250 mg, 0.54 mmol) and 2,5-dimethylpyrrolidine (cis/trans mixture 107 mg, 1.08 mmol) in methanol (5 ml) was stirred at 40° for 2 days. The volatiles were removed in vacuo and the obtained residue chromatographed (silica; 2% MeOH/DCM) to afford the methyl ester of the title compound as a pale yellow foam (250 mg). This material was treated with LiOH.H₂O (30 mg) in dioxan (3 ml) and water (4 ml) at room temperature for 1 h. A few drops of AcOH were added and the volatiles were removed in vacuo. The residue was chromatographed [silica; DCM (200), MeOH (20), AcOH (3), H₂O(2)] to afford an oil which was freeze-dried from aqueous methanol to afford the title compound as a pale yellow amorphous solid (140 mg). δH (DMSO-d⁶), 9.69 (1H, s), 8.81 (1H, d, J 5.7 Hz), 8.14 (1H, d, J 5.8 Hz), 7.89 (1H, d, J 5.7 Hz), 7.58 (1H, d, J 9.0 Hz), 7.53 (1H, d, J 5.8 Hz), 7.37 (2H, d, J 8.6 Hz), 7.23 (2H, d, J 8.6 Hz), 5.10 (1H, m), 4.20 (2H, m), 3.32 (1H, dd, J 13.9, 4.2 Hz), 3.11 (1H, dd, J 13.9, 11.8 Hz), 2.09 (2H, m), 1.68 (2H, m) 1.27 (3H, d, J 6.4 Hz) and 1.21 (3H, d, J 6.3 Hz); m/z (ES⁺, 70V) 487 (MH⁺).

EXAMPLE 22

Ethyl (S)-3-[4-(2,7-naphthyridin-1-yloxy)phenyl]-2-[2-N,N-diethylamino-3,4-dioxocyclobut-1-enylamino]propanoate A solution of the compound of Example 19 in EtOH (100 ml) was treated with diethylamine (1.6 ml) and stirred at room temperature for 16 h, concentrated in vacuo, then purified by chromatography (SiO₂; EtOAC/hexane;9–2:1) to give the title compound (2.84 g, 77%) as a white solid. δH (DMSO-d⁶, 350K), 9.69 (1H, s), 8.79 (1H, d, J 5.8 Hz), 8.13 (1H, d, J 5.8 Hz), 7.84 (1H, dd, J 5.8,1.0 Hz), 7.50 (1H, dd, J 5.8, 0.7 Hz), 7.35 (2H, d, J 8.6 Hz), 7.23 (2H, d, J 8.6 Hz), 5.22 (1H, dd, J 9.8, 5.3 Hz), 4.20 (2H, qd, J 7.0, 1.0 Hz), 3.55 (4H, 1, J 7.1 Hz), 3.30 (1H, dd, J 14.0, 5.3 Hz), 3.16 (1H, dd, J 14.1, 9.8 Hz), 1.24 (3H, t, J 7.1 Hz) and 1.15 (6H, t, J 7.1 Hz). m/z (ES$^+$, 70V) 489 (MH$^+$).

EXAMPLE 23

(S)-3-[4-(2,7-Naphthyridin-1-yloxy)phenyl]-2-[2-N, N-diethylamino-3,4-dioxocyclobut-1-enylamino]-propanoic Acid Prepared in a similar manner to the compound of Example 21 from the compound of Example 22 to give the title compound as a pale yellow amorphous solid. δH (DMSO-d$^6$), 9.69 (1H, s), 8.80 (1H, d, J 5.7 Hz), 8.14 (1H, d, J 5.8 Hz), 7.86 (1H, d, J 5.7 Hz), 7.52 (1H, d, J 5.8 Hz), 7.42 (1H, d, J 9.0 Hz), 7.36 (2H, d, J 8.6 Hz), 7.24 (2H, d, J 8.6 Hz), 5.17 (1H, m), 3.60 -3.46 (4H, m), 3.32 (1H, dd, J 14.0, 4.6 Hz), 3.13 (1H, dd, J 14.0, 10.1 Hz) and 1.15 (5H, t, J 7.1 Hz); m/z (ES$^+$) 461 (MH$^+$).

EXAMPLE 24

(S)-3-[4-(2,7-Naphthyridin-1-yloxy)phenyl]-2-[2-(N, N-di-n-propylamnino)-3,4-dioxocyclobut-1-enylamino]propanoic Acid Prepared in a similar manner to the compound of Example 21 from the compound of Example 19 and dipropylamine to give the title compound as a pale yellow amorphous solid. δH (DMSO-d$^6$), 9.68 (1H, s), 8.80 (1H, d, J 5.7 Hz), 8.13 (1H, d, J 5.8 Hz), 7.86 (1H, d, J 5.7 Hz), 7.52 (1H, d, J 5.8 Hz), 7.36 (1H, masked d), 7.36 (2H, d, J 8.5 Hz), 7.23 (2H, d, J 8.5 Hz), 5.17 (1H, m), 3.58–3.39 (4H, m), 3.33 (1H, dd, J 14.0, 4.7 Hz), 3.13 (1H, dd, J 14.0, 10.1 Hz), 1.63–1.48 (4H, m) and 0.85 (6H, t, J 7.3 Hz); m/z (ES$^+$, 70V)489 (MH$^+$).

EXAMPLE 25

Ethyl (S)-3-[4-(2,7-naphthyridin-1-yloxy)phenyl]-2-[2-azepan-1-yl-3,4-dioxocyclobut-1-enylamino]propanoate Prepared in a manner similar to the compound of Example 21 from the compound of Example 20 and azepane to give the title compound as a white solid. δH (DMSO-d$^6$), 9.81 (1H, s), 8.94 (1H, d, J 5.7 Hz), 8.25 (1H, d, J 5.7 Hz), 8.01 (1H, dd, J 5.7, 0.9 Hz), 7.66 (1H, d, J 5.7 Hz), 7.44 (2H, d, J 8.6 Hz), 7.35 (2H, d, J 8.6 Hz), 5.32 (1H, dd, J 10.8, 4.9 Hz), 4.30 (2H, q, J 7.0 Hz), 3.79 (4H, m), 3.43 (1H, dd, J 14.0, 4.9 Hz), 3.22 (1H, dd, J 14.0, 10.8 Hz), 1.92 (4H, m), 1.61 (4H, m) and 1.35 (3H, t, J 7.1 Hz). m/z (ES$^+$. 70V) 515 (MH$^+$).

EXAMPLE 26

(S)-3-[4-(2,7-Naphthyridin-1-yloxy)phenyl]-2-[2-(azepan-1-1yl)-3,4-dioxocyclobut-1-enylamino]propanoic Acid A solution of the compound of Example 25 in THF (4 ml) and water (4 ml) was treated with lithium hydroxide (4 mg) and stirred at room temperature for 30 min. The THF was removed and the solution acidified to pH 2 with dilute hydrochloric acid solution and the precipitate isolated by filtration to give the title compound (97 mg, 32%) as a pale yellow solid. δH (DMSO-d$^6$, 350K), 9.70 (1H, d, J 0.8 Hz), 8.81 (1H, d, J 5.8 Hz), 8.16 (1H, d, J 5.8 Hz), 7.86 (1H, dd, J 5.8, 1.0 Hz), 7.52 (1H, dd, J 8.0, 0.8 Hz), 7.36 (2H, d, J 8.6 Hz), 7.24 (2H, d, J 8.6 Hz), 5.17 (1H, m), 3.68 (4H, m), 3.33 (1H, dd, J 14.1, 10.0 Hz), 1.68 (4H, m) and 1.54 (4H, m). m/z (ES$^+$, 70V) 487 (MH$^+$).

EXAMPLE 27

Ethyl (S)-3-[4-(2,7-naphthyridin-1-yloxy)phenyl]-2-[(2-[(2S),(5S)-trans dimethylpyrrolidin-1-yl]-3,4-dioxocyclobut-1-enyl)amino]propanoate To a solution of the compund of Example 19 (0.25 g, 0.56 mmol) in methanol (3 ml) at room temperature was added (2S),(5S)-dimethylpyrrolidine trifluoroacetic acid salt (0.21 g, 1 mmol) and N,N-diisopropylethylamine (0.3 ml, 1.8 mmol). The mixture was heated to 50°. After 6 h at 50° extra (2S),(5S)-dimethylpyrrolidine trifluoroacetic acid salt (0.21 g, 1 mmol) and N,N-diisopropylethylamine (0.3 ml, 1.8 mmol) was added and the mixture heated to 70°. The reaction was stirred at this temperature overnight before (2S), (5S)-dimethylpyrrolidine trifluoroacetic acid salt (0.21 g, 1 mmol) and N,N-diisopropylethylamine (0.3 ml, 1.8 mmol) was added. The mixture was heated at 70° for a further 24 h, partitioned between ethyl acetate (40 ml) and water (30 ml). The organics were separated and washed with ammonium chloride (2×30 ml), water (30 ml), brine (30 ml), dried (MgSO$_4$), and concentrated in vacuo. Column chromatography (SiO$_2$; 23:2; DCM:MeOH) gave the title compound as an off white foam (0.19 g, 63%). δH (CDCl$_3$), 8.68 (1H, br), 8.12 (1H, m), 7.45 (1H, d, J 5.7 Hz), 7.29–7.08 (5H, m), 5.50 (2H, m), 3.85 (2H, d, J 7.1 Hz), 3.81 (3H, s), 3.37–3.30 (2H, m), 2.18–2.05 (2H, m), 1.76–1.65 (2H, m), 1.41–1.15 (6H, m). m/z (ES$^+$, 70V) 501 (MH$^+$).

EXAMPLE 28

(S)-3-[4-(2,7-Naphthyridin-1-ylamino)phenyl]-2-[2-[(2S), (5S)-dimethylpyrrolidin-1-yl]-3,4-dioxocyclobut-1-enyl)amino]proanoic Acid To a solution of the compound of Example 13 (0.17 g, 0.34 mmol) in THF (3 ml) at room temperature was added a solution of LiOH.H$_2$O (23 mg, 0.54 mmol) in water (1 ml). After 2 h the reaction mixture was concentrated in vacuo, redissolved in water (5 ml), acidified to pH 4 with acetic acid. The resulting white precipitate was isolated by filtration, washed with water. ether and dried in vacuo to give the product as an off white solid (80 mg, 47%) δH (DMSO-d$^6$), 9.42 (1H, s), 8.78 (1H, dd, J 6.2, 1.9 Hz), 8.13 (2H, m), 7.67 (1H, dd, J 5.7, 0.7 Hz), 7.37 (2H, m), 7.22 (2H, m), 5.12 (1H, m), 3.44–3.01 (4H, m), 2.16 (2H, m), 1.72 (0.5H, m), 1.62 (1.5H, m), 1.31 (1H, d, J 6.5 Hz), 1.26 (1H, d, J 6.4 Hz), 1.13 (2H, d, J 6.5 Hz) and 1.06 (2H, d, J 6.4 Hz). m/z (ES$^+$, 70V) 487 (MH$^+$).

EXAMPLE 29

Ethyl (S)-3-[4-(3-methyl-2,7-naphthyridin-1-ylamino)phenyl]-2-[2-ethoxy-3,4-dioxocyclobut-1-enylamino]propanoate A solution of Intermediate 11 (3.36 g, 9.6 mmol) and 1,2-diethoxy-3,4-dioxocyclobut-1-ene (1.63 g, 9.6 mmol) in absolute ethanol (30 ml) was stirred at room temperature for 14 h. The volatiles were removed in vacuo affording a yellow foam. Chromatography (silica: 50% EtOAc/Hexane-100% EtOAc) afforded the title compound as a yellow foam (4.28 g, 94%). δH (CDCl$_3$) 9.29 (1H, s), 8.54 (1H, d, J 5.7 Hz), 7.73 (2H, d, J 8.4 Hz), 7.43 (1H, masked br s), 7.42 (1H, d, J 5.7 Hz), 7.12 (2H, d, J 8.4 Hz), 6.88 (1H, s), 6.54, 5.98 and 5.16 (together 1H, br s), 4.60 (1H, br s), 4.77 (2H, br m), 4.33 (2H, q, J 7.1 Hz), 3.27–3.03 (2H, br m), 2.52 (3H, s), 1.43 (3H, t, J 7.1 Hz) and 1.32 (3H, t, J 7.2 Hz); m/z (ES$^+$, 70V) 475 (MH$^+$).

EXAMPLE 30

Ethyl (S)-3-[4-(3-methyl-2,7-naphthyridin-1-ylamino)phenyl]-2-[2-isopropoxy-3,4-dioxocyclobut-1-enylamino]propanoate The title compound was prepared in a similar manner to Example 29, from intermediate 11 and 1,2-diisopropoxy-3,4-dioxocyclobut-1-ene, and isolated as a light orange foam. δH (CDCl$_3$) 9.39 (1H, br s), 8.56 (1H, d, J 5.7 Hz), 7.77 (1H, masked br s), 7.76 (2H, d, J 7.9 Hz), 7.41 (1H, d, J 5.7 Hz), 7.11 (2H, d, J 8.4 Hz), 6.84 (1H, s), 6.36 and 5.18 (togehter 1H, br s), 5.41–5.20 (1H, br m), 4.63 (1H, br s), 4.29 (2H, q, J 7.1 Hz), 3.27–3.06 (2H, br m), 2.49 (3H, s), 1.42 (6H, d, J 6.1 Hz) and 1.32 (3H, t, J 7.1 Hz); m/z (ES$^+$, 70V) 489 (MH$^+$).

EXAMPLE 31

Ethyl (S)-3-[4-(3-methyl-2,7-naphthyridin-1-ylamino)phenyl]-2-[(2-(2-methylpiperidin-1-yl)-3,4-dioxocyclobut-1-enyl)amino]propanoate Prepared in a similar manner to the compound of Example 3 from the compound of Example 23 and 2-methylpiperidine to give the title compound. δH (DMSO-d$^6$); 9.75 (1H, s), 9.45 (1H, s), 8.56 (1H, d, J 5.5 Hz), 7.86 (2H, m), 7.56 (1H, d, J 5.6 Hz), 7.21 (2H, m), 6.96 (1H, s), 5.75 (1H, s), 5.18 (1H, m), 4.45 (1H, m), 4.18 (2H, m), 3.30–3.17 (3H, m), 3.02 (1H, dd, J 13.7, 10.1 Hz), 2.43 (3H, s), 1.78–1.32 (6H, m) and 1.22–1.14 (6H, m); m/z (ES$^+$, 70V) 528 (MH$^+$).

EXAMPLE 32

(S)-3-[4-(3-Methyl-2,7-naphthyridin-1-ylamino)phenyl]-2-[2-(methylpiperidin-1-yl)-3,4-dioxocyclobut-1-enylamino]propionic Acid Prepared in a similar manner to the compound of Example 4 from the compound of Example 31 to give the title compound as a yellow solid. δH (DMSO-d$^6$), 9.77 (1H, s), 9.46 (1H, s), 8.58 (1H, d, J 5.6 Hz), 7.90–7.78 (3H, m), 7.58 (1H, d, J 5.6 Hz), 7.25–7.22 (1H, m), 6.98 (1H, s), 5.14–5.08 (1H, m), 4.48 (1H, m), 4.05 (1H, m), 3.27–3.20 (2H, m), 3.04–2.95 (1H, m), 2.46 (3H, s), 1.74–1.44 (6H, m) and 1.23 (3H, d, J 6.8 Hz). m/z (ES$^+$, 70V) 500 (MH$^+$).

EXAMPLE 33

Ethyl (S)-3-[4-(3-methyl-2,7-naphthyridin-1-ylamino)phenyl]-2-[2-N,N-diethylamino-3,4-dioxocyclobut-1-enylamino]propanoate A solution of the compound of Example 30 (350 mg, 0.72 mmol) and diethylamine (157 mg, 222 μl, 2.15 mmol) in absolute ethanol (10 ml) was stirred at room temperature for 2 days. The volatiles were removed in vacuo and the obtained orange foam was chromatographed (silica; EtOAc) affording the title compound as a light yellow foam (301 mg, 84%). δH (DMSO-d$^6$, 350K) 9.61 (1H, s), 9.14 (1H, s), 8.42 (1H, d, J 5.6 Hz), 7.71 (2H, d, J 8.5 Hz), 7.39 (1H, d, J 5.6 Hz), 7.24 (1H, d, J 8.0 Hz), 7.09 (2H, d, J 8.5 Hz), 6.81 (1H, s), 5.08 (1H, m), 4.06 (2H, q, J 7.1 Hz), 3.41 (4H, q, J 7.1 Hz), 3.11 (1H, dd, J 14.1, 5.2 Hz), 2.96 (1H, dd, J 14.1, 9.7 Hz), 2.32 (3H, s), 1.10 (3H, t, J 7.1 Hz) and 1.02 (6H, t, J 7.1 Hz); m/m/z (ES$^+$, 70V) 502 (MH$^+$).

EXAMPLE 34

(S)-3-[4-(3-Methyl-2,7-naphthyridin-1-ylamino)phenyl]-2-[2-N,N-diethylamino-3,4-dioxocyclobut-1-enylamino]-propanoic Acid The compound of Example 33 (290 mg, 0.58 mmol) was treated with LiOH.H$_2$O (36 mg, 0.86 mmol) in dioxan (50 ml) and water (6 ml) at room temperatue for 1 h. A few drops of AcOH were added and the volatiles removed in vacuo. The residue was chromatographed [silica; DCM (200–120), MeOH (20), AcOH (3), H$_2$O (2)] affording a yellow oil. Freeze-drying from aqueous methanol afforded the title compound as a yellow amorphous solid (226 mg, 82%). δH (DMSO-d$^6$, 340K) 9,72 (1H, s), 9.28 (1H, br s), 8.53 (1H, d, J 5.6 Hz), 7.82 (2H, d, J 8.5 Hz), 7.51 (1H, d, J 5.6 Hz), 7.34 (1H, d, J 8.7 Hz), 7.21 (2H, d, J 8.5 Hz), 6.92 (1H, s), 5.11 (1H, m), 4.60–4.41 (4H, m), 3.23 (1H, dd, J 14.0,4.6 Hz), 3.04 (1H, dd, J 14.0, 10.1 Hz), 2.43 (3H, s), 1.12 (6H, t, J 7.1 Hz); m/z (ES$^+$, 70V) 474 (MH$^+$).

EXAMPLE 35

Ethyl (S)-3-[4-(3-methyl-2,7-naphthyridin-1-ylamino)phenyl]-2-[2-N,N-di-n-propylamino-3,4-dioxocyclobut-1-enylamino]propanoate Prepared in a similar manner to the compound of Example 33 from the compound of Example 30 and di-n-propylamine to give the title compound as a light yellow foam. δH (DMSO-d$^6$, 350K) 9.74 (1H, s), 9.27 (1H, s), 8.55 (1H, d, J 5.6 Hz), 7.85 (2H, d, J 8.5 Hz), 7.52 (1H, d, J 5.6 Hz), 7.31 (1H, d, J 8.7 Hz), 7.21 (2H, d, J 8.5 Hz), 6.94 (1H, s), 5.19 (1H, m), 4.19 (2H, q, J 7.1 Hz), 3.46 (4H, m), 3.25 (1H, dd, J 14.1, 5.1 Hz), 3.09 (1H, dd, J 14.1, 9.7 Hz), 2.45 (3H, s), 1.54 (4H, m), 1.23 (3H, t, J 7.1 Hz) and 0.86 (6H, t, J 7.1 Hz); m/z (ES$^+$, 70V) 530 (MH$^+$).

EXAMPLE 36

(S)-3-[4-(3-Methyl-2,7-naphthyridin-1-ylamino)phenyl]-2-[2-N,N-di-n-propylamino-3,4-dioxocyclobut-1-enylamino]-propanoic Acid Prepared in a similar manner to the compound of Example 34 from the compound of Example 35 to give the title compound as a yellow amorphous solid. δH (DMSO-d$^6$, 340K) 9.74 (1H, s), 9.32 (1H, br s), 8.54 (1H, d, J 5.7 Hz), 7.83 (2H, d, J 8.5 Hz), 7.52 (1H, d, J 5.7 Hz), 7.30 (1H, d, J 9.0 Hz), 7.21 (2H, d, J 8.5 Hz), 6.94 (1H, s), 5.13 (1H, m), 3.53–3.43 (2H, m), 3.42–3.31 (2H, m), 3.24 (1H, dd, J 14.1, 4.6 Hz), 3.04 (1H, dd, J 14.1, 10.1 Hz), 2.43 (3H, s), 1.57–1.46 (m) and 0.83 (6H, t, J 7.3 Hz); m/z (ES$^+$, 70V) 502 (MH$^+$).

EXAMPLE 37

Ethyl (S)-3-[4-(3-methyl-2,7-naphthyridin-1-ylamino)phenyl]-2-[2-(cis2,5-dimethylpyrrolidin-1-yl)-3,4-dioxocyclobut-1-enylamino]propanoate Prepared in a similar manner to the compound of Example 33, from the compound of Example 30 and cis 2,5-dimethylpyrrolidine. δH (DMSO-d$^6$), 9.75 (1H, s), 9.45 (1H, s), 8.56 (1H, d, J 5.6 Hz), 7.84 (2H, m), 7.65 (1H, d, J 9.1 Hz), 7.55 (1H, d, J 5.6 Hz), 7.23 (2H, d, J 8.5 Hz), 6.96 (1H, s), 5.13 (1H, m), 4.22–4.13 (4H, m), 3.22 (1H, dd, J 13.9, 4.6 Hz), 3.04 (1H, dd, J 13.8, 10.6 (Hz), 2.43 (3H, s), 2.12–2.05 (2H, m), 1.70–1.64 (2H, m), 1.24–1.15 (9H, m); m/z (ES$^+$, 70V) 528 (MH$^+$).

EXAMPLE 38

(S)-3-[4-(3-Methyl-2,7-naphthyridin-1-ylamino)phenyl]-2-[2-(cis2,5-dimethylpyrrolidin-1-yl)-3,4-dioxocyclobut-1-enylamino]propanoic Acid Prepared in a similar manner to the compound of Example 34 from the compound of Example 37 to give the title compound as a yellow amorphous solid. δH (DMSO-d$^6$, 340K) 9.72 (1H, s), 9.28 (1H, br s), 8.54 (1H, d, J 5.6 Hz), 7.82 (2H, d, J 8.5 Hz), 7.51 (1H, d, J 5.6 Hz), 7.22 (2H, d, J 8.5 Hz), 7.16 (1H, d, J 9.0 Hz), 6.92 (1H, s), 5.08 (1H, m), 4.19 (1H, m), 3.23 (1H, dd, J 14.1, 4.7 Hz), 3.07 (1H, dd, J 14.1, 9.7 Hz), 2.42 (3H, s), 2.15–2.03 (2H, m), 1.73–1.62 (2H, m), 1.25 (3H, d, J 6.4 Hz) and 1.22 (3H, d, J 6.4 Hz); m/z (ES$^+$, 70V) 500 (MH$^+$).

EXAMPLE 39

Ethyl (S)-3-[4-(3-methyl-2,7-naphthyridin-1-ylamino)phenyl]-2-[2-azepan-1-yl)-3,4-dioxocyclobut-1-enylamino]propanoate A solution of the compound of Example 29 (392 mg, 0.83 mmol) and azepane (164 mg, 1.66 mmol) in absolute ethanol (4 ml) was stirred at room temperature for 0.5 h. The volatiles were removed in vacuo and the obtained yellow foam chromatographed (silica; 1–2% EtOH/DCM) to afford the title compound as a yellow powder (362 mg, 83%). δH (DMSO-d$^6$, 350K) 9.76 (1H, s), 9.29 (1H, s), 8.58 (1H, d, J 5.6 Hz), 7.88 (2H, d, J 8.6 Hz), 7.55 (1H, d, J 5.6 Hz), 7.43 (1H, br s), 7.23 (2H, d, J 8.6 Hz), 6.97 (1H, s), 5.22 (1H, m), 4.21 (2H, q, J 7.1 Hz), 3.68 (4H, m), 3.26 (1H, dd, J 14.1, 5.1 Hz), 3.10 (1H, dd, J 14.1, 9.8 Hz), 2.47 (3H, s), 1.70–1.65 (1H, m), 1.57–1.51 (4H, m) and 1.25 (3H, t, J 7.1 Hz); m/z (ES$^+$, 70V) 528 (MH$^+$).

EXAMPLE 40

(S)-3-[4-(3-Methyl -2,7-naphthyridin-1-yl amino) phenyl]-2-[2-(azepan-1-yl-3,4-dioxocyclobut-1-enylamino]propanoic Acid The compound of Example 39 (350 mg, 0.66 mmol) was treated with a solution of LiOH.H$_2$O (41 mg, 0.98 mmol) in dioxan (3 ml) and water (4 ml) for 1 h. A few drops of AcOH were added and the volatiles removed in vacuo. The residue was treated with water and the yellow solid collected by filtration with water washing, and dried to give the title compound as a yellow powder (278 mg, 84%). δH (DMSO-d$^6$, 350K) 9.75 (1H, s), 9.29 (1H, br s), 8.57 (1H, d, J 5.6 Hz), 7.87 (2H, d, J 8.5 Hz), 7.54 (1H, d, J 5.6 Hz), 7.34 (1H, d, J 9.0 Hz), 7.24 (1H, d, J 8.5 Hz), 6.96 (1H, s), 5.16 (1H, m), 3.70–3.60 (4H, m), 3.27 (1H, dd, J 14.0, 4.7 Hz), 3.08 (1H, dd, J 14.0, 10.0 Hz), 2.47 (3H, s), 1.78–1.65 (4H, m) and 1.60–1.49 (4H, m); m/z (ES$^+$, 70V) 500 (MH$^+$).

EXAMPLE 41

Methyl (S)-3[4-(3-methyl-2,7-naphthyridin-1-yloxy) phenyl]-2-[2-isopropoxy-3,4-dioxocyclobut-1-enylamino]propanoate N,N-DIPEA (1.96 g, 2.4 ml, 15.2 mmol) was added to a stirred suspension of Intermediate 13 (2.0 g, 34.90 mmol) and 1,2-diisopropoxy-3,4-dioxocyclobut-1-ene (1.03 g, 5.20 mmol) in absolute ethanol (30 ml). The reaction mixture was stirred at room temperature for 18 h, then the volatiles were removed in vacuo. The residue was partitioned between EtOAc and water. The phases were separated and the aqueous layer re-extracted with EtOAc. The combined organic extracts were washed with brine, dried (Na$_2$SO$_4$) and evaporated in vacuo. The residue was chromatographed (silica: 50% EtOAc/Hexane -100% EtOAc) affording the title compound as a white foam (1.93 g, 83%). δH (CDCl$_3$) 9.73 (1H, s), 8.67 (1H, d, J 6.0 Hz), 7.63 (1H, d, 6.0 Hz), 7.28–7.20 (4H, m), 7.18 (1H, s), 6.49 and 5.94 (togher 1H, br s), 5.39 (1H, m), 5.22 and 4.69 (together 1H, br s), 3.83 (3H, s), 3.35–3.15 (2H, br m), 2.51 (3H, s), 1.45–1.41 (6H, overlapping d); m/z (ES$^+$, 70V) 476 (MH$^+$).

EXAMPLE 42

Ethyl (S)-3-[4-(3-methyl-2,7-naphthyridin-1-yloxy) phenyl]-2-[2 -ethoxy-3,4-dioxocyclobut-1-enylamino]-propanoate A solution of Intermediate 15 (10.9 g, 31.0 mmol) and 1,2-diethoxy-3,4-dioxocyclobut-1-ene (5.54 g, 32.6 mmol) in absolute ethanol (100 ml) was stirred at room temperature for 3.5 h. The resulting precipitate was isolated by filtration, washed with Et$_2$O, affording a very slighly yellow amorphous solid (10.6 g). Chromatography (silica; 75% EtOAc/Hexane—100% EtOAc) afforded the title compound as a white solid (8.44 g, 57%). δH (CDCl$_3$) 9.46 (1H, s), 9.12 and 8.94 (together 1H, d, J 8.1 Hz), 8.59 (1H, d, J 5.7 Hz), 7.62 (1H, d, J 5.7 Hz), 7.22 (1H, s), 7.21 (2H, d, J 8.6 Hz), 7.11 (2H, d, J 8.6 Hz), 4.78 and 4.39 (together 1H, m), 4.57–4.38 (2H, m), 4.11–3.98 (2H, m), 3.26 (1H, dd, J 14.0, 7.0 Hz), 3.14 (1H, dd, J 14.0, 10.0 Hz), 2.28 (3H, s), 1.26–1.15 (3H, m) and 1.15–1.01 (3H, m); m/z (ES$^+$, 70V) 476 (MH$^+$).

EXAMPLE 43

Methyl (S)-3-[4-(3-methyl-2,7-naphthyridin-1-yloxy)phenyl]-2-[2-N,N-diethylamino-3,4-dioxocyclobut-1-enylamino]propanoate A solution of the compound of Example 41 (350 mg, 0.74 mmol) and diethylamine (134 mg, 1.83 mmol) in methanol (10 ml) was stirred at room temperature for 3 days. The volatiles were removed in vacuo and the residue chromatographed (silica; 5% DCM: 95% EtOAc) to afford the title compound as a white foam (298 mg, 83%). δH (CDCl$_3$) 9.70 (1H, s), 8.69 (1H, d, J 5.9 Hz), 7.55 (1H, d, J 5.9 Hz), 7.24 (2H, d, J 8.6 Hz), 7.18 (2H, d, J 8.6 Hz), 7.14 (1H, s), 5.48 (1H, m), 3.83 (3H, s), 3.70–3.30 (4H, br s), 3.35 (1H, dd, J 14.2, 4.8 Hz), 3.30 (1H, dd, J 14.2, 5.7 Hz), 2.45 (3H, s) and 1.25 (6H, t, J 7.2 Hz); m/z (ES$^+$, 70V) 489 (MH$^+$).

EXAMPLE 44

(S)-3-[4-(3-Methyl-2,7-naphthyridin-1yloxy) phenyl]-2-[2-N,N-diethylamino-3,4-dioxocyclobut-1-enylamino]propanoic Acid The compound of Example 43 (285 mg, 0.58 mmol) was treated with a solution of LiOH.H$_2$O (36 mg, 0.86 mmol) in dioxan (5 ml) and water (7 ml) at room temperature for 1.5 h. A few drops of AcOH were added and the volatiles were removed in vacuo. The residue was chromatographed [silica; DCM (200), MeOH (20), AcOH (3), H$_2$O (2)] to afford an oil. Freeze-drying from aqueous methanol afforded the title compound as a very pale yellow amorphous solid (230 mg, 83%). δH (DMSO-d$^6$) 9.60 (1H, s), 8.73 (1H, d, J 5.7 Hz), 7.76 (1H, d, J 5.7 Hz), 7.75 (1H, masked d), 7.35 (2H, d, J 8.5 Hz), 7.34 (1H, s), 7.23 (2H, d, J 8.5 Hz), 5.16 (1H, m), 3.70–3.35 (4H, br m), 3.32 (1H, dd, J 13.0, 3.9 Hz), 3.07 (1H, dd, J 13.9, 11.3 Hz), 2.36 (3H, s) and 1.11 (6H, t, J 7.0 Hz); m/z (ES$^+$, 70V) 475 (MH$^+$).

EXAMPLE 45

Methyl (S)-3-[4-(3-methyl-2,7-naphthyridin-1-yloxy)phenyl]-2-[2-N,N di-n-propylamino-3,4-dioxocyclobut-1-enylamino]propanoate Prepared in a similar manner to the compound of Example 43 from the compound of Example 41 and di-n-propylamine to give the title compound as a very pale yellow foam. δH (CDCl₃) 9.69 (1H, s), 8.69 (1H, d, J 5.8 Hz), 7.53 (1H, d, J 5.8 Hz), 7.23 (2H, d, J 8.6 Hz), 7.17 (2H, d, J 8.6 Hz), 5.48–5.42 (1H, m), 5.39–5.36 (1H, m), 3.84 (3H, s), 3.80–3.40 (2H, br s), 3.38–3.29 (2H, m), 3.40–3.00 (2H, br s), 2.45 (3H, s), 1.69–1.58 (4H, m) and 0.90 (6H, t, J 7.3 Hz); m/z (ES⁺, 70V) 517 (MH⁺).

EXAMPLE 46

(S)-3-[4-(3-Methyl-2,7-naphthyridin-1-yloxy) phenyl]-2-[2-N,N-di-n-propylamino-3,4-dioxocyclobut-1-enylamino]propanoic Acid Prepared in a similar manner to the compound of Example 44 from the compound of Example 45 to give the title compound as a very pale yellow amorphous solid. δH (DMSO-d⁶, 350K) 9.58 (1H, s), 8.71 (1H, d, J 5.7 Hz), 7.71 (1H, d, J 5.7 Hz), 7.34 (2H, d, J 8.6 Hz), 7.33 (1H, s), 7.30 (1H, d, J 9.0 Hz), 7.23 (2H, d, J 8.6 Hz), 5.17 (1H, m), 3.54–3.47 (2H, m), 3.45–3.37 (2H, m), 3.32 (1H, dd, J 14.1, 4.7 Hz), 3.13 (1H, dd, J 14.1, 11.0 Hz), 2.40 (3H, s), 1.59–1.49 (4H, m) and 0.85 (6H, t, J 7.4 Hz); m/z (ES⁺, 70V) 503 (MH⁺).

EXAMPLE 47

Methyl (S)-3-[4-(3-methyl-2,7-naphthyridin-1-yloxy)phenyl]-2-[2-(cis-2,5-dimethylpyrrolidin-1yl)-3,4-dioxocyclobut-1-enylamino]propanoate Prepared in a similar manner to the compound of Example 43 from the compound of Example 41 and cis-2,5-dimethylpyrrolidine to give the title compound as a white foam. δH (CDCl₃) 9.72 (1H, s), 8.68 (1H, d, J 5.8 Hz), 7.58 (1H, d, J 5.8 hz), 7.23 (2H, d, J 8.6 Hz), 7.19 (2H, d, J 8.6 Hz), 7.16 (1H, s), 5.47–5.43 (1H, m), 5.40–5.38 (1H, m), 4.30–4.10 (2H, br s), 3.83 (3H, s), 3.38–3.28 (2H, m), 2.47 (3H, s), 2.18–2.10 (2H, m), 1.77–1.71 (2H, m), 1.39 (3H, d, J 6.5 Hz) and 1.33 (H, d, J 6.5 Hz); m/z (ES⁺, 70V) 515 (MH⁺).

EXAMPLE 48

(S)-3-[4-(3-Methyl-2,7-naphthyridin-1-yloxy) phenyl]-2-[2-(cis-2,5-dimethylpyrrolidin-1-yl)-3,4-dioxocyclobut-1-enylamino]propanoic Acid Prepared in a similar manner to the compound of Example 44 from the compound of Example 47 to give the title compound as a pale yellow amorphous solid. δH (DMSO-d⁶, 350K) 9.59 (1H, s), 8.71 (1H, d, J 5.7 Hz), 7.72 (1H, d, J 5.7 Hz), 7.36 (2H, d, J 8.6 Hz), 7.34 (1H, s), 7.25 (2H, d, J 8.6 Hz), 7.17 (1H, d, J 8.8 Hz), 5.16 (1H, m), 4.24–4.19 (2H, m), 3.33 (1H, dd, J 14.1, 4.8 Hz), 3.16 (1H, dd, J 14.1, 9.8 Hz), 2.40 (3H, s), 2.17–2.05 (2H, m), 1.76–1.65 (2H, m), 1.29 (3H, d, J 6.4 Hz) and 1.24 (3H, d, J 6.4 Hz); m/z (ES⁺, 70V) 501 (MH⁺).

EXAMPLE 49

Ethyl (S)-3-[4-(3-methyl-2,7-naphthyridin-1-yloxy) phenyl]-2-[2-(azepan-1-yl)-3,4-dioxocyclobut-1-enylamino]propanoate Prepared in a similar manner to the compound of Example 43 from the compound of Example 42 and azepane to give the title compound as a white powder. δH (DMSO-d⁶, 350K) 9.61 (1H, s), 8.73 (1H, d, J 5.7 Hz), 7.74 (1H, d, J 5.7 Hz), 7.48 (1H, d, J 8.0 Hz), 7.36 (2H, d, J 8.5 Hz), 7.35 (1H, s), 7.26 (2H, d, J 8.5 Hz), 5.25 (1H, m), 4.21 (2H, q, J 7.1 Hz), 3.71–3.67 (4H, m), 3.33 (1H, dd, J 14.1, 5.3 Hz), 3.17 (1H, dd, J 14.1, 9.8 Hz), 2.42 (3H, s), 1.74–1.66 (4H, m), 1.58–1.51 (4H, m) and 1.25 (3H, t, J 7.1 Hz); m/z (ES⁺, 70V) 529 (MH⁺).

EXAMPLE 50a

Methyl (S)-3-[4-(3-methyl-2,7-naphthyridin-1-yloxy)phenyl]-2-[2-(azepan-1-yl)3,4-dioxocyclobut-1-enylamino]propanoate Prepared in a similar manner to the compound of Example 43 from the compound of Example 41 and azepane to give the title compound as a white foam. δH (DMSO-d⁶), 9.59 (1H, s), 8.73 (1H. d, J 5.7 Hz), 7.87 (1H, m), 7.77 (1H, d, J 5.7 Hz), 7.30 (1H, m), 7.30 (2H, d, J 8.6Hz), 7.24 (2H, d, J 8.5 Hz), 5.21 (1H, m), 3.72 (3H, s), 3.80–3.45 (4H, m), 3.39–3.30 (1H, m), 3.15–3.05 (1H, m), 2.50 (3H, s) and 1.70–1.44 (8H, m). m/z (ES⁺, 70V) 515 (MH⁺).

EXAMPLE 50b

Isopropyl (S)-3-[4-(3-methyl-2,7-naphthyridin-1-yloxy)phenyl]-2-[2-(azepan-1-yl)-3,4-dioxocyclobut-1-enylamino]propanoate The compound of Example 51 (641 mg, 1.28 mmol) was dissolved with heating in isopropyl alcohol (80 ml). To the solution at ambient temperature was added HOBt (199 mg, 1.47 mmol), and once dissolved EDC (282 mg, 1.47 mmol) was added. After 10min the now cloudy solution was heated briefly to give a clear solution which was stirred at ambient temperature for 5 h. The solvent was removed, the residue taken up into DCM, washed (NaHCO₃ solution), dried (MgSO₄), concentrated in vacuo and the resulting residue purified by chromatography (SiO₂; EtOAc) to give the title compound as a white solid (592 mg 85%). δH (DMSO) 9.60 (1H, s), 8.73 (1H, d, J 5.8 Hz), 7.77 (2H, m), 7.35 (3H, m), 7.25 (2H, d, J 6.7 Hz), 5.17 (1H, m), 4.97 (1H, sept, J 6.2 Hz), 3.65 (4H, br), 3.27 (1H, dd), 3.12 (1H, dd, J 13.8, 10.5 Hz), 2.37 (3H, s), 1.64 (4H, br s), 1.49 (4H, br s), 1.23 (3H, d, J 6.3 Hz), 1.21 (3H, d, J 6.3 Hz); m/z (ES⁺, 70V) 543 (MH⁺).

EXAMPLE 50c

Benzyl(S)-3-[4-(3-methyl -2,7-naphthyridin-1-yloxy)phenyl]-2-[2-(azepan-1-yl)-3,4-dioxocyclobut-1-enylamino]propanoate Prepared in a similar manner to the compound of Example 50b from benzylalcohol. δH (DMSO) 9.71 (1H, s), 8.83 (1H, d, J 5.7 Hz), 7.85 (1H, d, J 5.8 Hz), 7.59 (1H, d), 7.50–7.40 (8H, m), 7.36 (2H, d, J 6.6 Hz), 5.45 (1H, m), 5.34 (2H, s), 3.78 (4H, t, J 6.0 Hz), 3.47 (1H, dd, J 14.1, 5.2 Hz), 3.30 (1H, dd, J 14.1, 9.9 Hz), 2.52 (3H, s), 1.77 (4H, br), 1.63 (4H, br). m/z (ES⁺, 70V) 590 (MH⁺).

EXAMPLE 50d n-Pentyl (S)-3-[4-(3-methyl-2,7-naphthyridin-1-yloxy)phenyl]-2-[2-(azepan-1-yl)-3,4-dioxocyclobut-1-enylamino]propanoate Prepared in a similar manner to the compound of Example 50b from n-pentylalcohol. δH (CDCl₃, 400 MHz) 9.67 (1H, s), 8.69(1H, d, J 5.8 Hz), 7.55 (1H, dd, J 5.8, 0.8 Hz), 7.22 (4H, m), 7.13 (1H, s), 5.67 (1H, d, J 8.6 Hz), 5.47 (1H, m), 4.17 (2H, q, J 6.8 Hz), 3.88 (2H, br), 3.46 (2H, br), 3.32 (2H, d, J 6.0 Hz), 2.46 (3H, s), 1.76 (4H, br), 1.68 (2H, t, J 7.0 Hz), 1.61 (4H, br), 1.34 (4H, m), 0.92 (3H, t, J 6.1 Hz).

EXAMPLE 50e n-Butyl (S)-3-[4-(3-methyl-2,7-naphthyridin-1-yloxy)phenyl]-2-[2-(azepan-1-yl)-3,4-dioxocyclobut-1-enylamino]propanoate Prepared in a similar manner to the compound of Example 50b from n-butanol. δH (d$^6$ DMSO) 9.61 (1H, s), 8.71 (1H, d, J 8.2 Hz), 7.74 (1H, d, J 8.2 Hz), 7.41 (3H, m), 7.29 (2H, d, J 8.54 Hz), 5.26 (1H, m), 4.16 (2H, m), 3.69 (4H, m), 3.35 (1H, dd, J 12.0, 5.9 Hz), 3.18 (1H, dd, J 11.1, 5.8 Hz), 2.43 (3H, s), 1.71 (4H, br), 1.66 (2H, m), 1.57 (4H, m), 1.37 (2H, m), 0.94 (3H, t); m/z (ES$^+$, 70V) 557 (MH$^+$).

EXAMPLE 50f

Cyclopentyl (S)-3-[4-(3-methyl-2,7-naphthyridin-1-yloxy)phenyl]-2-[2-(azepan-1-yl)-3,4-dioxocyclobut-1-enylamino]propanoate Prepared in a similar manner to the compound of Example 50b from cyclopentanol. δH (d$^6$ DMSO) 9.60 (1H, s), 8.72 (1H, d, J 8.1 Hz), 7.74 (1H, d, J 8.1 Hz), 7.35 (3H, m), 7.26 (2H, d, J 8.5 Hz), 5.20 (1H, m), 3.69 (4H, m), 3.28 (1H, dd, J 12.0, 5.8HZ), 3.14 (1H, dd, J 11.0, 5.7 Hz), 2.42 (3H, s), 1.87 (2H, m), 1.70–1.57 (17H, br m); m/z (ES$^+$, 70V) 569 (MH$^+$).

EXAMPLE 50g

N,N-Dimethylaminoethyl (S)-3-[4-(3-methyl-2,7-naphthyridin-1-yloxy)phenyl]-2-[2-(azepan-1-yl)-3,4-dioxocyclobut-1-enylamino]propanoate To a solution of the compound of Example 51 (700 mg, 1.40 mmol) and N,N-dimethylethanolamine (374 mg, 4.20 mmol) in DCM (5 ml) was added PyBOP (873 mg, 1.68 mmol). The solution was left at room temperature overnight and the solvent removed under high vacuum. The rsidue was taken up in DCM (50 ml), washed with saturated NaHCO$_3$ (3×50 ml), extracted into 0.1M HCl (3×50 ml) and the aqueous soution rebasified (NaHCO$_3$). The product was then extracted into DCM (3×50 ml), dried (MgSO$_4$) and concentrated in vacuo to give the title compound as an off white solid (452 mg). δH (DMSO) 9.70 (1H, s), 8.81 (1H, d, J 5.7 Hz), 7.82 (1H, d, J 5.8 Hz), 7.50–7.40 (4H, m), 7.37 (2H, d, J 8.6 Hz), 5.36 (1H, m), 4.33 (2H, m), 3.78 (4H, m), 3.43 (1H, dd, J 14.2, 5.2 Hz), 3.28 (1H, dd, J 14.2, 9.7 Hz), 2.66 (2H, m), 2.52 (3H, s), 2.33 (6H, s), 1.79 (4H, br m), 1.65 (4H, br m); m/z (ES$^+$, 70V) 572 (MH$^+$).

EXAMPLE 50h

Morpholino-N-ethyl (S)-3-[4-(3-methyl-2,7-naphthyridin-1-yloxy)-phenyl]-2-[2-(azepan-1-yl)-3,4-dioxocyclobut-1-enylamino]propanoate Prepared in a similar manner to the compound of Example 50 g from 4-(2-hydroxyethyl)morpholine. δH (DMSO) 9.61 (1H, s), 8.73 (1H, d, J 5.7HZ), 7.74 (1H, d, J 5.7 Hz), 7.44 (1H, d, J 9.3 Hz), 7.36 (3H, m), 7.28 (2H, d, J 8.6 Hz), 5.27 (1H, m), 4.27 (2H, m), 3.69 (4H, t, l 6.0 Hz), 3.58 (4H, m), 3.34 (1H, dd, J 14.2, 5.2 Hz), 3.18 (1H, dd, J 14.2, 9.7 Hz), 2.62 (2H, t, J 5.7 Hz), 2.45 (7H, m), 1.69 (4H, m), 1.56 (4H, br m); m/z (ES$^+$, 70V), 614 (MH$^+$).

EXAMPLE 51

(S)-3-[4-(3-Methyl-2,7-naphthyridin-1-yloxy)phenyl]-2-[2-(azepan-1-yl)-3,4-dioxocyclobut-1-enylamino]propanoic Acid Prepared in a similar manner to the compound of Example 44 from the compound of Example 50a to give the title compound as a pale yellow powder. δH (DMSO-d$^6$, 350K) 9.58 (1H, s), 8.70 (1H, d, J 5.7 Hz), 7.71 (1H, d, J 5.7 Hz), 7.34 (2H, d, J 8.6 Hz), 7.33 (1H, masked s), 7.26 (1H, masked s), 7.25 (2H, d, J 8.6 Hz), 5.17 (1H, m), 3.70–3.60 (4H, m), 3.32 (1H, dd, J 14.1, 4.8 Hz), 3.14 (1H, dd, J 14.1, 9.9 Hz), 2.41 (3H, s), 1.74–1.60 (4H, m) and 1.57–1.49 (4H, m); m/z (ES$^+$, 70V) 501 (MH$^+$).

EXAMPLE 52

Methyl-(S)-3-[4-(3-methyl-2,7-naphthyridin-1-yloxy)phenyl]-2-[(2-(trans-2,5-dimethylpyrrolidin-1-yl)-3,4-dioxocyclobut-1-enyl)amino]propanoate Prepared in a similar manner to the compound of Example 43 from the compound of Example 41 and trans 2,5-dimethylpyrrolidine to give the title compound. δH (DMSO-d$^6$) 9.45 (1H, s), 8.59 (1H, d, J 5.7 Hz), 7.62 (2H, m), 7.20 (3H, m), 7.10 (2H, m), 5.10 (1H, m), 4.18 (2H, m), 3.57 (3H, s), 3.15–2.85 (2H, m), 2.23 (3H, s), 2.05 (2H, m), 1.45 (2H, m), 0.75 (6H, m). m/z (ES$^+$, 70V) 514 (MH$^+$).

EXAMPLE 53

(S)-3-[4-(3-Methyl-2,7-naphthyridin-1-yloxy)phenyl-2-[2-(trans-dimethylpyrrolidin-1-yl)-3,4-dioxocyclobut-1-enylamino]propionic Acid Prepared in a similar fashion to the compound of Example 44 from the compound of Example 52 to give the title compound as a white solid. δH (DMSO-d$^6$, 350K), 9.58 (1H, s), (8.70 (1H, d, J 5.7 Hz), 7.71 (1H, d, J 5.7 Hz), 7.37–7.21 (6H, m), 5.14 (1H, m), 4.37 (2H, d, J 6.74Hz), 0.4×3.35 (1H, dd, J 14.1, 4.5 Hz), 0.6×3.32 (1H, dd, J 14.2, 5.1 Hz), 0.6×3.20 (1H, dd, J 14.1, 9.7 Hz), 0.4×3.11 (1H, dd, J 14.1, 9.5 Hz), 2.38 (3H, s), 2.17 (2H, m), 1.62 (2H, m), 1.11 (3H, 0.6, d, J 6.47 Hz), 1.04 (3H, ×0.4, d, J 6.4 Hz). m/z (ES$^+$, 70V) 501 (MH$^+$).

EXAMPLE 54

Methyl (S)-3-[4-(3-methyl-2,7-naphthyridin-1-yloxy)phenyl]-2-[2-(2-methyl piperidin-1-yl)-3,4-dioxocyclobut-1-enylamino]propanoate Prepared in a similar manner to the compound of Example 43 from the compound of Example 41 and 2-methylpiperidine to give the title compound as an off white foam. δH (DMSO-d$^6$), 9.75 (1H, s), 8.88 (1H, d, J 5.7 Hz), 8.18–8.07 (1H, m), 7.92 (1H, d, J 5.75 Hz), 7.5–7.32 (5H, m), 5.38 (1H, m), 4.6 (1H, m), 4.18 (1H, m), 3.88 (3H, s), 3.56–3.14 (3H, m), 2.64 (3H, s), 1.95–1.50 (6H, m) and 1.30–1.24 (3H, m). m/z (ES$^+$, 70V) 515 (MH$^+$).

EXAMPLE 55

(S)-3-[4-(3-Methyl-2,7-naphthyridin-1-yloxy)phenyl]-2-[2-(2-methylpiperidin-1-yl)-3,4-dioxocyclobut-1-enylamino]propionic Acid Prepared in a similar manner to the compound of Example 44 from the compound of Example 54 to give the title compound as a white solid. δH (DMSO-d$^6$, 350K), 9.59 (1H, s), 8.70 (1H, d, J 5.7 Hz), 7.71 (1H, d, J 5.7 Hz), 7.46 (1H, m), 7.35–7.33 (3H, m), 7.26–7.23 (2H, m), 5.16 (1H, m), 4.47 (1H, m), 4.04 (1H, m), 3.20 (1H, dd, J 14.2, 4.6 Hz), 3.10 (1H, dd, J 14.1, 9.8 Hz), 2.39 (3H, s), 1.80–1.40 (6H, m), 1.24 and 1.21 (together 3H, d, J 6.8 Hz); m/z (ES$^+$, 70V) 501 (MH$^+$).

EXAMPLE 56

Methyl-3-[4-(3-methyl-2,7-naphthyridin-1-yloxy)phenyl]-2-[2-(N,N-diisobutylamino)-3,4-dioxocyclobut-1-enylamino]propanoate Prepared in a similar manner to the compound of Example 43 from the compound of Example 41 and diisobutylamine to give the title compound as a white foam. δH (DMSO-d⁶), 9.58 (1H, s), 8.73 (1H, d, J 5.7 Hz), 7.76 (2H, d, J 5.8 Hz), 7.39–7.30 (3H, m), 7.20 (2H, d, J 8.5 Hz), 5.3 (1H, m), 3.72 (3H, s), 3.40–3.00 (4H, m), 2.35 (3H, s); 1.88–1.70 (12H, m). m/z (ES⁺, 70V) 545 (MH⁺).

EXAMPLE 57

(S)-3-[4-(3-Methyl-2,7-naphthyridin-1-1yloxy) phenyl]-2-[2(N,N-diisobutylamino)-3,4-dioxocyclobut-1-enylamino]propionic Acid Prepared in a similar manner to the compound of Example 44 from the compound of Example 56 to give the title compound as a white solid. δH (DMSO-d⁶, 350K), 9.58 (1H, s), 8.70 (1H, s), 7.72 (1H, d, J 5.7 Hz), 7.33 (1H, m), 7.35–7.26 (3H, m), 7.22 (2H, d, J 8.6 Hz), 5.18 (1H, m), 3.41–3.08 (4H, m), 2.40 (3H, s), 1.91–1.80 (4H, m), 0.85 (6H, d, J 6.6 Hz) and 0.83 (6H, d, J 6.6 Hz); m/z (ES⁺, 70V) 531 (MH⁺).

EXAMPLE 58

Ethyl (S)-3-[4-(3-ethyl -2,7-naphthyridin-1-ylamino)phenyl]-2-(2-azepan-1-yl)3,4-dioxocyclobut-1-enylamino]propanoate Prepared in a similar manner to the compound of Example 3 to give the title compound as a yellow foam. δH (DMSO-d⁶), 9.74 (1H, s), 9.45 (1H, s), 8.55 (1H, d, J 5.6 Hz), 7.86 (2H, d, J 8.5 Hz), 7.79 (1H, d, J 9.0 Hz), 7.57 (1H, d, J 5.6 Hz), 7.19 (2H, d, J 8.3 Hz), 6.95 (1H, s), 5.14 (1H, nr, m), 4.15 (2H, q, J 6.8 Hz), 3.66–3.44 (4H, m), 3.22 (1H, dd, J 13.5, 9.0 Hz), 3.00 (1H, dd, J 13.8, 10.8 Hz), 2.70 (2H, q, J 7.5 Hz), 1.59–1.44 (8H, m), 1.28–1.12 (6H, m). m/z (ES⁺, 70V) 542 (MH⁺).

EXAMPLE 59

(S)-3-[4-(3-Ethyl-2,7-naphthyridin-1-ylamino) phenyl]-2-[2-(azepan-1-yl])-3,4-dioxocyclobut-1-enylamino]propionic Acid Prepared in a similar manner to the compound of Example 4 from the compound of Example 58 to give the title compound as a yellow solid. δH (DMSO-d⁶, 360K), 9.64 (1H, s), 9.13 (1H, s), 8.46 (1H, d, J 5.6 Hz); 7.76 (2H, d, J 8.5 Hz), 7.45 (1H, d, J 5.6 Hz), 7.11 (3H, m), 6.84 (1H, s), 5.0 (1H, m), 3.55 (4H, m), 3.15 (1H, dd, J 14.1, 4.8 Hz), 2.98 (1H, dd, J 14.1, 9.3 Hz), 2.65 (2H, q, J 7.5 Hz), 1.64–1.37 (8H, m) and 1.20 (3H, t, J 7.5 Hz). m/z (ES⁺, 70V) 514 (MH⁺).

EXAMPLE 60

(S)-3-[4-(3-Ethyl-2,7-naphthyridin-1-ylamino) phenyl]-2-[(2-(,cis-2,5-dimethylpyrrolidin-1-yl)-3,4-dioxocyclobut-1-enyl)amino]propanoic Acid Prepared in a similar manner to the compound of Example 4 to give the title compound as a yellow solid. δH (DMSO-d⁶, 350K) 9.76 (1H, s), 9.29 (1H, s), 8.58 (1H, d, J 5.6 Hz), 7.87 (2H, d, J 6.3 Hz), 7.57 (1H, d, J 5.6 Hz), 7.24 (2H, d, J 8.6 Hz), 7.11 (1H, m), 6.96 (1H, s), 5.09 (1H, m), 4.22 (2H, m), 3.26 (1H, dd, J 14.1, 4.7 Hz), 3.12 (1H, dd, J 14.1, 9.3 Hz), 2.76 (2H, q, J 7.5 Hz), 2.12 (2H, m), 1.7 (2H, m) and 1.25 (6H, m); m/z (ES⁺, 70V) 514 (MH⁺).

The following compounds were prepared in a similar manner to the compound of Example 40.

EXAMPLE 61

(S)-3-[4-(3-Ethyl-2,7-naphthyridin-1-ylamino) phenyl]-2-[2-N,N-diethylamino-3,4-dioxocyclobut-1-enylamino]propanoic Acid δH (DMSO-d⁶) 9.82 (1H, s), 9.51 (1H, s), 8.63 (1H, d, J 5.6Hz), 7.91 (2H, d, J 8.5 Hz), 7.74 (1H, d, J 9.1 Hz), 7.65 (1H, d, J 5.6 Hz), 7.28 (2H, d, J 8.5 Hz), 7.02 (1H, s), 5.14 (1H, m), 3.68–3.50 (4H, m), 3.28 (1H, dd, J 14.0, 4.1 Hz), 3.06 (1H, dd, J 13.8, 11.9 Hz), 2.77 (2H, q, J 7.5 Hz), 1.33 (3H, t, J 7.5 Hz) and 1.66 (6H, t, J 7.1 Hz); m/z (ES⁺, 70V) 488 (MH⁺).

EXAMPLE 62

(S)-3-[4-(3-Ethyl-2,7-naphthyridin-1-yloxy)phenyl]-2-[2-N,N-diethylamino-3,4-dioxocyclobut-1-enylamino]-propanoic Acid δH (DMSO-d⁶, 360K) 9.59 (1H, s), 8.70 (1H, d, J 5.7 Hz), 7.74 (1H, d, J 5.7 Hz), 7.38–7.23 (5H, m), 5.20(1H, m), 3.60–3.50 (4H, m), 3.32 (1H, dd, J 14.2, 4.7 Hz), 3.15 (1H, dd, J 14.1, 10.0 Hz), 2.68 (2H, q, J 7.5 Hz), 1.19–1.13 (9H, m); m/z (ES⁺, 70V) 489 (MH⁺).

EXAMPLE 63

(S)-3-[4-(3-Ethyl-2,7-naphthrydin-1-yloxy)phenyl]-2-[2-(azepan-1-yl)-3,4-dioxocyclobut-1-enylamino] propanoic Acid δH (DMSO-d⁶, 360K) 9.59 (1H, s), 8.70 (1H, d, J 5.7 Hz), 7.74 (1H, d, J 5.8 Hz), 7.38–7.25 (5H, m), 5.20 (1H, m), 3.68 (4H, m), 3.32 (1H, dd, J 14.2, 4.8 Hz), 3.14 (1H, dd, J 14.2, 9.9 Hz), 2.69 (2H, q, J 7.5 Hz), 1.72–1.50 (8H, m) and 1.18 (3H, t, J 7.5 Hz); m/z (ES⁺, 70V), 515 (MH⁺).

EXAMPLE 64

(S)-3-[4-(3-Ethyl-2,7-naphthyridin-1yloxy)phenyl]-2-[2-(cis-2,5-dimethylpyrrolidin-1-yl)-3,4-dioxocyclobut-1-enylamino]propanoic Acid δH (CDCl₃) (DMSO-d⁶, 360K) 9.59 (1H, s), 8.70 (1H, d, J 5.7 Hz). 7.74 (1H, d, J 5.7 Hz), 7.38–7.21 (5H, m), 7.05 (1H, m), 5.12 (1H, m), 4.2 (2H, m), 3.33 (1H, dd, J 14.2, 4.8 Hz), 3.17 (1H, dd, J 14.2, 9.6 Hz), 2.69 (2H, q, J 7.5 Hz), 2.15 (2H, m), 1.7 (2H, m), 1.3–1.13 (9H, m); m/z (ES⁺, 70V) 515 (MH⁺).

EXAMPLE 65

Methyl-(S)-3-{(4-(3-methoxycarbonyl)-2,7-naphthyridin-1-ylamino) phenyl}-2-[(2-isopropoxy-3,4-dioxocyclobut-1-enyl)amino]propanoate Prepared in a similar manner to the compound of Example 1 from the intermediate 5 to give the title compound. δH (CD₃OD) 9.7 (1H, s), 8.57 (1H, d, J 5.6 Hz), 8.57 (2H, br), 7.79 (1H, s), 7.73 (1H, d), 7.15 (2H, d), 5.20 (1H, m), 5.05 and 4.62 (1H, 2 x br), 3.92 (3H, s), 3.79 ((3H, s), 3.27 (1H, dd), 2.96 (1H, dd), 1.36 (6H, d, J 6.2 Hz); m/z (ES⁺, 70V) 519 (MH⁺).

EXAMPLE 66

Methyl-(S)-3-{(4-(3-methoxycarbonyl)-2,7-naphthyridin-1-ylamino) phenyl}-3-[(2-N,N-diethylamino-3,4-dioxocyclobut-1-enyl)amino] propanoate Prepared in a similar manner to the compound of Example 3 from the compound of Example 65 and diethylamine to give the title compound. δH (CD₃OD) 9.66 (1H, s), 8.61 (1H, d, J 5.7 Hz), 7.94 (1H, d, J 8.6 Hz), 7.78 (1H, s), 7.72 (1H, d, J 5.7 Hz), 7.21 (2H, d, J 8.6 Hz), 5.35 (1H, m), 3.93 (3H, s), 3.80 (3H, s), 3.56 (4H, br), 3.32 (1H, dd), 3.04 (1H, dd), 1.18 (6H, t, J 7.1 Hz); m/z (ES⁺, 70V) 532 (MH⁺).

EXAMPLE 67

(S)-3-{(4-(3-Methoxycarbonyl)-2,7-naphthyridin-1-ylamino)phenyl}-2-[(2-N,N-diethylamino-3,4-dioxocyclobut-1-enyl)amino]propanoic Acid Prepared in a similar manner to the compound of Example 4 from the compound of Example 66 to give the title compound. δH (CD$_3$OD) 9.78 (1H, s), 8.69 (1H, d, J 5.7 Hz), 7.99 (2H, d, J 8.5 Hz), 7.90 (1 H, s), 7.84 (1H, d, J 5.7 Hz), 7.2 (2H, d, J 8.5 Hz), 5.30 (1H, m), 3.99 (3H, s), 3.60 (4H, br), 3.42 (1H, dd, J 14.2, 4.3 Hz), 3.11 (1H, dd, J 14.2, 10.0 Hz), 1.21 (6H, t, J 7.2 Hz); m/z (ES$^+$, 70V) 518 (MH$^+$).

EXAMPLE 68

Ethyl-(S)-3-{(4-[(trifluoromethyl)-2,7-naphthyridin-1-yl]oxy)phenyl}-2-[2-ethoxy-3,4-dioxocyclobut-1-enylamino]propanoate HCl gas was bubbled through a solution of Intermediate 18 (298 mg, 0.57 mmol) in EtOAc (5 ml) for 10 min. The solvent was removed in vacuo, the residue taken up in EtOH (7 ml) and to the suspension was added DIPEA (2.11 mg, 1.71 mmol) followed by 1,2-diethoxy-3,4-dioxocyclobut-1-ene (102 mg, 0.60 mmol). After 2.5 h the solvent was removed and the residue purified by chromatography (SiO$_2$; 60% EtOAc/Hexane to give the title compound (272 mg, 90%) as an off-white glass. δH (CD$_3$OD) 9.66 (1H, s), 9.74 (1H, d, J 5.8 Hz), 7.87 (1H, d, J 5.7 Hz), 7.82 (1H, s), 7.23 (2H, d, J 8.7 Hz), 7.17 (2H, m), 4.94, 4.57 (1H, 2 x m), 4.55 (2H, m), 4.10 (2H, q, J 6.7 Hz), 3.20 (1H, m), 2.96 (1H, m), 1.28 (3H, m), 1.15 (3H, t, J 7.5 Hz); m/z (ES$^+$, 70V) 530 (MH$^+$).

EXAMPLE 69

Ethyl-(S)-3-{1(4-[(3-trifluoromethyl)-2,7-naphthyridin-1-yloxy)phenyl}-2-[2-N,N-diethylamino-3,4-dioxocyclobut-1-enylamino]propanoate To the compound of Example 68 (135 mg, 0.26 mmol) in EtOH (2.5 ml) and DCM (1.5 ml) was added diethylamine (56 mg, 0.77 mmol). After 2 days the solvent was removed and the residue purified by chromatography (SiO$_2$: EtOAc) to give the title compound (142 mg, 100%) as a colorless glass. δH (CD$_3$OD) 9.82 (1H, s), 8.89 (1H, d, J 5.8 Hz), 8.03 (1H, d, J 5.8 Hz), 7.98 (1H, s), 7.42 (2H, d, J 6.7 Hz), 7.32 (2H, d, J 6.7 Hz), 3.48 (1H, dd), 3.20 (1H, dd), 1.32 (4H, t, J 7.1 Hz), 1.23 (6H, t, J 7.2 Hz). m/z (ES$^+$, 70V) 583 (MH$^+$).

EXAMPLE 70

(S-3-{(4-[(3-Trifluoromethyl)-2,7-naphthyridin-1-yloxy)phenyl]-2-[2-N,N-diethylamino-3,4-dioxocyclobut-1-enylamino]proanoic Acid A solution of the compound of Example 69 (128 mg. 0.22 mmol) in 1:1 THF:H$_2$O (4 ml) was treated with LiOH.H$_2$O (14 mg, 0.330 mmol). After 2 h solvent removed in vacuo and the residue purified by chromatography (SiO$_2$; DCM:MeOH:AcOH:H$_2$O 200:20:3:2) to give the title compound (95 mg, 70%) as an off white solid. δH (DMSO-d$^6$, 350K) 9.82 (1H, t, J 0.7 Hz), 8.98 (1H, d, J 5.7 Hz), 8.13 (1H, s), 8.09 (1H, d, J 5.8 Hz), 7.41 (2H, d, J 8.7 Hz), 7.34 (2H, d, J 8.7 Hz), 5.17 (1H, m), 3.54 (4H, m), 3.35 (1H, dd, J 14.2, 4.4 Hz), 3.18 (1H, dd, J 14.1, 9.8 Hz), 1.16 (6H, t, J 7.1 Hz). m/z (ES$^+$, 70V) 529 (MH$^+$).

EXAMPLE 71

Ethyl-(S)-3-{(4-[(3-trifluoromethyl)-2,7-naphthyridin-1-yl]oxy)phenyl}-2-[2-(azepan-1-yl -3,4-dioxocyclobut-1-enylamino]propanoate To the compound of Example 68 (135 mg, 0.26 mmol) in EtOH) (2.5 ml) and DCM (1 ml) was added azepane (25 mg, 0.26 mmol). After 2 h the solvent was removed and the residue purified by chromatography (SiO$_2$: EtOAc) to give the title compound (128 mg, 86%) as a colorless glass. δH (CD$_3$OD) 9.91 (1H, s), 8.99 (1H, d, J 5.8 Hz), 8.12 (1H, d, J 5.8 Hz), 8.08 (1H, s), 7.50 (2H, d, J 8.7 Hz), 7.41 (2H, d, J 8.7 Hz), 5.45 (1H, m), 4.36 (2H, q, J 7.1 Hz), 3.98 (2H, br), 3.72 (2H, br), 3.57 (1H, dd, J 14.0, 5.0 Hz), 3.28 (1H, dd, J 14.0, 10.4 Hz), 1.85 (4H, br), 1.71 (4H, br), 1.41 (3H, t, J 7.1 Hz); m/z (ES$^+$, 70V), 583 (MH$^+$).

EXAMPLE 72

(S)-3-[(4-(3-Trifluoromethyl)-2,7-naphthyridin-1-yloxy)phenyl]-2-[2-azepan-1-yl)-3,4-dioxocyclobut-1-enylamino]proanoic Acid Prepared from the compound of Example 71 in a similar manner to Example 70 to give the title compound (50 mg, 66%) as an off-white solid. δH (DMSO-d$^6$, 350K) 9.82 (1H, t, J 0.8 Hz), 8.98 (1H, d, J 5.6 Hz), 8.13 (1H, s), 8.10 (1H, d), 7.39 (2H, d, J 8.7 Hz), 7.33 (2H, d, J 8.7 Hz), 5.15 (1H, m), 3.68 (4H, m), 3.35 (1H, dd, J 14.2, 4.7 Hz), 3.18 (1H, dd, J 14.2, 9.8 Hz), 1.69 (4H, br), 1.55 (4H, br). m/z (ES$^+$, 70V) 555 (MH$^+$).

EXAMPLE 73

(S)-3-[4-(2,7-Naphthyridin-1-ylamino]phenyl]-2-(2-morpholino-3,4-dioxocyclobut-1-enylamino) propanoic Acid A solution of the compound of Example 1 (20 mg, 0.044 mmol) in methanol (0.2 ml) was treated with morpholine (0.011 ml, 0.12 mmol) and the resulting mixture heated at 60° for 24 h. The mixture was concentrated to dryness then redissolved in anhydrous THF (1.0 ml) and treated with polystyrene methylisocyanate resin (Argonaut Technologies, 150 mg, 1.57 mmol/g, 0.24 mmol) at room temperature for 24 h. The resulting mixture was filtered, and the resin was washed with methanol (1.0 ml). The combined filtrate was evaporated to dryness then redissolved in THF (0.2 ml) and treated with an aqueous solution of lithium hydroxide monohydrate (0.2 ml of a solution of 100 mg in 4.0 ml water, 0.12 mmol) at room temperature for 24 h. The reaction mixture was quenched with glacial acetic acid (0.007 ml, 0.12 mmol), then evaporated to dryness to give the title compound. HPLC-MS Retention time 2.45, 473 (MH$^+$).

EXAMPLE 74

Ethyl (S)-3-[4-(3-isobutyl-2,7-naphthyridin-1-yloxy)phenyl]-2-(2-ethoxy-3,4-dioxocyclobut-1-enylamino)propanoate The title compound was synthesised in a similar manner to the compound of Example 42 from the product of the reaction between Intermediate 20 and ethyl (S)-3-(4-aminophenyl)-2-(t-butyloxycarbonylamino)propanoate. δH (CDCl$_3$) 9.62 (1H, s), 8.62 (1H, d, J 5.8 Hz), 7.45 (1H, d, J 5.8 Hz), 7.15 (2H, d, J 8.6 Hz), 7.12 (2H, d, J 8.6 Hz), 7.00 (1H, s), 6.27, 5.81, 5.12 and 4.57 (together 1H, br m), 4.75, 4.60 (2H, m), 4.19 (2H, q, J 7.1 Hz), 3.23–3.05 (2H, m), 2.48 (2H, d, J 7.1 Hz), 1.94 (1H, septet, J 6.8 Hz), 1.39 (3H, t, J 7.0 Hz), 1.24 (3H, t, J 7.1 Hz) and 0.80 (6H, d, J 6.6 Hz); m/z (ES$^+$) 518 (MH$^+$).

EXAMPLE 75

Ethyl (S)-3-[4-(3-isobutyl-2,7-naphthyridin-1-yloxy)phenyl]-2-(2-azepan-1-yl-3,4-dioxocyclobut-1-enylamino)propanoate Prepared in a similar manner to the compound of Example 43 from the compound of Example 74 and azepane. δH (d$^6$ DMSO) 9.56 (1H, s), 8.69 (1H, d, J 5.7 Hz), 7.79 (1H, d, J 9.2 Hz), 7.75 (1H, d, J 5.7 Hz), 7.31 (2H, d, J 8.5 Hz), 7.29 (1H, s), 7.20 (2H, d, J 8.5 Hz), 5.16 (1H, m), 4.13 (2H, q, J 7.0 Hz), 3.80–3.40 (4H, br m), 3.27 (1H, dd, J 13.9, 4.5 Hz), 3.06 (1H, dd, J 13.9, 10.7 Hz), 2.45 (2H, masked d), 1.88 (1H, septet, J 6.7 Hz), 1.68–1.50 (4H, m), 1.50–1.35 (4H, m), 1.18(3H, t, J 7.1 Hz)and 0.77 (6H, d, J 6.7 Hz); m/z (ES$^+$) 570 (MH$^+$).

EXAMPLE 76

(S)-3-[4-(3-Isobutyl-2,7-naphthyridin-1-yloxy)phenyl]-2-(2-azepan-1-yl-3,4-dioxocyclobut-1-enylamino)propanoic Acid Prepared in a similar manner to the compound of Example 44 from the compound of Example 75. δH (d$^6$ DMSO, 350K) 9.61(1H, s), 8.74 (1H, d, J 5.7 Hz), 7.77 (1H, d, J 5.7 Hz), 7.37 (1H, s), 7.33 (2H, d, J 8.6 Hz), 7.28 (1H, d, J 9.0 Hz), 7.25 (2H, d, J 8.6 Hz), 5.17 (1H, narrow m), 3.72–3.63 (4H, m), 3.33 (1H, dd, J 14.0, 4.2 Hz), 3.15 (1H, dd, J 14.0, 9.8 Hz), 2.57 (2H, d, J 7.0 Hz), 2.01 (1H, septet, J 6.8 Hz), 1.73–1.60 (4H, m), 1.60–1.50 (4H, m) and 0.87 (6H, d, J 6.8 Hz); m/z (ES$^+$) 540 (MH$^+$).

EXAMPLE 77

Ethyl(S)-3-[4-(3-isobutyl-2,7-naphthyridin-1-yloxy)phenyl]-2-(2-N,N-diethylamino-3,4-dioxocyclobut-1-enylamino)propanoate Prepared in a similar manner to the compound of Example 43 from the compound of Example 74 and the diethylamine. δH (d$^6$ DMSO) 9.47 (1H, s), 8.60 (1H, d, J 5.7 Hz), 7.68 (1H, d, J 9.0 Hz), 7.65 (1H, d, J 5.7 Hz), 7.23 (2H, d, J 8.6 Hz), 7.20 (1H, s), 7.10 (2H, d, J 8.6 Hz), 5.08 (1H, m), 4.04 (2H, q, J 6.8 Hz), 3.50–3.30 (4H, m), 3.17 (1H, dd, J 13.9, 4.7 Hz), 2.96 (1H, dd, J 13.9, 10.9 Hz), 2.37 (2H, d), 1.78 (1H, septet, J 6.8 Hz), 1.09 (3H, t, J 7.1 Hz), 0.98 (6H, t, J 7.1 Hz) and 0.69 (6H, d, J 6.8 Hz), m/z (ES$^+$) 545 (MH$^+$).

EXAMPLE 78

(S)-3-[4-(3-Isobutyl-2,7-naphthyridin-1-yloxy)phenyl]-2-(2-N,N-diethylamino-3,4-dioxocyclobut-1-enylamino)propanoic Acid Prepared in a similar manner to the compound of Example 44 from the compound of Example 77. δH (d$^6$ DMSO, 350K) 9.66 (1H, s), 8.77 (1H, d, J 5.7 Hz), 7.81 (1H, d, J 5.7 Hz), 7.41 (2H, d, J 8.7 Hz), 7.40 (1H, d, J 9.2 Hz), 7.37 (1H, s), 7.30 (2H, d, J 8.7 Hz), 5.22 (1H, m), 3.67–3.53 (4H, m), 3.38 (1H, dd, J 14.1, 4.5 Hz), 3.19 (1H, dd, J 14.1, 1 0.1 Hz), 2.61 (2H, d, J 6.8 Hz), 2.05 (1H, septet, J 6.8 Hz), 1.21 (6H, t, J 7.1 Hz) and 0.91 (6H, d, J 6.8 Hz); m/z (ES$^+$) 517 (MH$^+$).

EXAMPLE 79

Ethyl (S)-3-[4-(3-methyl-2,7-naphthyridin-1-ylamino)phenyl]-3-(2-ethoxy-3,4-dioxocyclobut-1-enylamino)propanoate A solution of the crude Intermediate 22 (3.2 g, 8.4 mmol), 1,2-diethoxy-3,4-dioxocyclobut-1-ene (1.43 g, 8.4 mmol), N,N-diisopropylethylamine (2.71 g, 21 mmol) in MeOH (20 ml) was stirred at room temperature for 72 h. The mixture was concentrated in vacuo and purified by chromatography (SiO$_2$; gradient elution EtOAc:Hexane 1:1 to 9:1) to give the title compound as an orange solid, (1.44 g, 36%). δH (d$^6$ DMSO, 400 MHz, 350K) 9.76 (1H, s), 9.37 (1H, s), 8.50 (1H, br s), 7.95 (1H, d, J 2.0 Hz), 7.93 (3H, m), 7.37 (1H, s), 7.36 (2H, d, J 3.0 Hz), 7.35 (1H, s), 5.30 (1H, br s), 4.71 (2H, q, J 7.0 Hz), 4.08 (2H, m), 3.30 (1H, m), 2.97 (1H, dd, J 11.9, 6.2 Hz), 2.5 (3H, s), 1.42 (3H, t, J 7.0 Hz) and 1.19 (3H, t, J 7.0 Hz); m/z (ES$^+$, 70V) 474 (MH$^+$).

EXAMPLE 80

Ethyl (S)-3-[4-(3-methyl-2,7-naphthyridin-1-ylamino)phenyl]-3-[2-(azepan-1-yl)-3,4-dioxocyclobut-1-enylamino]propanoate A solution of the compound of Example 79 (300 mg, 0.63 mmol) and azepane (0.19 g, 1.89 mmol) in MeOH (10 ml) was stirred at room temperature overnight. The solid was isolated by filtration and dried to give the title compound as a pale yellow powder (66 mg, 18%). δH (d$^6$ DMSO) 9.80 (1H, s), 9.55 (1H, m), 8.55 (1H, m), 7.85 (3H, m), 7.50 (1H, m), 7.30 (2H, m), 7.00 (1H, s), 5.90 (1H, m), 4.10 (2H, m), 3.45 (4H, m), 3.25 (1H, m), 3.15 (1H, m), 2.55 (3H, s), 1.60 (4H, m), 1.40 (4H, m) and 1.20 (3H, t); m/z (ES$^+$, 70V) 527 (MH$^+$).

EXAMPLE 81

(S)-3-[4-(3-Methyl-2,7-naphthyridin-1-ylamino)phenyl]-3-[2-(azepan-1-yl)-3,4-dioxocyclobut-1-enylamino]propanoic Acid Prepared in a similar manner to the compound of Example 40 from the compound of Example 80. δH (d$^6$ DMSO, 350K) 9.76 (1H, s), 9.33 (1H, br s), 8.58 (1H, d, J 6.0 Hz), 7.91 (2H, d, J 9.0 Hz), 7.54 (1H, d, J 9.0 Hz), 7.41 (2H, d, J 9.0 Hz), 6.97 (1H, s), 5.75 (1H, m), 3.72 (4H, m), 2.93 (2H, m), 2.48 (3H, s), 1.58 (4H, m), 1.57 (4H, m); m/z (ES$^+$, 70V) 499 (MH$^+$).

EXAMPLE 82

Ethyl (S)-3-[4-(3-methyl-2,7-naphthyridin-1-ylamino)phenyl]-3-(2-N,N-diethylamino-3,4-dioxocyclobut-1-enylamino)propanoate Prepared in a similar manner to the compound of Example 80 from the compound of Example 79 and diethylamine. δH (d$^6$ DMSO, 350K) 9.76 (1H, s), 9.33 (1H, br s), 8.58 (1H, d, J 5.0 Hz), 7.91 (2H, d, J 6.0 Hz), 7.56 (1H, d, J 5.0 Hz), 7.42 (2H, d, J 9.0 Hz), 6.98 (1H, s), 5.78 (1H, t, J 7.0 Hz), 3.59 (4H, m), 2.90 (2H, m), 2.48 (3H, s) and 1.19 (6H, t, J 7.0 Hz); m/z (ES$^+$, 70V) 473 (MH$^+$).

EXAMPLE 83

(S)-3-[4-(3-Methyl-2,7-naphthyridin-1-ylamino)phenyl]-3-(2-N,N-diethylamino-3,4-dioxocyclobut-1-enylamino)propanoic Acid Prepared in a similar manner to the compound of Example 40 from the compound of Example 82. δH (d$^6$ DMSO, 350K) 9.75 (1H, s), 9.4 (1H, s), 8.55 (1H, d), 7.80 (2H, d), 7.70 (1H, d), 7.50 (1H, d), 7.25 (2H, d), 6.80 (1H, s), 5.75 (1H, q), 3.90 (4H, m), 3.85 (1H, m), 3.75 (1H, m), 2.30 (3H, s) and 1.00 (6H, t); m/z (ES$^+$, 70V) 487 (MH$^+$).

EXAMPLE 84

Ethyl (S)-3-[4-(3-methyl-2,7-naphthyridin-1-ylamino)phenyl]-3-[2-(2,5-dimethylpyrrolidin-1-yl)-3,4-dioxocyclobut-1-enylamino]propanoate Prepared in a similar manner to the compound of Example 80 from the compound of Example 79 and 2,5- dimethylpyrrolidine. δH (d⁶ DMSO) 9.74 (1H, s), 9.29 (1H, s), 8.57 (1H, d, J 6.0 Hz), 7.92 (2H, d, J 4.0 Hz), 7.53 (1H, m), 7.40 (2H, d, J 4.0 Hz), 7.35 (1H, s), 5.87 (1H, m), 4.11 (2H, m), 4.09 (2H, m), 3.62 (3H, s), 3.14 (1H, m), 3.08 (1H, m), 2.47 (3H, s), 1.75 (2H, m), 1.71 (2H, m), 1.31 (6H, m) and 1.19 (3H, t, J 7.0 Hz). m/z (ES⁺, 70V) 527 (MH⁺).

EXAMPLE 85

(S)-3-[4-(3-Methyl-2,7-naphthyridin-1-ylamino)phenyl]-3-[2-(2,5-dimethylpyrrolidin-1-yl)-3,4-dioxocyclobut-1-enylamino]propanoate Prepared in a similar manner to the compound of Example 40 from the compound of Example 84. δH (d⁶ DMSO) 9.76 (1H, s), 9.50 (1H, s), 8.58 (1H, d, J 5.0 Hz), 7.89 (2H, m), 7.58 (1H, d, J 5.0 Hz), 7.39 (2H, d, J 9.0 Hz), 6.98 (1H, s), 5.75 (1H, m), 4.20 (2H, m), 4.09 (1H, m), 2.82 (2H, m), 2.44 (3H, s), 2.10 (2H, m), 1.68 (2H, m) and 1.28 (6H, d, J 6.0 Hz). m/z (ES⁺, 70V) 499 (MH⁺).

LC-MS Conditions: Lunca C18(2) 50×4.6 mm (3 um) column, running a gradient of 95% [0.1% aqueous formic acid], 5% [0.1% formic acid in acetonitrile] to 5% [0.1% aqueous formic acid], 95% [0.1% formic acid in acetonitrile] over 3 min, then maintaining the mobile phase at that ratio for a further 2 min. Flow rate 1.0 m/min. MS was acquired by API electrospray in positive ion mode, at 80V, scanning from 120 to 1000 amu.

The compounds of Examples 86–122 shown in Table 1 were prepared from the compound of Example 1 in a similar manner to the compound of Example 73 using the appropriate amine in place of morpholine.

The compounds of Examples 123–129 shown in Table 2 were prepared from the compound of Example 30 in a similar manner to the compound of Example 73 using the appropriate amine in place of morpholine.

In each of the Tables 1 and 2 the letter $X^1$ indicates the point of attachment of the amine fragment ($R^1$) to the square in the structure at the head of the table.

TABLE 1

| | R1 | MH+ | HPLC Retention Time (min) |
|---|---|---|---|
| EXAMPLE 86 | X₁–N(2-methylpiperidine) | 486 | 2.72 |
| EXAMPLE 87 | X₁–N(2,5-dimethylpyrrolidine) | 486 | 2.71 |
| EXAMPLE 88 | X₁–N(diisobutyl) | 516 | 2.67 |
| EXAMPLE 89 | X₁–N(piperidine) | 472 | 2.63 |

TABLE 1-continued
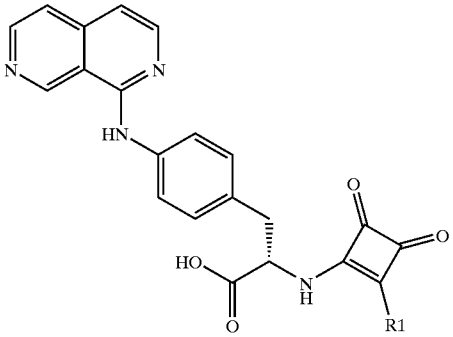
| | R1 | MH+ | HPLC Retention Time (min) |
|---|---|---|---|
| EXAMPLE 90 | 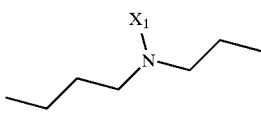 | 516 | 3.02 |
| EXAMPLE 91 | 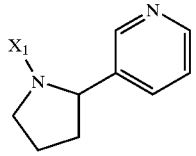 | 535 | 2.33 |
| EXAMPLE 92 | 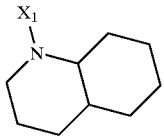 | 526 | 2.94 |
| EXAMPLE 93 | 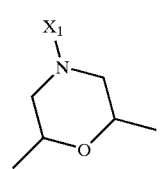 | 502 | 2.57 |
| EXAMPLE 94 | 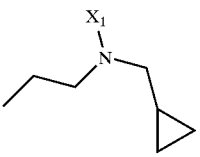 | 500 | 2.84 |
| EXAMPLE 95 | 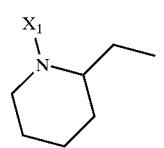 | 500 | 2.79 |
| EXAMPLE 96 | 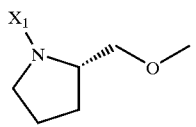 | 502 | 2.65 |
| EXAMPLE 97 | 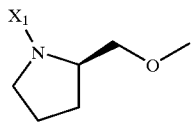 | 502 | 2.63 |

TABLE 1-continued
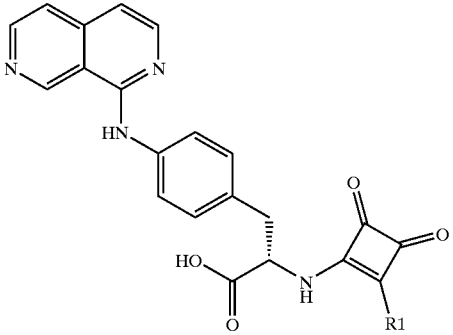
| | R1 | MH+ | HPLC Retention Time (min) |
|---|---|---|---|
| EXAMPLE 98 | 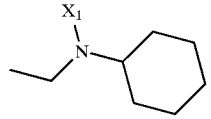 | 514 | 2.91 |
| EXAMPLE 99 | 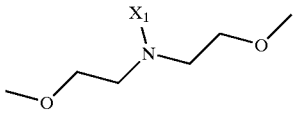 | 520 | 2.62 |
| EXAMPLE 100 | 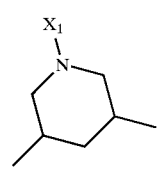 | 500 | 2.86 |
| EXAMPLE 101 | 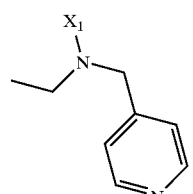 | 523 | 2.31 |
| EXAMPLE 102 | 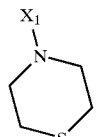 | 490 | 2.64 |
| EXAMPLE 103 | 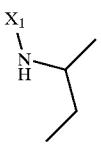 | 460 | 2.67 |
| EXAMPLE 104 | 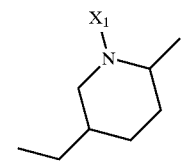 | 514 | 2.94 |

TABLE 1-continued
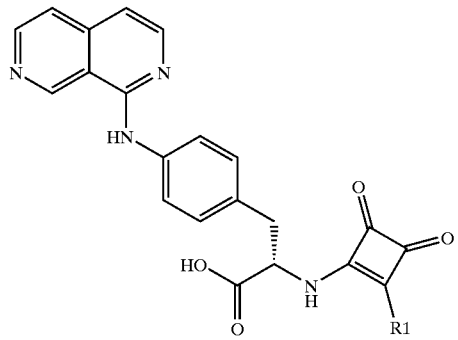
| | R1 | MH+ | HPLC Retention Time (min) |
|---|---|---|---|
| EXAMPLE 105 | 3-methylpiperidinyl | 486 | 2.75 |
| EXAMPLE 106 | azepanyl | 486 | 2.7 |
| EXAMPLE 107 | N-methyl-N-((R)-1-phenylethyl)amino | 522 | 2.87 |
| EXAMPLE 108 | pyrrolidinyl | 457 | 2.51 |
| EXAMPLE 109 | tert-butylamino | 460 | 2.69 |
| EXAMPLE 110 | N-methyl-N-benzylamino | 508 | 2.81 |
| EXAMPLE 111 | 3,3-dimethyl-azabicyclic | 540 | 2.96 |

TABLE 1-continued

| | R1 | MH+ | HPLC Retention Time (min) |
|---|---|---|---|
| EXAMPLE 112 | [pyrrolidine with two CH2OMe groups, N-X1] | 546 | 2.71 |
| EXAMPLE 113 | [N(X1)(ethyl)(isopropyl)] | 474 | 2.68 |
| EXAMPLE 114 | [N(X1)(ethyl)(ethyl)] | 460 | 2.6 |
| EXAMPLE 115 | [NH(X1)(propyl)] | 445 | 2.56 |
| EXAMPLE 116 | [azocane, N-X1] | 500 | 2.68 |

TABLE 1-continued
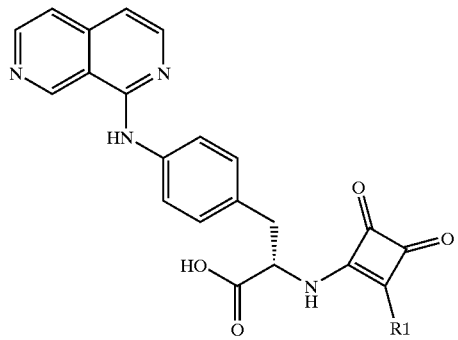
| | R1 | MH+ | HPLC Retention Time (min) |
|---|---|---|---|
| EXAMPLE 117 | | 520 | 2.76 |
| EXAMPLE 118 | | 536 | 2.85 |
| EXAMPLE 119 | | 501 | 2.09 |
| EXAMPLE 120 | | 587 | 2.72 |
| EXAMPLE 121 | | 522 | 2.79 |
| EXAMPLE 122 | | 486 | 2.6 |

TABLE 2

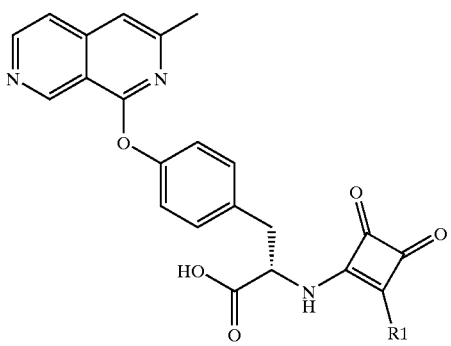

| | R1 | MH+ | HPLC Retention Time (min) |
|---|---|---|---|
| EXAMPLE 123 | 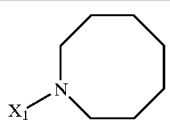 | 515 | 3.26 |
| EXAMPLE 124 | 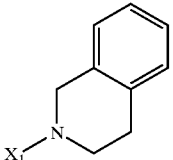 | 535 | 3.36 |
| EXAMPLE 125 | 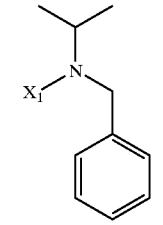 | 551 | 3.56 |
| EXAMPLE 126 | 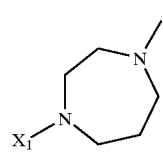 | 516 | 2.39 |
| EXAMPLE 127 | 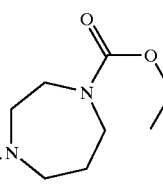 | 602 | 3.28 |
| EXAMPLE 128 | 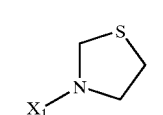 | 491 | 3.00 |
| EXAMPLE 129 | 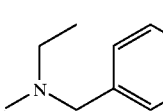 | 537 | 3.43 |

The following assays can be used to demonstrate the potency and selectivity of the compounds according to the invention. In each of these assays an $IC_{50}$ value was determined for each test compound and represents the concentration of compound necessary to achieve 50% inhibition of cell adhesion where 100%=adhesion assessed in the absence of the test compound and 0%=absorbance in wells that did not receive cells.

$\alpha_4\beta_1$ Integrin-Dependent Jurkat Cell Adhesion to VCAM-1g 96 well NUNC plates were coated with $F(ab)_2$ fragment goat anti-human IgG Fcγ-specific antibody [Jackson Immuno Research 109-006-098: 100 µl at 2 µg/ml in 0.1M $NaHCO_3$, pH 8.4], overnight at 4°. The plates were washed (3×) in phosphate-buffered saline (PBS) and then blocked for 1 h in PBS/1% BSA at room temperature on a rocking platform. After washing (3× in PBS) 9 ng/ml of purified 2d VCAM-1g diluted in PBS/1% BSA was added and the plates left for 60 minutes at room temperature on a rocking platform. The plates were washed (3×in PBS) and the assay then performed at 37° for 30 min in a total volume of 200 µl containing $2.5 \times 10^5$ Jurkat cells in the presence or absence of titrated test compounds.

Each plate was washed (2×) with medium and the adherent cells were fixed with 100 µl methanol for 10 minutes followed by another wash. 100 µl 0.25% Rose Bengal (Sigma R4507) in PBS was added for 5 minutes at room temperature and the plates washed (3×) in PBS. 100 µl 50% (v/v) ethanol in PBS was added and the plates left for 60 min after which the absorbance (570nm) was measured.

$\alpha_4\beta_7$ Integrin-Dependent JY Cell Adhesion to MAdCAM-1g

This assay was performed in the same manner as the $\alpha_4\beta_2$ assay except that MAdCAM-1g (150 ng/ml) was used in place of 2d VCAM-1g and a sub-line of the β-lympho blastoid cell-line JY was used in place of Jurkat cells. The $IC_{50}$ value for each test compound was determined as described in the $\alpha_4\beta_1$ integrin assay.

$\alpha_5\beta_1$ Integrin-Dependent K562 Cell Adhesion to Fibronectin 96 well tissue culture plates were coated with human plasma fibronectin (Sigma F0895) at 5 µg/ml in phosphate-buffered saline (PBS) for 2 hr at 37° C. The plates were washed (3×in PBS) and then blocked for 1 h in 100 µl PBS/1% BSA at room temperature on a rocking platform. The blocked plates were washed (3×in PBS) and the assay then performed at 37° C. in a total volume of 200 µl containing $2.5 \times 10^5$ K562 cells, phorbol-12-myristate-13-acetate at 10 ng/ml, and in the presence or absence of titrated test compounds. Incubation time was 30 minutes. Each plate was fixed and stained as described in the $\alpha_4\beta_1$ assay above.

$\alpha_m\beta_2$-Dependent Human Polymorphonuclear Neutrophils Adhesion to Plastic 96 well tissue culture plates were coated with RPMI 1640/10% FCS for 2 h at 37° C. $2 \times 10^5$ freshly isolated human venous polymorphonuclear neutrophils (PMN) were added to the wells in a total volume of 200 µl in the presence of 10 ng/ml phorbol-12-myristate-13-acetate, and in the presence or absence of test compounds, and incubated for 20 min at 37° C. followed by 30 min at room temperature. The plates were washed in medium and 100 µl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows. PMN lysate samples mixed with 0.22% $H_2O_2$ (Sigma) and 50 μg/ml TMB (Boehringer Mannheim) in 0.1M sodium acetate/citrate buffer, pH 6.0 and absorbance measured at 630 nm.

αIIb/β$_3$-Dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of $6\times10^8$/ml in autologous plasma. Cuvettes contained equal volumes of PRP and filtered Tyrode's buffer (g/liter: NaCl 8.0; $MgCl_2.H_2O$ 0.427; $CaCl_2$ 0.2; KCl 0.2; D-glucose 1.0; $NaHCO_3$ 1.0; $NaHPO_4.2H_2O$ 0.065). Aggregation was monitored following addition of 2.5 μM ADP (Sigma) in the presence or absence of inhibitors.

In the above assays the preferred compounds of the invention in which $R^1$ is an $\alpha_4$ integrin binding group, such as the compounds of the Examples generally have $IC_{50}$ values in the $\alpha_4\beta_1$ and $\alpha_4\beta_7$ assays of 1 μM and below. In the other assays featuring α integrins of other subgroups the same compounds had $IC_{50}$ values of 50 μM and above thus demonstrating the potency and selectivity of their action against $\alpha_4$ integrins.

The advantageous clearance properties of compounds according to the invention may be demonstrated as follows:

Hepatic clearance, whether metabolic or biliary, can make a substantial contribution to the total plasma clearance of a drug. The total plasma clearance is a principal parameter of the pharmacokinetic properties of a medicine. It has a direct impact on the dose required to achieve effective plama concentrations and has a major impact on the elimination half-life and therefore the dose-interval. Furthermore, high hepatic clearance is an indicator of high first-pass hepatic clearance after oral administration and therefore low oral bioavailability.

Many peptidic and non-peptidic carboxylic acids of therapeutic interest are subject to high hepatic clearance from plasma. Except for drugs which function in the liver, hepatic uptake from blood or plasma is undesirable because it leads to high hepatic clearance if the compound is excreted in bile or metabolised, or if the substance is not cleared from the liver, it may accumulate in the liver and interfere with the normal function of the liver.

The total plasma clearance of a compound according to the invention can be determined as follows:

a small dose of the compound in solution is injected into a vein of a test animal. Blood samples are withdrawn from a blood vessel of the animal at several times after the injection, and the concentration of compound in the bleed or plasma is measured using a suitable assay. The area under the curve (AUCiv) is calculated by non-compartmental methods (for example, the trapezium method) or by pharmacokinetic modelling. The total plasma clearance ($CL_p$) is calculated by dividing the intravenous dose($D_{iv}$) by the $AUC_{iv}$ for the blood plasma concentration–time course of a drug administered by the intravenous route:

$$CL_p = D_{iv} \div AUC_{iv}$$

When tested in this manner, compounds according to the invention are not rapidly or extensively extracted by the liver and have low total plasma clearance where low is defined as less than 10 ml/min/kg in the laboratory rat (Sprague Dawley CD). This compares favourably with functionally equivalent integrin binding compounds in which the squaric acid framework and/or the carboxylic ester or amide R group of compounds of formula (1) is not present.

What is claimed is:

1. A compound of formula (1):

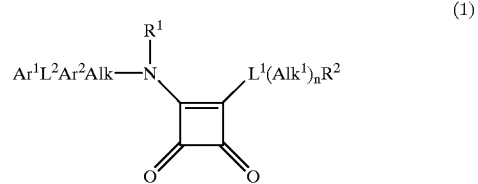

(1)

wherein
Ar$^1$ is an optionally substituted 2,7-naphthridin-1-yl group;
L$^2$ is a covalent bond or a linker atom or group;
Ar$^2$ is an optionally substituted aromatic or heteroaromatic chain;
Alk is a chain

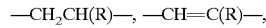

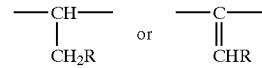

in which R is a carboxylic acid (—CO$_2$H) or a derivative or biostere thereof;
R$^1$ is a hydrogen atom or a C$_{1-6}$alkyl group;
L$^1$ is a covalent bond or a linker atom or group;
Alk$^1$ is an optionally substituted aliphatic chain;
n is zero or the integer 1;
R$^2$ is a hydrogen atom or an optionally substituted heteroaliphatic, cycloaliphatic, heterocycloaliphatic, polycycloalphatic, heteropoly-cycloaliphatic, aromatic or heteroaromatic group;
and the salts, solvates, hydrates and n-oxides thereof.

2. A compound according to claim 1 in which Alk is a chain

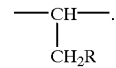

3. A compound according to claim 1 in which R is a carboxylic acid (—CO$_2$H) group.

4. A compound according to claim 1 in which R is an esterified carboxyl group of formula —CO$_2$Alk$^7$.

5. A compound according to claim 1 in which Ar$^2$ is an optionally substituted phenylene group.

6. A compound according to claim 1 in which R$^1$ is a hydrogen atom.

7. A compound according to claim 1 in which L$^2$ is an —O— atom or —N(R$^8$)— group.

8. A compound according to claim 7 in which R$^8$ is a hydrogen atom or a methyl group.

9. A compound according to claim 1 in which L$^1$ is a —N(R$^8$)— group where R$^8$ is a hydrogen atom or a C$_{1-6}$alkyl group.

10. A compound according to claim 1 in which $L^1$ is a covalent bond and n is the integer 1.

11. A compound according to claim 1 in which n is the integer 1 and $Alk^1$ is an optionally substituted straight or branched $C_{1-6}$alkylene chain.

12. A compound according to claim 11 in which $Alk^1$ is a —$CH_2$—, —$CH_2CH_2$—, —$CH_2CH_2CH_2$—, —$CH(CH_3)CH_2$— or —$C(CH_3)_2CH_2$— chain.

13. A compound according to claim 12 in which $R^2$ is a hydrogen.

14. A compound according to claim 1 in which $L^1$ is a covalent bond and n is zero.

15. A compound according to claim 14 in which $R^2$ is an optionally substituted $C_{5-7}$heterocycloaliphatic group.

16. A compound according to claim 15 in which $R^2$ is an optionally substituted piperadinyl, homopiperidinyl, heptamethyleneiminyl, pyrrolidinyl, piperazinyl, homopiperazinyl, morpholinyl or thiomorpholinyl group.

17. A compound according to claim 1 of formula (2):

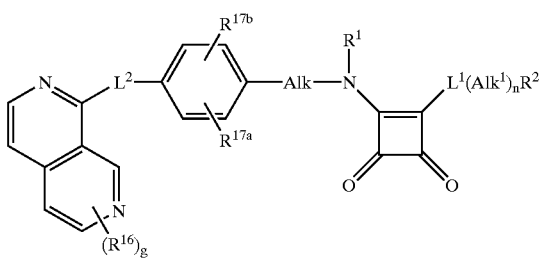

(2)

wherein g is zero or the integer 1, 2, 3, 4 or 5;
$R^{16}$ is a hydrogen atom or an atom or group -$L^3$($Alk^2$)$_t L^4(R^4)_u$ in which;
$L^3$ is a covalent bond or a linker atom or group;
$Alk^2$ is an aliphatic or heteroaliphatic chain;
t is zero or the integer 1;
$L^4$ is a covalent bond or a linker atom or group;
u is the integer 1, 2 or 3;
$R^4$ is a hydrogen or halogen atom or a group selected from optionally substituted $C_{1-6}$alkyl or $C_{3-8}$cycloalkyl, —$OR^5$ [where $R^5$ is a hydrogen atom, an optionally substitued $C_{1-6}$alkyl or $C_{3-8}$ cycloalkyl group], —$SR^5$, —$NR^5R^6$ [where $R^6$ is as just defined for $R^5$ and may be the same or different], —$NO_2$, —CN, —$CO_2R^5$, —$SO_3H$, —$SOR^5$, —$SO_2R^5$, —$SO_3R^5$, —$OCO_2R^5$, —$CONR^5R^6$, —$OCONR^5R^6$, —$CSNR^5R^6$, —$COR^5$, —$OCOR^5$, —$N(R^5)COR^6$, —$N(R^5)CSR^6$, —$SO_2N(R^5)(R^6)$, —$N(R^5)SO_2R^6$, $N(R^5)CON(R^6)(R^7)$ [where $R^7$ is a hydrogen atom, an optionally substituted $C_{1-6}$alkyl or $C_{3-8}$cycloalkyl group], —$N(R^5)CSN(R^6)(R^7)$ or —$N(R^5)SO_2N(R^6)(R^7)$, provided that when t is zero and each of $L^3$ and $L^4$ is a covalent bond then u is the integer 1 and $R^4$ is other than a hydrogen atom;
$R^{17a}$ and $R_{17b}$ is each an atom or group as herein defined for $R^{16}$;
and the salts, solvates, hydrates and n-oxides thereof.

18. A compound which is selected from the group consisting of:
(S)-3-[4-(2,7-Naphthyridin-1-ylamino)phenyl]-2-[2-N,N-diethylamino-3,4-dioxocyclobut-1-enylamino]propanoic acid;
(S)-3-[4-(2,7-Naphthyridin-1-ylamino)phenyl]-2-[2-N,N-di-n-propylamino-3,4-dioxocyclobut-1-enylamino]propanoic acid;
(S)-3-[4-(2,7-Naphthyridin-1-ylamino)phenyl]-2-[2-(cis-2,5-dimethylpyrrolidin-1-yl)-3,4-dioxocyclobut-1-enylamino]propanoic acid;
(S)-3-[4-(2,7-Naphthyridin-1-ylamino)phenyl]-2-[2-(trans-2,5-dimethylpyrrolidin-1,-yl)-3,4-dioxocyclobut-1-enylamino]propanoic acid;
(S)-3-[4-(2,7-Naphthyridin-1-yloxy)phenyl]-2-[2-N,N-diethylamino-3,4-dioxocyclobut-1-enylamino]propanoic acid;
(S)-3-[4-(2,7-Naphthyridin-1-yloxy)phenyl]-2-[2-N,N-di-n-propylamino-3,4-dioxocyclobut-1-enylamino]propanoic acid;
(S)-3-[4-(2,7-Naphthyridin-1-yloxy)phenyl]-2-[2-(cis-2,5-dimethylpyrrolidin-1-yl)-3,4-dioxocyclobut-1-enylamino]propanoic acid;
(S)-3-[4-(2,7-Naphthyridin-1-ylamino)phenyl]-2-[(2-[(2S),(5S)-dimethylpyrrolidin-1-yl)-3,4-dioxocyclobut-1-enyl)amino]propanoic acid;
(S)-3-[4-(2,7-Naphthyridin-1-yloxy)phenyl]-2-[2-(azepan-1-yl)-3,4-dioxocyclobut-1-enylamino]propanoic acid;
(S)-3-[4-(3-Methyl-2,7-naphthyridin-1-ylamino)phenyl]-2-[2-N,N-diethylamino-3,4-dioxocyclobut-1-enylamino]-propanoic acid;
(S)-3-[4-(3-Methyl-2,7-naphthyridin-1-ylamino)phenyl]-2-[2-N,N-di-n-propylamino-3,4-dioxocyclobut-1-enylamino]-propanoic acid;
(S)-3-[4-(3-Methyl-2,7-naphthyridin-1-ylamino)phenyl]-2-[2-(cis-2,5-dimethylpyrrolidin-1-yl)-3,4-dioxocyclobut-1-enylamino]propanoic acid;
(S)-3-[4-(3-Methyl-2,7-naphthyridin-1-yloxy)phenyl]-2-[2-N,N-diethylamino-3,4-dioxocyclobut-1-enylamino]propanoic acid;
(S)-3-[4-(3-Methyl-2,7-naphthyridin-1-yloxy)phenyl]-2-[2-N,N-di-n-propylamino-3,4-dioxocyclobut-1-enylamino]propanoic acid;
(S)-3-[4-(3-Methyl-2,7-naphthyridin-1-yloxy)phenyl]-2-[2-(cis-2,5-dimethylpyrrolidin-1-yl)-3,4-dioxocyclobut-1-enylamino]propanoic acid;
(S)-3-[4-(3-Methyl-2,7-naphthyridin-1-yloxy)phenyl]-2-[2-(trans-dimethypyrrolidin-1-yl)-3,4-dioxocyclobut-1-enylamino]propanoic acid;
(S)-3-[4-(3-Methyl-2,7-naphthyridin-1-yloxy)phenyl]-2-[2-(azepan-1-yl)-3,4-dioxocyclobut-1-enylamino]propanoic acid;
(S)-3-[4-(3-Methyl-2,7-naphthyridin-1-ylamino)phenyl]-2-[2-(azepan-1-yl-3,4-dioxocyclobut-1-enylamino]propanoic acid;
(S)-3-[4-(3-Isobutyl-2,7-naphthyridin-1-yloxy)phenyl]-2-[2-(azepan-1-yl)-3,4-dioxocyclobut-1-enylamino)propanoic acid;
(S)-3-[4-(3-Isobutyl-2,7-naphthyridin-1-yloxy)phenyl]-2-[2-N,N-diethylamino-3,4-dioxocyclobut-1-enylamino]propanoic acid;
and the salts solvates, hydrates, N-oxides and carboxylic acid esters thereof.

19. A pharmaceutical composition comprising a compound according to claim 1 together with one or more pharmaceutically acceptable carriers, excipients or diluents.

20. A compound according to claim 18, wherein said carboxylic acid esters are selected from the group consisting of methyl, ethyl, n-propyl and i-propyl esters.

* * * * *